United States Patent [19]

Solomon et al.

[11] Patent Number: 5,449,680

[45] Date of Patent: Sep. 12, 1995

[54] 2,2 DISUBSTITUTED GLYCEROL AND GLYCEROL-LIKE COMPOUNDS, COMPOSITIONS AND METHODS OF USE

[75] Inventors: Daniel Solomon, Edison; James J. Kaminski, Long Valley, both of N.J.; Steven K. White, Leawood, Kans.; Laura S. Lehman de Gaeta, La Jolla, Calif.; Ashit K. Ganguly, Upper Montclair, N.J.

[73] Assignee: Schering Corporation, Kenilworth, N.J.

[21] Appl. No.: 955,784

[22] Filed: Oct. 2, 1992

Related U.S. Application Data

[60] Division of Ser. No. 758,448, Sep. 6, 1991, Pat. No. 5,185,334, which is a continuation of Ser. No. 389,668, Jul. 31, 1989, abandoned.

[51] Int. Cl.⁶ .............. C07D 277/82; A61K 31/425
[52] U.S. Cl. .................... 514/365; 514/367; 514/370; 514/77; 548/164; 548/194; 548/196; 548/201; 548/204
[58] Field of Search ............ 548/187, 204, 201, 196, 548/164, 194; 514/365, 367, 370

[56] References Cited

U.S. PATENT DOCUMENTS

| | | | |
|---|---|---|---|
| 4,119,714 | 10/1978 | Kny et al. | 424/199 |
| 4,329,302 | 5/1982 | Hanahan et al. | 260/925 |
| 4,372,949 | 2/1983 | Kodama et al. | 424/199 |
| 4,504,474 | 3/1985 | Hanahan et al. | 514/78 |
| 4,552,869 | 11/1985 | Lautenschlager et al. | 514/77 |
| 4,582,824 | 4/1986 | Nishikawa et al. | 514/77 |
| 4,610,979 | 9/1986 | Lautenschalger et al. | 514/77 |
| 4,731,384 | 3/1988 | Doll et al. | 514/658 |
| 4,749,805 | 6/1988 | Eibl | 558/169 |

FOREIGN PATENT DOCUMENTS

| | | |
|---|---|---|
| 0070433 | 1/1983 | European Pat. Off. . |
| 0094586 | 11/1983 | European Pat. Off. . |
| 0109255 | 5/1984 | European Pat. Off. . |
| 0138559 | 10/1984 | European Pat. Off. . |
| 0142333 | 5/1985 | European Pat. Off. . |
| 0145303 | 6/1985 | European Pat. Off. . |
| 0146258 | 6/1985 | European Pat. Off. . |
| 0147768 | 7/1985 | European Pat. Off. . |
| 0157609 | 10/1985 | European Pat. Off. . |
| 0208932 | 1/1987 | European Pat. Off. . |
| 0254540 | 1/1988 | European Pat. Off. . |
| 0255366 | 2/1988 | European Pat. Off. . |
| 3133925 | 3/1983 | Germany . |
| 3209670 | 9/1983 | Germany . |
| 6115792 | 9/1981 | Japan . |
| 8013592 | 1/1983 | Japan . |
| 8035194 | 3/1983 | Japan . |
| 1063617 | 4/1986 | Japan . |

OTHER PUBLICATIONS

Touvay et al., 6th Int. Conf. on Prostaglandins, Abstr. Bk. p. 194 (Jun. 3–6, 1986).
Bittman et al., J. Lipid Res. 28, 733 (1987).
Ohno et al., J. Med. Chem. 29, 1812, (1986).
Venuti, Ann. Rep. Med. Chem. Pawson, Ed. 193, (1985).
Drugs of the Future, 12 (1), 14 (1987).
Scrip PAF Report, PJB Publications Ltd., UK, (1986).

*Primary Examiner*—Robert Gerstl
*Attorney, Agent, or Firm*—Henry C. Jeanette

[57] ABSTRACT

Novel 2,2-disubstituted glycerol-like compounds are disclosed for use as anti-allergic and anti-inflammatory compounds. The compounds are antagonists of platelet activating factor ("PAF"). Also disclosed are methods of synthesizing and using the compounds of the invention as well as pharmaceutical compositions thereof. The compounds have the formula

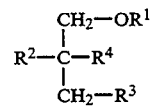

wherein $R^1$, $R^2$, $R^3$, and $R^4$ are as defined in the specification.

17 Claims, No Drawings

2,2 DISUBSTITUTED GLYCEROL AND GLYCEROL-LIKE COMPOUNDS, COMPOSITIONS AND METHODS OF USE

This is a division, of application Ser. No. 07/758,448 filed 16 Sep. 1991, now U.S. Pat. No. 5,185,334 which is a continuation of U.S. application Ser. No. 07/389,668 filed Jul. 31, 1989, now abandoned which is a continuation-in-part of International Application No. PCT/U.S. 89/00336 filed Feb. 2, 1989, which is a continuation-in-part of International Application No. PCT/US 88/00315 filed on Feb. 5, 1988, the benefit of which applications is claimed pursuant to the provisions of 35 U.S.C.§§120, 363 and 365(c).

The present invention relates to 2,2-disubstituted glycerol and glycerol-like compounds, compositions containing such compounds, and methods of using such compounds.

Various publications have disclosed related compounds. For example, the *SCRIP PAF REPORT*, PJB Publications, 1986 and *Ann. Rep. Med. Chem.*, V20 (1985) Ch. 20, pp. 193-202 disclose numerous related compounds synthesized by various researchers. *J. Med. Chem.*, Vol. 29, No. 10, pp. 1812 to 1814 (1986) and *J. Lipid Res.* Vol. 28, pp 733 to 738 (1987) disclose related PAF analogs. Similarly, *Drugs of the Future*, Vol. 12 (1), p. 14 (1987) discloses numerous related compounds synthesized by a variety of researchers which are related to the compounds described and claimed herein.

SUMMARY OF THE INVENTION

The invention described and claimed herein encompasses a compound represented by the formula I

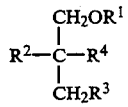

or a pharmaceutically acceptable salt or solvate thereof wherein:

$R^1$ is alkyl containing 6 to 22 carbon atoms, —C(O)—D or —C(S)—D wherein

D is $NR^5R^6$;

$R^5$ is hydrogen, alkyl containing x carbon atoms, aryl, heteroaryl, heteroalkyl, arylalkyl, or cycloalkyl, wherein said alkyl, aryl, heteroaryl, heteroalkyl, arylalkyl or cycloalkyl groups may be substituted;

$R^6$ is alkyl containing y carbon atoms, aryl, heteroaryl, heteroalkyl, arylalkyl or cycloalkyl, wherein said alkyl, aryl, heteroaryl, heteroalkyl, arylalkyl and cycloalkyl groups may be substituted, such that the sum of x and y, when at least one of $R^5$ or $R^6$ is alkyl is an integer of from 1 to 22; or $R^5$ and $R^6$ together with the nitrogen to which they are attached may form a heterocycloalkyl group which may be substituted with alkyl or arylalkyl;

$R^2$ is lower alkyl, trifluoromethyl, arylalkyl or aryl, wherein said aryl and said arylalkyl groups may be substituted;

$R^3$ is T—U—V, wherein

T represents —OPO3—, O—C(O)—O—, —O—, —S—, —NR$^a$—, —NR$^a$SO2—, O—C(O)—NR$^a$— or —NR$^a$—C(O)—O— wherein R$^a$ is H, lower alkyl or acyl;

U is —(CH2)$_e$— wherein e is an integer of from 2 to 10 or

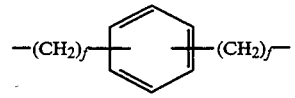

where each f is independently 1, 2 or 3;

V is A—B, wherein A is a direct bond between U and B, —O—, —S—, —O—(CH2)$_n$— where n is 1, 2 or 3, —O—C(O)— or —N(R$^a$)— where R$^a$ is as previously defined;

B is alkyl, substituted alkyl, heteroalkyl, substituted heteroalkyl, heterocycloalkyl, substituted heterocycloalkyl, aryl, substituted aryl, heteroaryl, substituted heteroaryl or

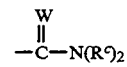

where W is O, S or NR$^b$, wherein R$^b$ is H, lower alkyl or CN and each R$^c$ is independently H or lower alkyl, such that the group A—B contains at least one nitrogen atom, and $R^4$ represents —X—C$_b$H$_{2b+1}$ where b is an integer of from 1 to 6 and X is methylene, O, S(O)$_c$ where c is 0, 1 or 2 or —N(R$^a$)— where R$^a$ is as previously defined;

with the proviso that when $R^1$ is alkyl, T cannot be —OPO3.

Preferred compounds falling within the invention include compounds where $R^1$ is —C(O)—D where D is $NR^5R^6$, with preferred values of $R^5$ and $R^6$ being alkyl. Most preferably, one of $R^5$ and $R^6$ is methyl, and the other group is alkyl containing six to nineteen carbon atoms, most preferably ten to eighteen carbon atoms.

Preferred compounds falling within the invention also include preferred values of $R^2$ where $R^2$ is lower alkyl, more preferably lower alkyl containing one to three carbon atoms, and most preferably lower alkyl containing one or two carbon atoms.

Preferred compounds of the invention also include compounds having preferred values of T, which include —O—, —O—C(O)—O—, —O—C(O)—NR$^a$— and —NR$^a$—C(O)—O— where R$^a$ is preferably H or acyl and most preferably acyl. The more preferred values of T are —O—, —O—C(O)—NR$^a$— and —NR$^a$—C(O)—O—, with the most preferred value of T being —O—.

Preferred values of U include —(CH2)$_e$— and in particular where e is the integer 4, 5, 6 or 7. Another preferred value of U is —(CH2)$_f$— phenyl —(CH2)$_f$— wherein f is as defined previously.

Preferred values of V include those wherein A is a direct bond between U and V and B is heteroaryl or substituted heteroaryl, wherein A is a direct bond between U and B and B is heterocycloalkyl or substituted heterocycloalkyl, wherein A is —O— and B is heteroaryl or substituted heteroaryl, and wherein A is —N(R$^a$)— and B is heteroaryl or substituted heteroaryl.

Preferred values of $R^4$ include those compounds where X is O or S(O)$_2$ and b in the group C$_b$H$_{2b+1}$ is 1.

Also, included are preferred salts of a compound represented by structural formula I, including zwitterions, N-oxides, quaternary ammonium compounds, both cyclic and acyclic, the preferred cyclic compounds being quaternary ammonium compounds where the ring contains a quaternary nitrogen and the preferred acyclic compounds being quaternary ammonium compounds, quaternized with lower alkyl substituent groups.

The vast majority of the compounds of this invention contain at least one assymetric carbon atom. This invention covers all individual stereoisomers of the compounds of formula I as well as mixtures of two or more different stereoisomers.

The invention further encompasses a pharmaceutical composition comprising a compound represented by structural formula I in combination with a pharmaceutically acceptable carrier.

The invention also encompasses a method of treating allergy in a mammal comprising administering to said mammal an antiallergic effective amount of a compound represented by structural formula I.

The invention further encompasses a method of treating inflammation in a mammal comprising administering to said mammal an antiinflammatory effective amount of a compound represented-by structural formula I.

Another aspect of the invention comprises the use of a compound of formula I for preparing a pharmaceutical composition useful for treating allergy or inflammation. Yet another aspect of the invention comprises a method for making a pharmaceutical composition by mixing a compound of formula I with a pharmaceutically acceptable carrier.

Preferred species falling within the scope of the invention described and claimed herein are set forth below wherein X— represents a negatively charged ion such as Cl— or CH₃SO₃—:

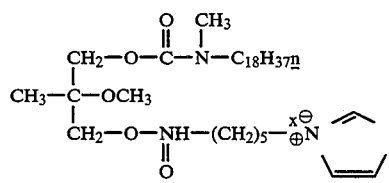

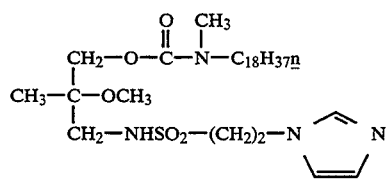

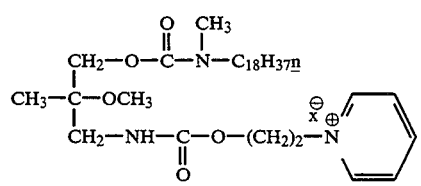

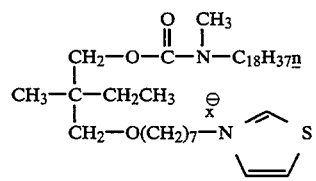

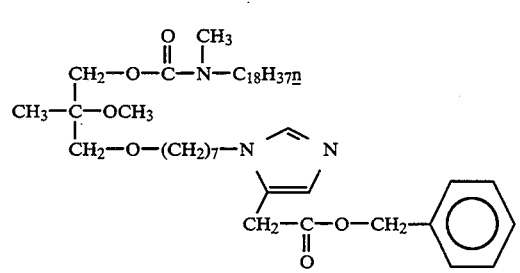

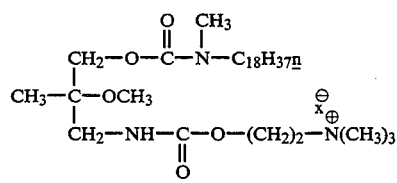

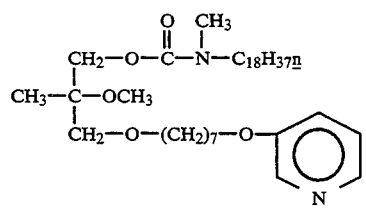

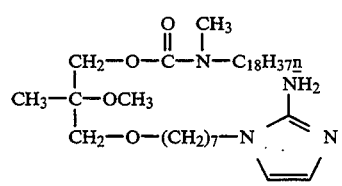

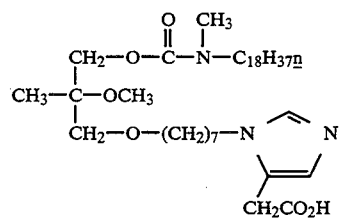

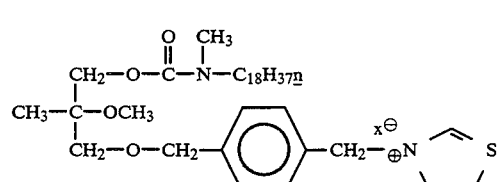

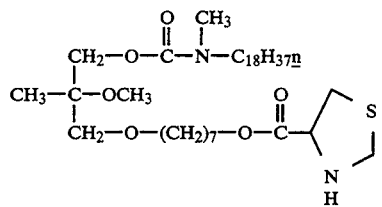
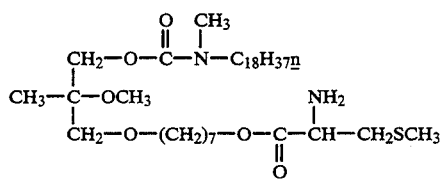
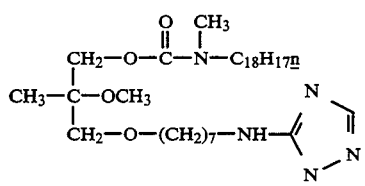
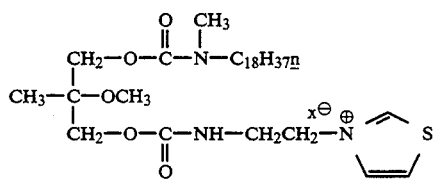
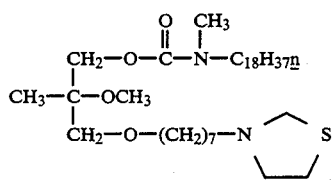
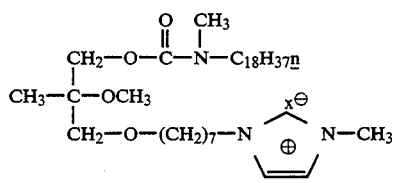
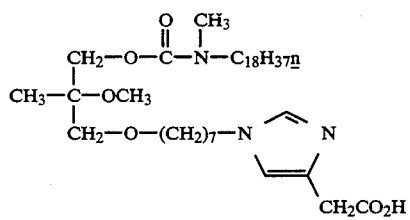
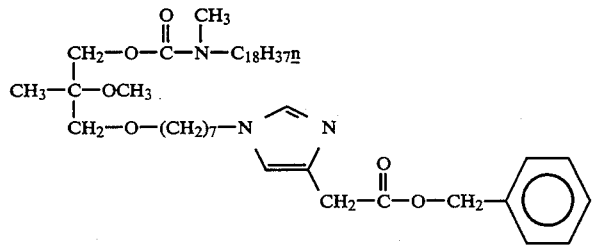
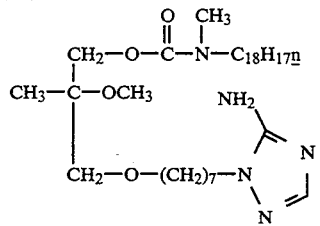
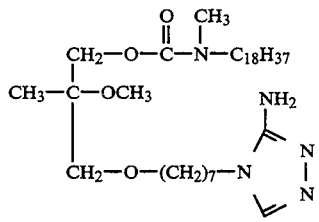
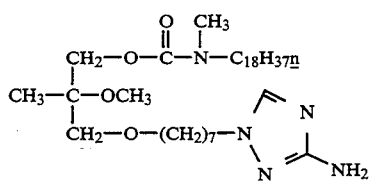
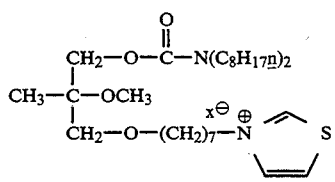
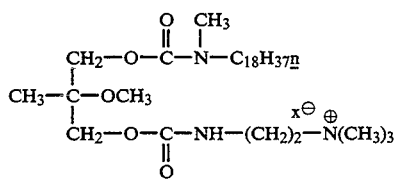
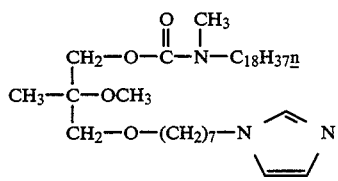
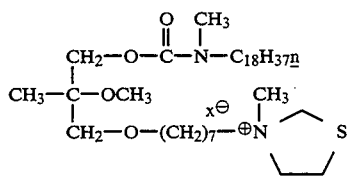
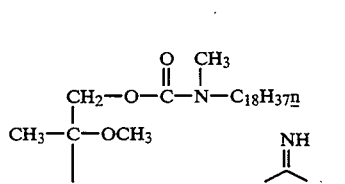
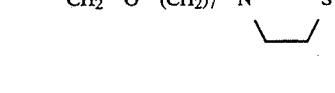

-continued
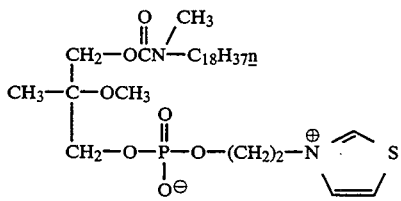
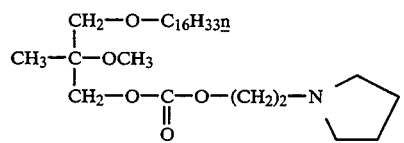
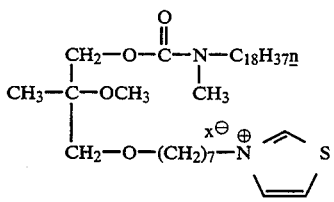
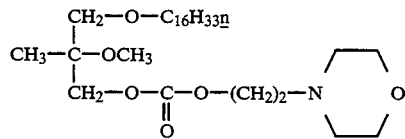
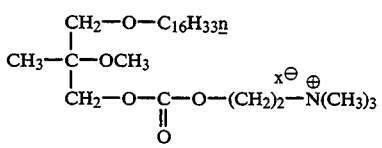
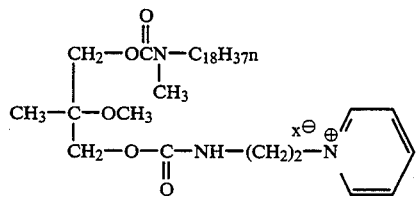
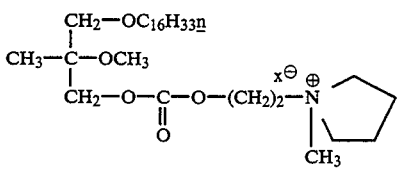
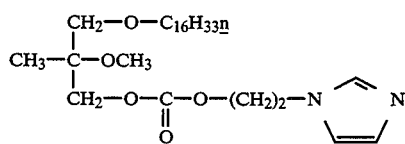
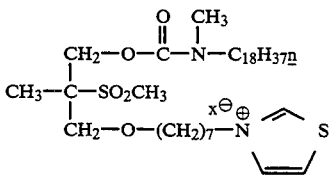
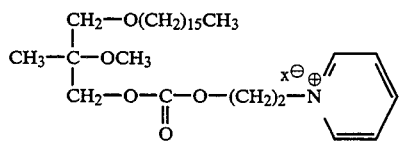
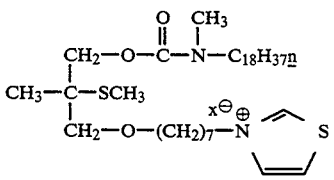
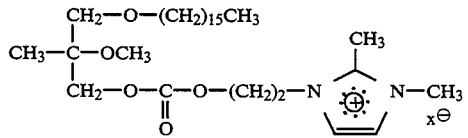
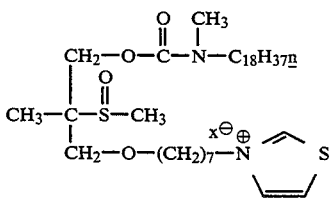
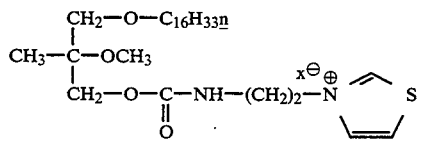
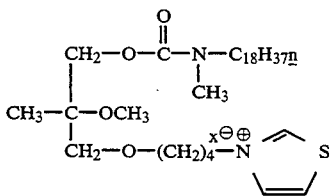
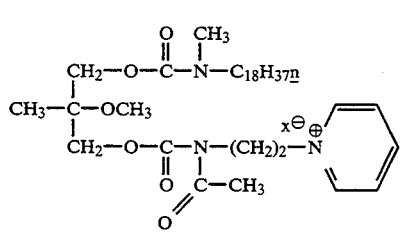

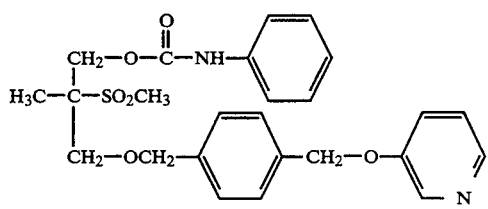
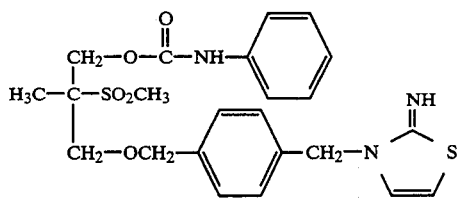
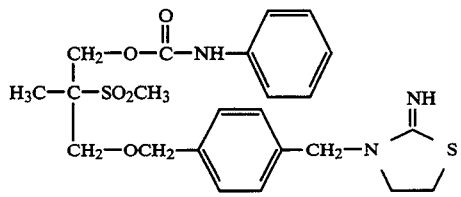
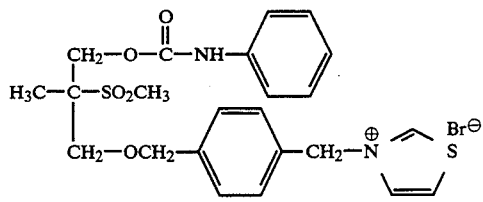
Other preferred species include:
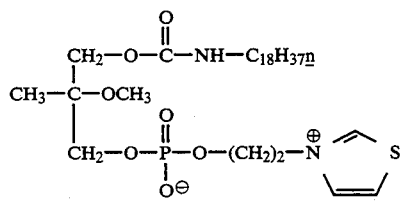
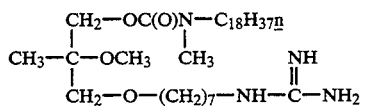
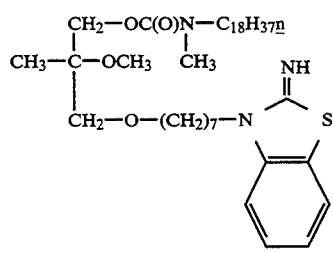
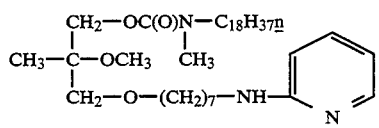
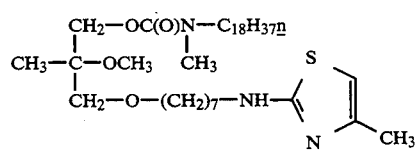
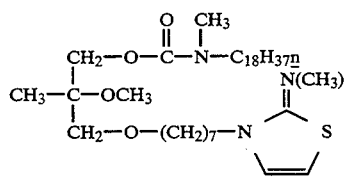

5,449,680
-continued
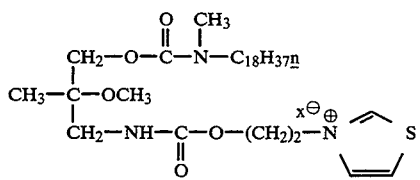
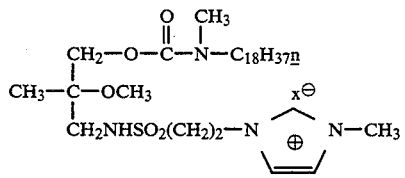
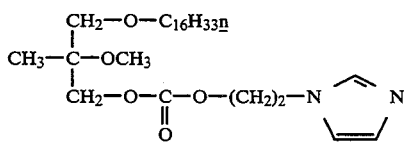
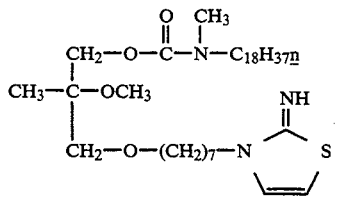
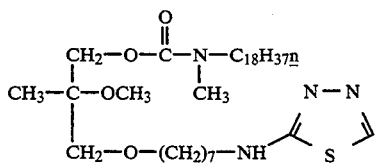
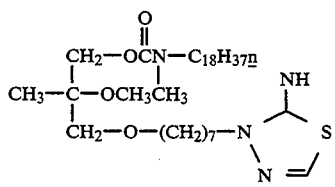
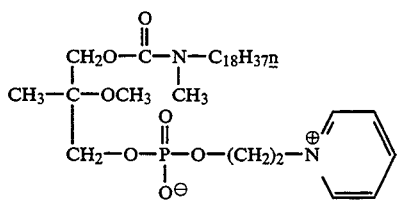
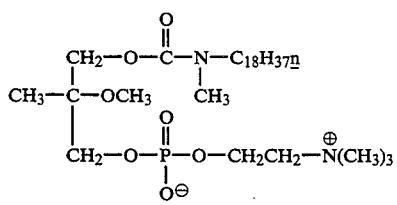
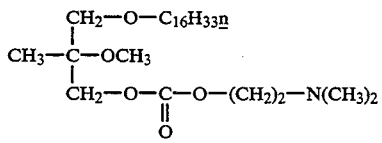
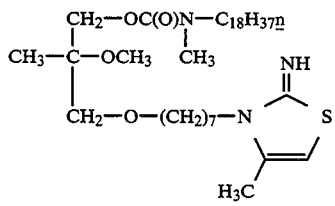
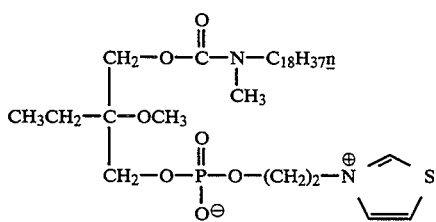
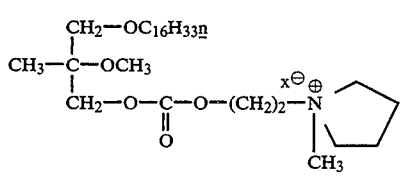
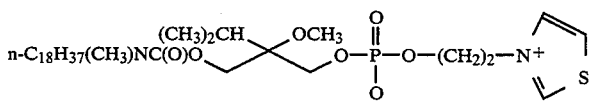
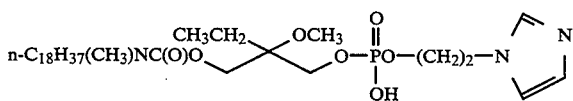
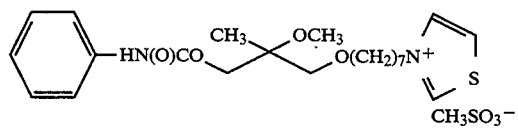

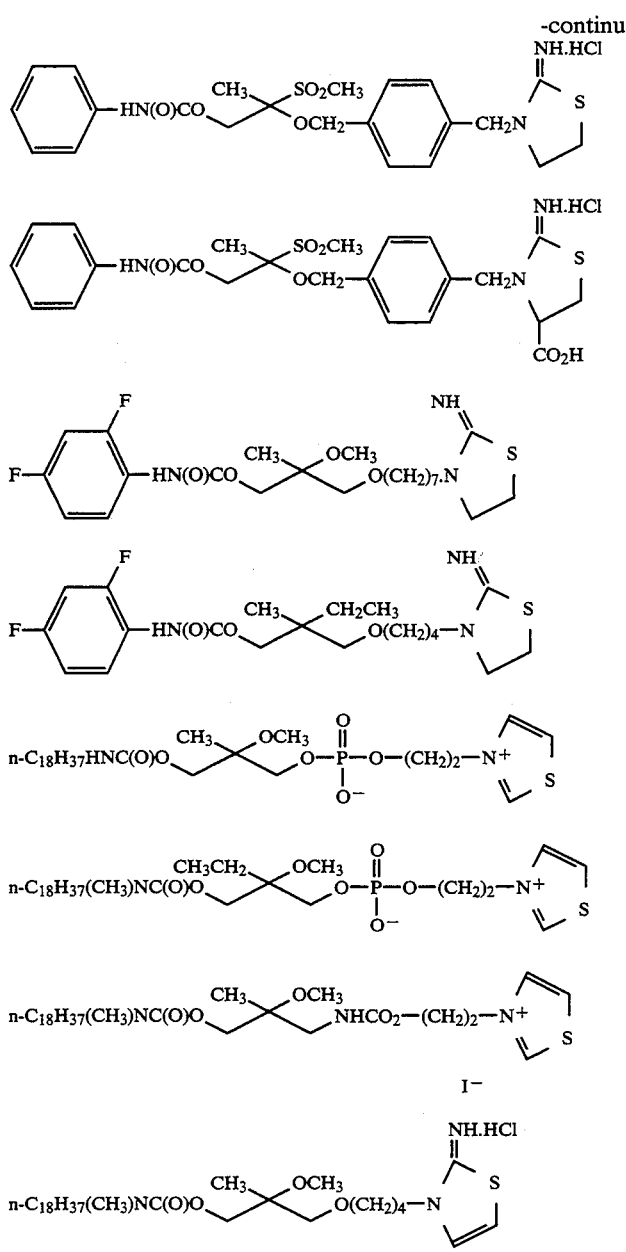

As used herein, the following terms are used as defined below unless otherwise indicated:

alkyl—represents a straight or branched carbon chain containing from one to twenty carbon atoms, preferably one to eighteen carbon atoms;

lower alkyl—represents a straight or branched carbon chain containing from one to six carbon atoms;

methylene—represents the divalent group —CH$_2$—;

cycloalkyl—represents a saturated carbocyclic ring of from three to eight carbon atoms;

heterocycloalkyl—represents a saturated ring containing from three to seven atoms, preferably two to six carbon atoms and 1 to 3 hetero groups selected from O, S, SO, SO$_2$ or N. Preferred heterocycloalkyl groups include morpholino, pyrrolidinyl, thiazolidinyl, and thiazolidinium.

heteroalkyl—represents a saturated branched or unbranched chain containing from one to ten carbon atoms and at least one hetero group selected from O, S, SO, SO$_2$ or N;

acyl—represents a group alkyl—C(O)— or cycloalkyl—C(O)— where alkyl and cycloalkyl are as defined above;

aryl—represents a carbocyclic group containing from 6 to 14 carbon atoms and having at least one aromatic ring (e.g., phenyl or naphthyl);

arylalkyl—represents a saturated branched or unbranched chain containing 1 to 6 carbon atoms and one or more aryl substituents as defined above (e.g., benzyl);

heteroaryl—represents a 5 or 6 membered aromatic ring containing from 1 to 4 heteroatoms; preferred heteroaryl groups include thiazolyl, thiazolium, imidazolyl, imidazolium, pyridinyl and pyridinium;

halo—means chloro, bromo or fluoro;

substituted aryl and heteroaryl—represent aryl and heteroaryl as defined above with each substitutable carbon atom being intended as a possible point of substitution with one or more of halo, alkyl, =NR$^a$, —N(R$^a$)$_2$, —SR$^a$, —OR$^a$ or —CO$_2$R$^a$ wherein $R^a$ is as previously defined, and each substitutable heteroatom being intended as a possible point of substitution with alkyl, —N($R^a$)$_2$, —S$R^a$, —O$R^a$ or —CO$_2$$R^a$ wherein $R^a$ is as previously defined;

substituted heterocycloalkyl—heterocycloalkyl as defined above with each substitutable carbon atom being intended as a possible point of substitution with one or more of alkyl, =N$R^a$, —N($R^a$)$_2$, —S$R^a$, —O$R^a$ or —CO$_2$$R^a$ wherein $R^a$ is as previously defined, and with each substitutable heteroatom being intended as a possible point of substitution with —N($R^a$)$_2$, —O$R^a$, —S$R^a$ or —CO$_2$$R^a$. Substituted heterocycloalkyl also includes non-aromatic quaternary ammonium compounds; and substituted alkyl, substituted cycloalkyl and substituted heteroalkyl—represent alkyl, cycloalkyl and heteroalkyl as defined above, with each substitutable carbon atom being intended as a possible point of substitution with one or more of alkyl, =N$R^a$, —N($R^a$)$_2$, —S$R^a$, —O$R^a$ or —CO$_2$$R^a$ wherein $R^a$ is as previously defined, and with each substitutable heteroatom being intended as a possible point of substitution with —N($R^a$)$_2$, —O$R^a$, —S$R^a$ or —CO$_2$$R^a$.

DESCRIPTION OF THE INVENTION

Certain compounds of the invention may exist in isomeric forms. The invention contemplates all such isomers both in pure form and in admixture, including racemic mixtures.

The compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

Certain compounds of the invention are acidic in nature, e.g. those compounds which possess a carboxyl or phenolic hydroxyl group. These compounds may form pharmaceutically acceptable salts. Examples of such salts are the sodium, potassium, calcium, aluminum, gold, copper and silver salts. Also contemplated are salts formed with pharmaceutically acceptable amines such as ammonia, alkyl amines, hydroxy alkylamines, N-methylglucamine and the like and zwitterions.

Certain basic compounds of the invention are pharmaceutically acceptable salts, e.g., acid addition salts, quaternary ammonium salts and N-oxides. For example, thiazolidine moieties may form acid addition salts with strong acid. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate.

The quaternary ammonium salts are typically prepared by reaction of a tertiary amino group in a compound of formula I with a compound containing a suitable leaving group, such as an alkyl iodide, etc.

For example, in the definition of $R^3$, where B is substituted heteroalkyl, substituted heterocycloalkyl or substituted heteroaryl, B may contain a quaternary nitrogen. The compounds of the invention which possess an aromatic ring nitrogen atom, as defined above, may also form quaternary ammonium salts at the aromatic ring nitrogen atom. Where A in the definition of V is —O—, or —S—, and B is heteroalkyl, substituted heteroalkyl, heterocycloalkyl, substituted heterocycloalkyl, heteroaryl or substituted heteroaryl, the heteroatom in the B group is located at any position other than attached to the A group.

The free base forms differ from their respective salt forms somewhat in certain physical properties, such as solubility in polar solvents, but the salts are otherwise equivalent to their respective free base forms for purposes of the invention.

All such acid, base and quaternary salts are intended to be pharmaceutically acceptable salts within the scope of the invention and all acid and base salts are considered equivalent to the free forms of the corresponding compounds for purposes of the invention.

The compounds of the present invention are produced by the following processes:

(A) a compound of the formula

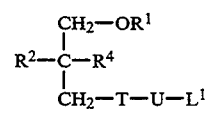   i$_1$ is reacted with a compound of the formula

   i$_2$ wherein $R^1$, $R^2$, $R^4$, T, U, A and B are defined previously and $L^1$ and $L^2$ are leaving groups;

(B) to produce a compound of formula I having a positive charge on radical B and A is a direct bond between U and B, reacting a compound of the formula i$_1$ with a compound of the formula

   i$_3$ wherein B is a free compound that is the same as the B radical defined previously without a bond;

(C) to produce a compound of formula I wherein T is —OCO$_2$—, reacting a compound of the formula

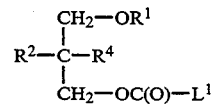   i$_4$ wherein $R^1$, $R^2$, $R^4$ and $L^1$ are as defined previously with a compound of the formula

   i$_5$ when $L^2$ is a leaving group and U and V are as defined previously;

(D) to produce a compound of formula I wherein $R^1$ is C(O)N$R^5$$R^6$ wherein $R^5$ is H and $R^6$ is alkyl, alkylating a compound of the formula

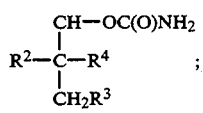

wherein, in the above processes, any functional groups are protected if necessary or desired, followed if necessary or desired by one or more of the following steps:

(a) removing one or more protective groups,
(b) converting a compound of formula I to a different compound of formula I,
(c) converting the so formed compound to a salt or solvate, and
(d) converting the so formed compound to a zwitterion.

The above processes are typically performed in the presence of inert solvent at temperatures that do not exceed the boiling point of the solvent. Typical leaving groups $L^1$ are —$OSO_2CH_3$, —Br, —I, and —Cl. Typical leaving groups $L^2$ are —H, and a metal ion. Of course, many other leaving groups will suffice.

The intermediates $i_1$, $i_2$, $i_3$, $i_4$, $i_5$, and $i_6$ are known or may be prepared in accordance with the following reaction schemes and preparative examples.

Compounds II and III below are conventional starting materials, or may be prepared using conventional methods.

In compound II, and throughout the reaction scheme, $R^2$ is alkyl, trifluoromethyl, aryl or arylalkyl.

In compound II where $R^2$ is aryl, said compound may be prepared by conventional methods, taking into account, in particular Searles, et. al., *J. Org. Chem.* Vol.24, p. 1839 (1960) where $R^2$ is phenyl. The teachings of Searles are incorporated herein by reference.

In compound III, $R^6$ is alkyl containing 6 to 22 carbon atoms, as defined above.

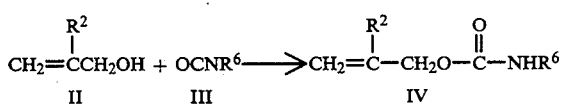

With reference to structural formula I, as represented by formula IV above, $R^1$ represents —C(O)—NHR$^6$. $R^1$ and —C(O)—NHR$^6$ are used below interchangably when appropriate.

In compound IV above as well as throughout the reaction scheme, when $R^5$ in structural formula I represents hydrogen, $R^5$ is designated as H. When $R^5$ is a value other than H, it is designated as $R^5$. L as used throughout the general process description designates a leaving group, and P throughout the general process description designates any appropriate protecting group.

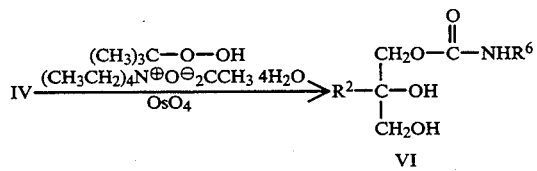

-continued

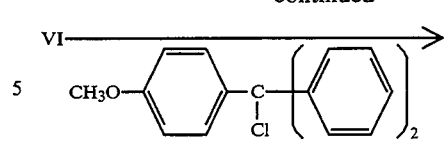

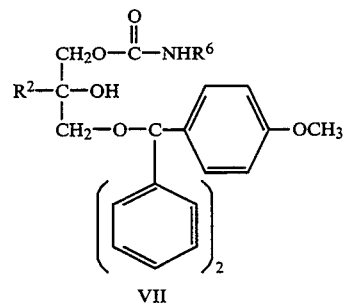

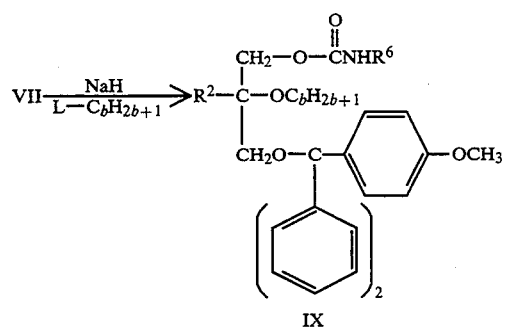

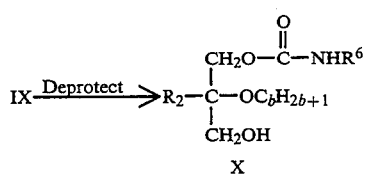

Compound IX may be deprotected, for example, using ethereal hydrochloric acid or alternatively catalytic hydrogenation.

To make compounds of the invention where $R^1$ in formula I is alkyl, substitute $R^1$—L, where L is, e.g., I, Br, Cl, tosylate, mesylate, etc., into the reaction with compound II in place of the isocyanate. Compound I! may be treated with a strong base, such as NaH, to form an alkoxide, after which the reaction with R1—L occurs.

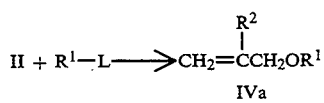

To prepare a compound of the invention containing a 3-ether substituent, (T in the definition of $R^3$ is —O—), the following reaction may be utilized.

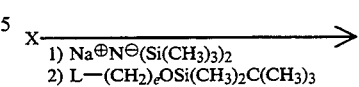

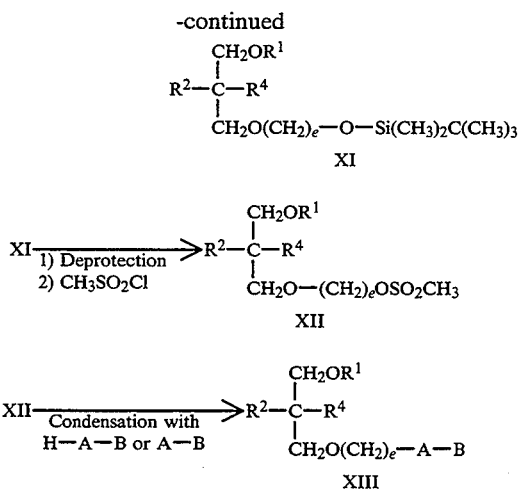

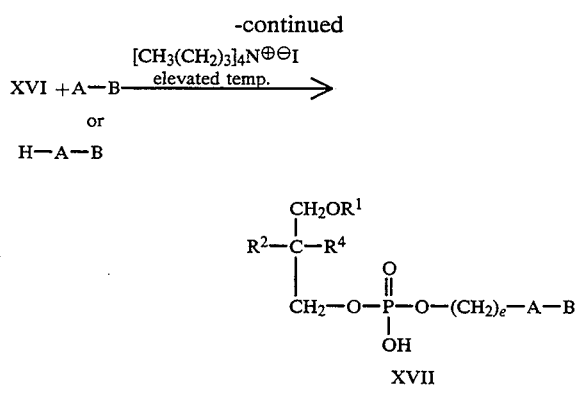

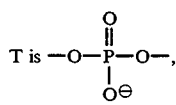

the following general reaction sequence may be utilized.

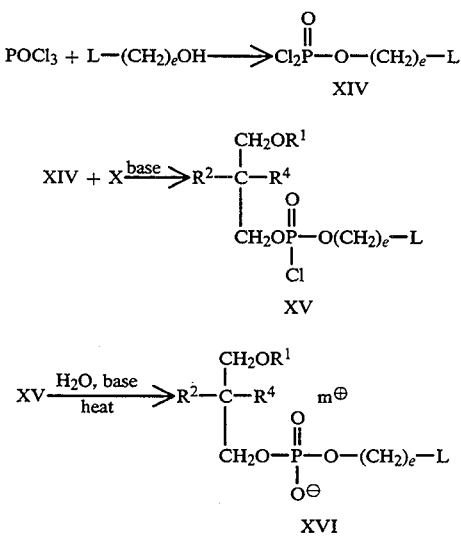

Depending upon the basicity of the A—B moiety the phosphate group of compound XVII may transfer its hydrogen to the A—B moiety becoming negatively charged, thereby forming a zwitterionic compound XVII. Zwitterionic forms of the compounds falling within the scope of formula I are included as part of this invention.

When compound XII is converted to compound XIII, it is treated with an appropriate nucleophilic reagent to displace the mesylate leaving group. The reaction may be run neat or in the presence of inert solvents, one example of which is dimethylformamide ("DMF").

When primary or secondary amines are reacted with compound XII above, secondary and tertiary amines are formed in compound XIII, respectively. To prepare a quaternary ammonium compound, a tertiary amine is typically reacted with compound XII. Alternatively, compound XII may be reacted with a primary or secondary amine, and the resulting secondary or tertiary amine may be reacted with a suitable reagent to form a quaternary compound.

To prepare a compound of the invention where $R^3$ contains a phosphate group, i.e. $R^3$ is T—U—V where To prepare a compound of formula I where carbon atom number 2 in the glycerol backbone is dialkyl substituted, the following general reaction scheme may be utilized. In the reaction scheme, $R^4$ is typically methyl or ethyl, but any other appropriate group could be substituted therefor. $R^2$ and $R^4$ may be the same or different.

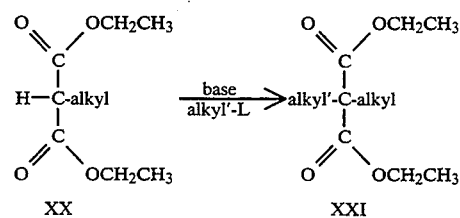

The diester XXI may be reduced to the corresponding diol without affecting the $R^2$ and $R^4$ substituents at carbon atom 2.

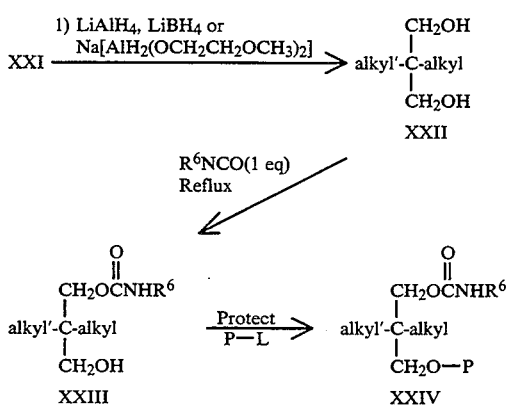

After protecting the oxygen at carbon atom 3, the carbamate nitrogen in the side chain attached to carbon atom 1 of the glycerol backbone may be substituted with a group $R^5$, where $R^5$ is other than hydrogen and the 3-hydroxy substituent may undergo deprotection.

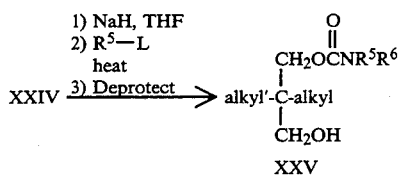

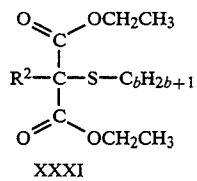

Phosphorylation of compound XXV may be performed as described with respect to compound X. Alternatively, an alkyl side chain —(CH$_2$)$_e$— may be added to the hydroxyl group at carbon atom 3 to form an ether as was previously described with respect to compound X.

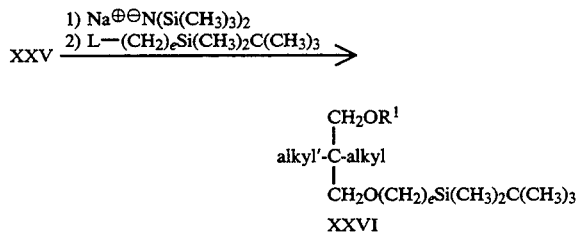

Compound XXXI may then be reduced at positions 1 and 3, to form a corresponding 1,3-diol.

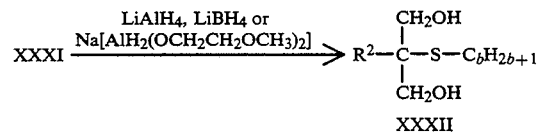

Compound XXXII may be treated with the appropriate alkyl isocyanate, under an inert atmosphere, with appropriate heating as necessary. Protection, N-alkylation, and deprotection steps may be performed as appropriate.

The silyl protecting group may be removed by conventional means, and the resulting hydroxyalkyl side-chain can be mesylated.

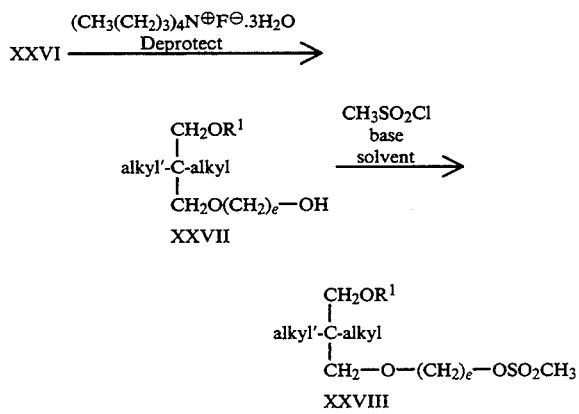

The mesylate compound XXVIII readily reacts with H—A—B or A—B, to form a compound falling within the scope of formula I.

To make the compounds of the invention where R$^4$ contains a thioether, compound XXX may be treated with base and 1-alkylthiosulfonyl-4-methyl benzene to form compound XXXI below.

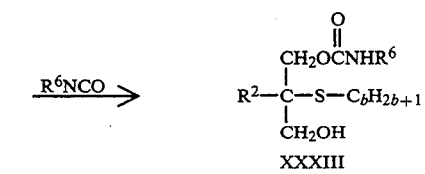

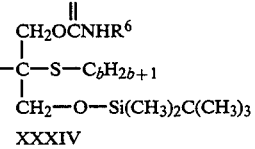

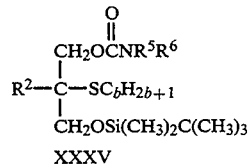

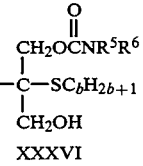

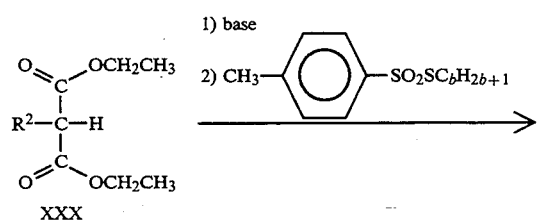

The 3-hydroxy compound XXXVI may be alkylated to form compound XXXVII using a protected alkyl chain reagent, which then undergoes deprotection.

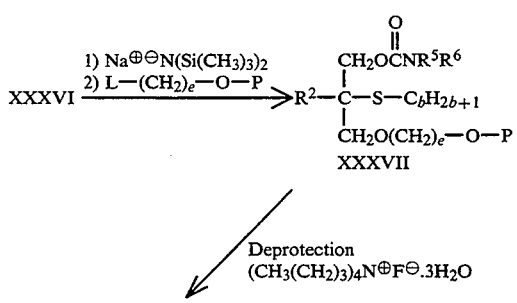

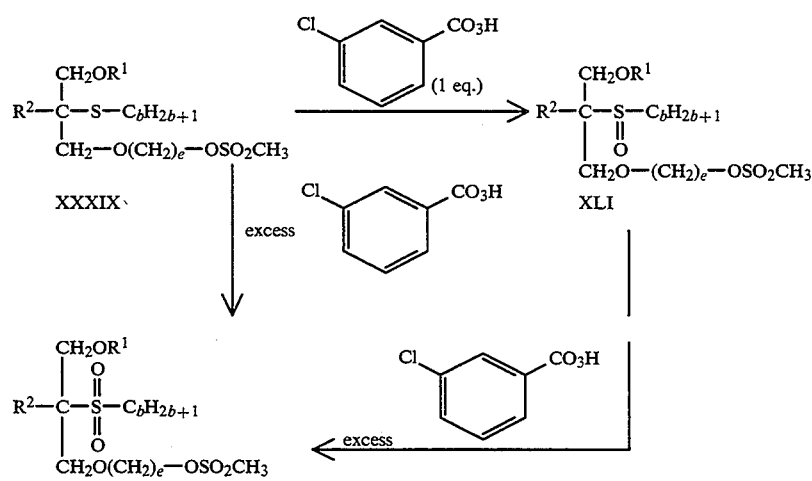

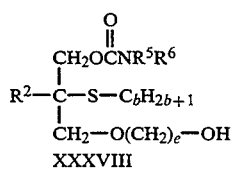

Compound XXXVIII may be subjected to mesylate formation thereby making compound XXXIX, and subsequent mesylate displacement with, H—A—B or A—B as appropriate to form a compound of formula I.

To prepare a compound of formula I where position two of the glycerol backbone is substituted with a sulfoxide or sulfone, the thioether compound XXXIX maybe oxidized to the sulfoxide or sulfone using equimolar or an excess amount of metachloroperbenzoic acid (m-CPBA), respectively.

Displacement of the mesylate protecting group may be performed as described above.

To prepare compounds of the invention represented by formula I where T in the definition of R3 represents —NR$^a$—SO$_2$—, the following modifications to the general reaction scheme may be utilized.

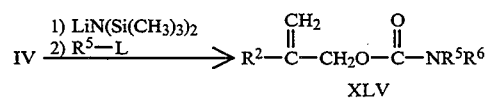

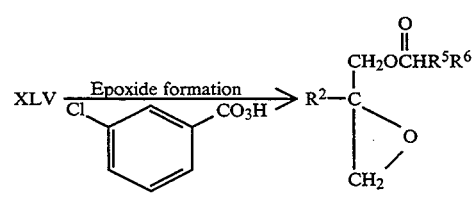

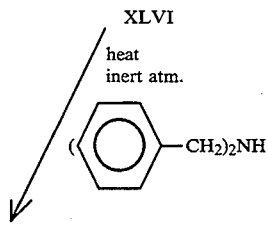

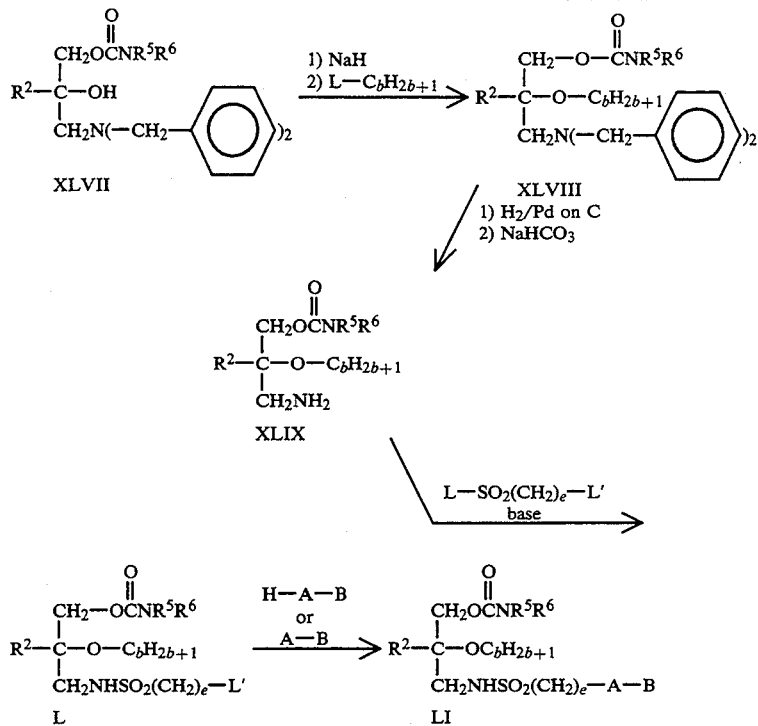

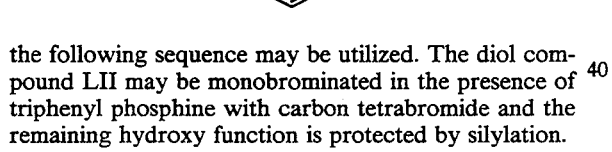

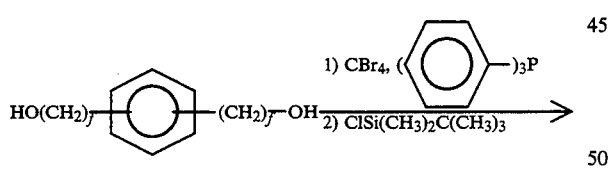

To prepare compounds falling within the scope of formula I where U in the definition of $R^3$ is $$-(CH_2)_f-\phantom{x}\text{phenyl}\phantom{x}-(CH_2)_{f'}-$$

the following sequence may be utilized. The diol compound LII may be monobrominated in the presence of triphenyl phosphine with carbon tetrabromide and the remaining hydroxy function is protected by silylation.

Compound LIII may be utilized in a reaction with any appropriately protected intermediate compound containing a 3-hydroxy group to alkylate said intermediate at position 3.

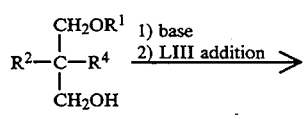

-continued

[LIV, LV, LVI, LVII structures]

To prepare a compound of the invention where T in the definition of $R^3$ represents a carbonate moiety, $-OCO_2-$, a suitable alcohol may first be treated with a strong base to form the anion, then treated with trichloromethyl chloro formate, to yield a compound LVIII.

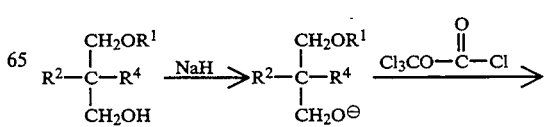

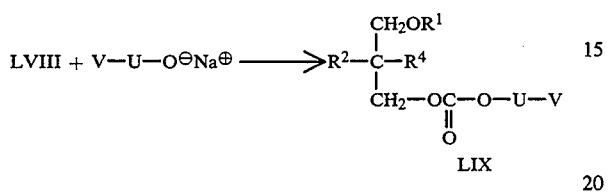

LVIII

Compound LVIII may then be treated with V—U—O⁻Na⁺, to yield compound LIX.

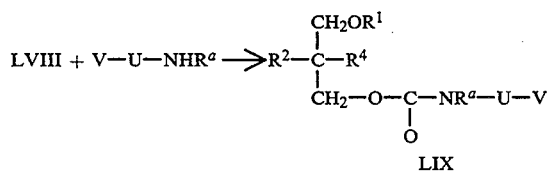

LIX

By substituting an appropriate primary or secondary amine into the preceding reaction, a carbamate (T=—OC(O)NR$^a$—) may be prepared.

LVIII + V—U—NHR$^a$ →R$^2$—C—R$^4$ (CH$_2$OR$^1$ / CH$_2$—O—C(O)—NR$^a$—U—V)

LIX

To prepare the reverse carbamate, the intermediate compound below may be treated with trichloromethyl chloroformate, and the intermediate product LX treated with V—U—O⁻Na⁺.

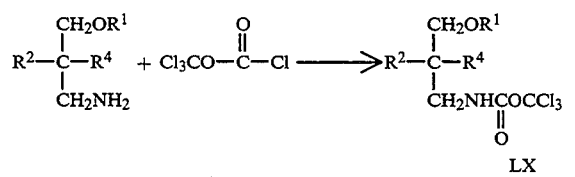

LX

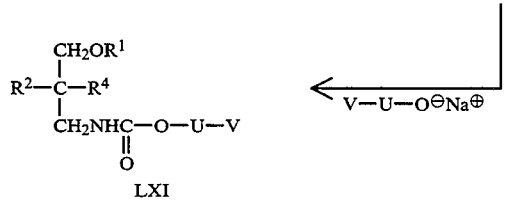

LXI

Compounds LIX and LXI may be alkylated or acylated on the carbamate nitrogen by treating with an appropriate base, such as NaH, followed by a suitable alkyating or acylating agent, such as CH$_3$I and CH$_3$C(O)Cl, respectively.

For preparing compounds of the invention where V is A—B and A represents thioether, an appropriate mercapto compound is treated with strong base to form a sulfur anion. The sulfur anion may then be reacted with a mesylate compound, such as compound XII, causing mesylate displacement.

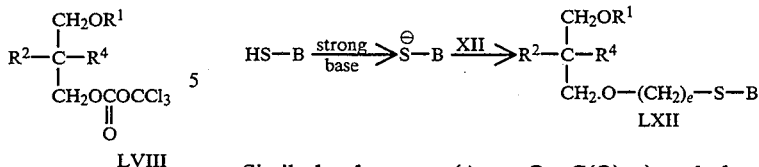

LXII

Similarly the ester (A=—O—C(O)—) and the alkylether (A=—O—(CH$_2$)$_n$—) may be prepared.

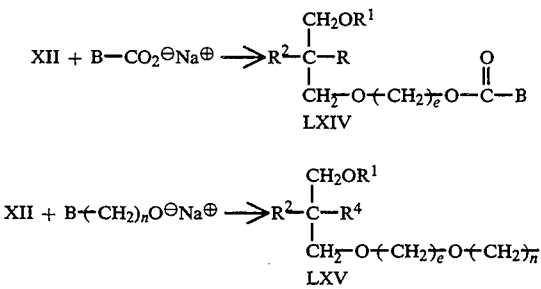

LXIV

LXV

Certain compounds of the invention are prepared from starting materials containing an endo and an exo nitrogen. End products of the invention may therefore contain an exo or endo nitrogen linkage. As used herein, "exo" refers to a nitrogen substituents group, whereas "endo" refers to a nitrogen contained within the ring.

To prepare compounds of the invention where B represents substituted heteroalkyl, the mesylate compound XII is treated with the substituted heteroalkyl containing the desired substitutent, which may be protected, if necessary. The protecting group, if present, is thereafter cleaved to give the compound of the invention.

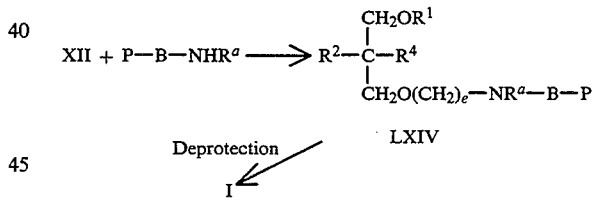

LXIV

I

If B represents heterocycloalkyl which contains an amino group, compounds where A is a direct bond are prepared as described above from the mesylate intermediate.

If B represents a substituted heterocycloalkyl group, the substituent may or may not require protection, and the protected form of B is used to displace the mesylate intermediate. The compound may then be deprotected to form a compound of the invention.

To make a compound where A is a direct bond and B represents

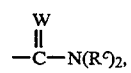

the mesylate intermediate XII is displaced with a cyano compound, which is subsequently treated with an alcohol in the presence of acid to form an imino ester, which is then treated with a primary or secondary amine.

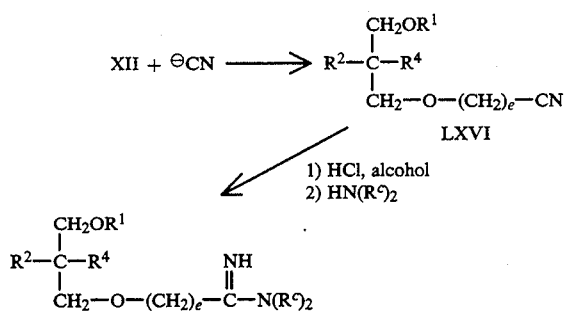

The compounds of the invention possess platelet activating factor ("PAF") antagonistic activity. For example, PAF is an important mediator of such processes as platelet aggregation, smooth muscle contraction (especially in lung tissue), vascular permeability and neutrophil activation. Recent evidence implicates PAF as an underlying factor involved in airway hyperreactivity. The compounds of the invention are therefore useful where PAF is a factor in the disease or disorder. This includes allergic diseases such as asthma, adult respiratory distress syndrome, urticaria and inflammatory diseases such as rheumatoid arthritis and osteoarthritis.

The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF. The in vitro assay is a simple screening test, while the in vivo test mimics clinical use of the compounds described herein.

PAF Antagonism Assay

A. In vitro Assay:

Preparation of platelet-rich plasma (PRP): Human blood (50 ml) was collected from healthy male donors in an anticoagulant solution (5 ml) containing sodium citrate (3.8%) and dextrose (2%). Blood was centrifuged at $110\times$ g for 15 min. and the supernatant (PRP) carefully transferred into a polypropylene tube. Platelet-poor-plasma (PPP) was prepared by centrifuging PRP at $12,000\times$ g for 2 min. (Beckman Microfuge B). PRP was used within 3 hours of drawing the blood.

Platelet Aggregation Assay: When an aggregating agent such as PAF is added to PRP, platelets aggregate. An aggregometer quantifies this aggregation by measuring light transmission through PRP and comparing to PPP. The aggregation assays were performed using a dual channel aggregometer (Model 440, Chrono-Log Corp., Havertown, Penn.). PRP (0.45 ml) in aggregometer cuvettes was continually stirred (37° C). Solutions of test compounds or vehicle were added to the PRP, and after incubation for 2 min., 10-15 $\propto$ I aliquots of PAF solution were added so as to achieve a final concentration of $1-5\times10^{-8}$M. Incubations were continued until the increase in light transmission reached a maximum (usually 2 min). Values for inhibition were calculated by comparing maximal aggregation obtained in the absence and the presence of the compound. For each experiment, a standard PAF antagonist such as alprazolam was used as a positive internal control. The inhibitory concentration ($IC_{50}$) is the concentration of compound in micromoles at which 50% of the aggregation is inhibited, as measured by the light transmission through each sample of PRP as compared to PPP. The test results are shown below in Table A.

TABLE A
PAF-INDUCED PLATELET AGGREGATION $$\begin{array}{c} CH_2-OR^1 \\ R^2-C-R^4 \\ CH_2-R^3 \end{array}$$

| R¹ | R² | R³ | R⁴ | Dose μM | Percent Inhibition | Notes |
|---|---|---|---|---|---|---|
| —C(O)N(CH₃)—C₁₈H₃₇n | —CH₃ | —O—P(=O)(O⁻)—O—(CH₂)₂—N⁺(thiazolium) | —OCH₃ | 5 | 50 | Zwitterionic form |
| —C(O)NH—C₁₈H₃₇n | —CH₃ | —O—P(=O)(O⁻)—O—(CH₂)₂—N⁺(thiazolium) | —OCH₃ | 10 | 50 | Zwitterionic form |
| —C₁₆H₃₃n | —CH₃ | —OCO₂(CH₂)₂N⁺(CH₃)₃ | —OCH₃ | 100 | 100 | iodide salt |
| —C₁₆H₃₃n | —CH₃ | —OCO₂(CH₂)₂—N⁺(pyrrolidinium-CH₃) | —OCH₃ | 50 | 32 | mesylate salt |
| —C(O)N(CH₃)—C₁₈H₃₇n | —CH₃ | —O—P(=O)(O⁻)—O—(CH₂)₂—N⁺(pyridinium) | —OCH₃ | 50 | 43 | zwitterionic form |
| —C(O)N(CH₃)—C₁₈H₃₇n | —CH₃ | —O—(CH₂)₇—N⁺(thiazolium) | —OCH₃ | 50 | 100 | mesylate salt |
| —C(O)N(CH₃)—C₁₈H₃₇n | —CH₂CH₃ | —O—P(=O)(O⁻)—O(CH₂)₂—N⁺(thiazolium) | —OCH₃ | 50 | 100 | Zwitterionic form |
| —C(O)N(CH₃)—C₁₈H₃₇n | —CH₂CH₃ | —O—P(=O)(OH)—O(—CH₂)—N⁺(imidazolium) | —OCH₃ | 50 | 23 | |

TABLE A-continued

PAF-INDUCED PLATELET AGGREGATION $$\begin{array}{c} CH_2-OR^1 \\ R^2-C-R^4 \\ CH_2-R^3 \end{array}$$

| $R^1$ | $R^2$ | $R^3$ | $R^4$ | Dose μM | Percent Inhibition | Notes |
|---|---|---|---|---|---|---|
| —$(CH_2)_{15}CH_3$ | —$CH_3$ | —$OCO_2$—$(CH_2)_2$—$\overset{\oplus}{N}\diagup\!\!\!\diagdown$ (pyridinium) | —$OCH_3$ | 50 | 68 | bromide salt |
| —$\underset{\underset{CH_3}{\|}}{C(O)N}$—$C_{18}H_{37}\underline{n}$ | —$CH(CH_3)_2$ | —$O-\overset{O}{\underset{O^\ominus}{\|}}P-O(CH_2)_2-\overset{\oplus}{N}\diagup\!\!\!\diagdown S$ (thiazolium) | —$OCH_3$ | 50 | 100 | Zwitterionic form |
| —$\underset{\underset{CH_3}{\|}}{C(O)N}$—$C_{18}H_{37}\underline{n}$ | —$CH_3$ | —$O(CH_2)_7-\overset{\oplus}{N}\diagup\!\!\!\diagdown S$ | —$SCH_3$ | 50 | 100 | mesylate salt |
| —$\underset{\underset{CH_3}{\|}}{C(O)N}$—$C_{18}H_{37}\underline{n}$ | —$CH_3$ | —$OC(O)NH(CH_2)_2-\overset{\oplus}{N}(CH_3)_3$ | —$OCH_3$ | 50 | 67 | chloride salt |
| —$\underset{\underset{CH_3}{\|}}{C(O)N}$—$C_{18}H_{37}\underline{n}$ | —$CH_3$ | —$OC(O)NH(CH_2)_2-\overset{\oplus}{N}\diagup\!\!\!\diagdown S$ | —$OCH_3$ | 50 | 97 | iodide salt |
| —$\underset{\underset{CH_3}{\|}}{C(O)N}$—$C_{18}H_{37}\underline{n}$ | —$CH_3$ | —$O-(CH_2)_7-\overset{\oplus}{N}\diagup\!\!\!\diagdown S$ | —$S(O)CH_3$ | 50 | 100 | Mesylate salt |
| —$C_{16}H_{33}\underline{n}$ | —$CH_3$ | —$OC(O)NH(CH_2)_2-\overset{\oplus}{N}\diagup\!\!\!\diagdown S$ | —$OCH_3$ | 50 | 44 | iodide salt |
| —$\underset{\underset{CH_3}{\|}}{C(O)N}$—$C_{18}H_{37}\underline{n}$ | —$CH_3$ | —$O(CH_2)_4-\overset{\oplus}{N}\diagup\!\!\!\diagdown S$ | —$OCH_3$ | 10 | 100 | mesylate salt |

TABLE A-continued
PAF-INDUCED PLATELET AGGREGATION $$\begin{array}{c} CH_2-OR^1 \\ R^2-C-R^4 \\ CH_2-R^3 \end{array}$$

| R¹ | R² | R³ | R⁴ | Dose μM | Percent Inhibition | Notes |
|---|---|---|---|---|---|---|
| —C(O)N—C₁₈H₃₇n<br>  \|<br>  CH₃ | —CH₃ | 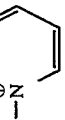 | —OCH₃ | 10 | 100 | chloride salt |
| —C(O)N—C₁₈H₃₇n<br>  \|<br>  CH₃ | —CH₃ |  | —OCH₃ | 50 | 10 | |
| —C(O)N—C₁₈H₃₇n<br>  \|<br>  CH₃ | —CH₃ |  | —OCH₃ | 10 | 93 | iodide salt |
| —C(O)N—C₁₈H₃₇n<br>  \|<br>  CH₃ | —CH₃ |  | —OCH₃ | 10 | 93 | iodide salt |
| —C(O)N—C₁₈H₃₇n<br>  \|<br>  CH₃ | —CH₃ |  | —OCH₃ | 50 | 19 | |
| —C(O)N—C₁₈H₃₇n<br>  \|<br>  CH₃ | —CH₃ |  | —OCH₃ | 50 | 19 | |
| —C(O)N—C₁₈H₃₇n<br>  \|<br>  CH₃ | —CH₃ |  | —OCH₃ | 50 | 3 | |

TABLE A-continued

PAF-INDUCED PLATELET AGGREGATION $$\begin{array}{c} CH_2-OR^1 \\ R^2-C-R^4 \\ CH_2-R^3 \end{array}$$

| $R^1$ | $R^2$ | $R^3$ | $R^4$ | Dose μM | Percent Inhibition | Notes |
|---|---|---|---|---|---|---|
| —C(O)N(CH₃)—C₁₈H₃₇n | —CH₃ | —O—CH₂—C₆H₄—CH₂—N⊕(thiazole) | —OCH₃ | 50 | 100 | mesylate salt |
| —C(O)N(CH₃)—C₁₈H₃₇n | —CH₃ | —O(CH₂)₇—N⊕(thiazole) | —SO₂CH₃ | 50 | 100 | mesylate salt |
| —C(O)N(CH₃)—C₁₈H₃₇n | —CH₃ | —O(CH₂)₇—N⊕(thiazole) | —CH₂CH₃ | 50 | 100 | mesylate salt |
| —C(O)N(CH₃)—C₁₈H₃₇n | —CH₃ | —O(CH₂)₇—O—C(O)—CH(NH₂)—CH₂—SCH₃ | —OCH₃ | 50 | 28 | |
| —C(O)N(CH₃)—C₁₈H₃₇n | —CH₃ | —NHCO₂(CH₂)₂—N⊕(pyridine) | —OCH₃ | 50 | 100 | chloride salt |
| —C(O)N(CH₃)—C₁₈H₃₇n | —CH₃ | —OC(O)NH(CH₂)₅—N⊕(thiazole) | —OCH₃ | 50 | 100 | iodide salt |
| —C(O)N(CH₃)—C₁₈H₃₇n | —CH₃ | —NHCO₂(CH₂)₂N⊕(CH₃)₃ | —OCH₃ | 50 | 83 | iodide salt |
| —C(O)N(CH₃)—C₁₈H₃₇n | —CH₃ | —NHSO₂(CH₂)₂—N(pyridine) | —OCH₃ | 50 | 12 | |

TABLE A-continued

PAF-INDUCED PLATELET AGGREGATION $$R^2-\overset{\overset{\displaystyle CH_2-OR^1}{|}}{\underset{\underset{\displaystyle CH_2-R^3}{|}}{C}}-R^4$$

| R¹ | R² | R³ | R⁴ | Dose μM | Percent Inhibition | Notes |
|---|---|---|---|---|---|---|
| —C(O)N(CH₃)—C₁₈H₃₇n | —CH₃ | —O—(CH₂)₇—[2-amino-imidazolyl] | —OCH₃ | 50 | 17 | |
| phenyl-HNOCO— | H₃C— | —O(CH₂)₇—N⁺[thiazolium] | —OCH₃ | 50 | 100 | CH₃SO₃⁻ salt |
| phenyl-HNOCO— | H₃C— | —OCH₂—(p-C₆H₄)—CH₂—N[2-imino-thiazolidinyl]·HCl | —SO₂CH₃ | 50 | 90 | |
| 2,4-difluorophenyl-HN(O)CO— | H₃C— | —O(CH₂)₇—N[2-imino-thiazolidinyl] | OCH₃ | 50 | 91 | |

PAF is also a known bronchoconstrictive agent in mammals. Hence, PAF antagonism can be evaluated in vivo by measuring inhibition by the compounds of the invention in PAF-induced bronchoconstriction in guinea pigs.

PAF.-Induced Bronchospasm in Guinea Pigs

B. In Vivo Assay

Non-sensitized guinea pigs are fasted overnight, and the following morning are anesthetized with 0.9 ml/kg i.p. of dialurethane (0.1 g/ml of diallybarbituric acid, 0.4 g/ml of ethyl urea and 0.4 g/ml of urethane). The trachea is cannulated and the animals are ventilated by a Harvard rodent respirator at 55 strokes/min. with a stroke volume of 4 ml. A side arm to the tracheal cannula is connected to a Harvard pressure transducer to obtain a continuous measure of intratracheal pressure, which is recorded on a Harvard polygraph. The jugular vein is cannulated for the administration of compounds. The animals are challenged i.v. with PAF (0.4 ug/kg in isotonic saline containing 0.25% BSA) and the peak increase in inflation pressure that occurs within 5 min. after challenge is recorded. Test compounds are administered either orally (2 hrs. prior to PAF as a suspension in 0.4% methylcellulose vehicle) or intravenously (10 min. prior to PAF as a solution in dimethylsulfoxide).

As may be seen from the data in Table A above, the compounds of formula I are effective PAF antagonists useful for the treatment of allergy and inflammation. The methods of treating allergy and inflammation are part of the invention described herein.

When used for the treatment of allergy, the compounds may be administered by any conventional route of administration in an amount ranging from about 0.001 mg/kg to about 100 mg/kg per day, in single or multiple daily doses.

Similarly, when used for the treatment of inflammation, the compounds may be administered by any conventional route of administration in an amount ranging from about 0.001 mg/kg to about 100 mg/kg per day, in single or multiple daily doses.

For preparing pharmaceutical compositions containing a compound of the invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with a carrier having the necessary binding properties in suitable proportions and compacted in the shape and size desired. The powders and tablets may be comprised of from about 5 to about 70 percent active ingredient. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with an encapsulating material a serving as a carrier, thereby providing a capsule in which the active component (with or without other carriers) is surrounded by the carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in polyethylene glycol and/or polypropylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Liquid form preparations may also include solutions for intranasal administration.

Aerosol preparations suitable for inhalation may include solutions and solids in powder form, which may be in combination with a pharmaceutically acceptable carrier, such as an inert compressed gas. Inhalation aerosols may be packaged in a pressure resistant container, which may have a metered dose feature suitable for administration into the oral cavity for inhalation, or into the nasal passageways, thereby delivering a precise amount of aerosol per use.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component, e.g., an effective amount to achieve the desired purpose. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form. The compositions can, if desired, also contain other therapeutic agents.

The quantity of active compound in a unit dose of preparation may be varied or adjusted from about 0.001 mg to 1000 mg, more preferably from about 1 mg to 100 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgement of the attending clinician considering such factors as age, condition and size of the patient as well as severity of the symptom being treated. A typical recommended dosage regimen for oral administration is from 0.25 to 100 mg/day, preferably 10 to 20 mg/day, in two to four divided doses to achieve relief of the symptoms.

Preparative Example 1

DIETHYL-2-ETHYL-2-METHYL MALONATE

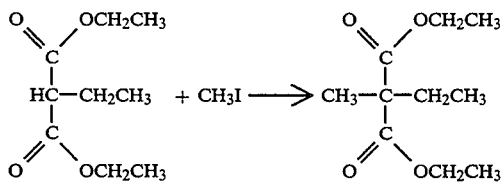

Rapidly add a solution of 2-ethyl-diethylmalonate (71.9 g, 0,382 m) and CH$_3$I (47.7 ml, 108.71 g, 0,766 mol) in CH$_2$Cl$_2$ (370 ml) to a paddle-stirred solution of tetra n-butyl ammonium sulfate (129.88 g, 0.383 mol) and NaOH (30.60 g) in H$_2$O (370 ml) at 25° to 40° C. Stir the system and separate off the CH$_2$Cl$_2$ layer.

Rotavap the CH$_2$Cl$_2$ layer to give a soft solid. Stir the solid with diethyl ether, filter and rotavap the filtrate to give the title compound in the form of an oil.

Stir the oil with diethyl ether (400 ml) and filter off any solids, washing well with diethyl ether. Dry the filtrate and washings over Na$_2$SO$_4$ and rotavap. High vac dry for 18 hours to yield the title compound as a yellow oil.

Preparative Example 2

2-METHYL-2-ETHYLPROPANE-1.3-DIOL

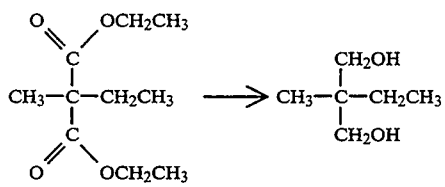

Cautiously add a solution of diethyl-2-ethyl-2-methyl malonate (106.8 g, 0.528 mol) in diethyl ether (400 ml) portionwise to a paddle stirred suspension of lithium aluminum hydride (32.71 g, 0.862 mol) in dry diethyl ether (1.4 l) at 22° to 30° C. under a N$_2$ atmosphere. Stir for 20 minutes at room temperature, then reflux for three hours under N$_2$.

Add Na$_2$SO$_4$.10H$_2$O (100 g) over 45 minutes at 20° to 25° C. while under a N$_2$ atmosphere with vigorous stirring. Continue stirring for 18 hours to form the title compound as a white suspension.

Filter the suspension and wash the filter cake with diethyl ether. Rotavap the filtrate and washings, and high vac dry to give the title compound as a soft, wax-like solid.

Preparative Example 3

DIETHYL-2-METHYL-2-METHYLTHIOMALONATE

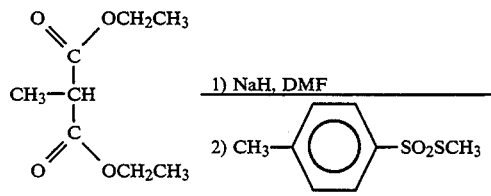

Wash Nail (8.92 g, 0.223 mol) three times with hexanes and once with DMF (230 ml) and place in a 2-liter 3-neck round bottom flask, equipped with a thermometer, dropping funnel, mechanical stirrer and N$_2$ inlet/outlet. Add a solution of diethyl methyl malonate (35.26 g, 0.202 mol) in DMF (108 ml) dropwise over approximately 30 minutes while under nitrogen. Stir for 30 minutes at room temperature and add a solution of methyl thiotosylate (40.93 g, 0.202 mol) in dry DMF (68 ml) dropwise over 7 minutes at 20° to 25° C. to form a suspension. Stir for 64 hours at room temperature.

Add H$_2$O (125 ml) to the reaction at 22° to 28° C. under N$_2$. Pour the reaction mixture into H$_2$O (1.2 l) and diethyl ether (300 ml) and stir. Saturate the aqueous layer with NaCl. Separate and extract the aqueous layer with diethyl ether (3×150 ml). Combine the ether layers and wash with H$_2$O (4×100 ml) and brine (1×180 ml). Dry over Na$_2$SO$_4$ and rotavap to give the title compound as a clear yellow oil.

Preparative Example 4

2-METHYLTHIO-2-METHYLPROPANE-1,3-DIOL

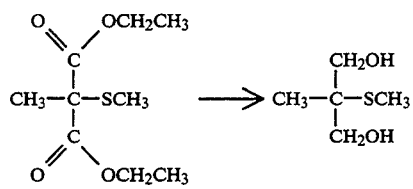

Substitute the title compound of Preparative Example 3 for the 2-ethyl compound in the reaction described in Preparative Example 2 to make the title compound, in the form of a viscous, clear, faintly yellow oil.

Preparative Example 5

2-METHYL-2-PROPENYL-N-OCTADECYLCARBAMATE

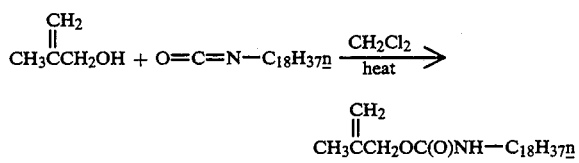

Reflux a mixture of 2-methyl-2-propen-1-ol (23.8 g, 0.331 mole), n-octadecyl isocyanate (88.7 g, 0.3 mol), and methylene chloride (300 ml) for 18 hours. Remove volatiles under reduced pressure and triturate the residual solid thoroughly with acetone (250 ml) at room temperature. Filter to obtain the title compound as a white powder (m.p. 61.5°–62.5° C.).

Preparative Example 6

3-(N-OCTADECYLCARBAMOYL)-2-METHYL GLYCEROL

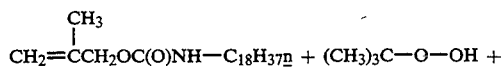

CH$_2$=CCH$_2$OC(O)NH—C$_{18}$H$_{37}$n + (CH$_3$)$_3$C—O—OH +

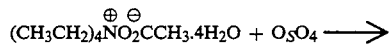

(CH$_3$CH$_2$)$_4$⊕NO$_2$CCH$_3$.4H$_2$O + O$_5$O$_4$ ⟶

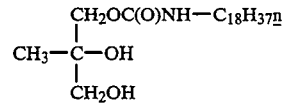

Dissolve osmium tetroxide (3.0 g, 0.0118 m) in t-butyl hydroperoxide (3 ml) and t-butanol (597 ml). Suspend the title compound of Preparative Example 5 (285 g, 0.775 m) and t-butyl hydroperoxide (382 ml, 2.79 m) along with tetraethyl ammonium acetate tetrahydrate (57.1 g, 0.247 m) in acetone (5.7 L) and cool to 0° C. . Add the osmium solution over a period of about 10 minutes. Stir in an ice bath for 2 hours, then at room temperature for 48 hours.

Cool to 0° C., and add a solution of NaHSO$_3$ in water (794 g in 4.41 L) dropwise, maintaining the temperature at 0° C. to 5° C.

Filter off a brownish precipitate, wash the precipitate with water, dissolve in CH$_2$Cl$_2$ (6.08 L)/CH$_3$OH(3.04 L), and wash. Remove solvent and suspend the residue in diethyl ether (1 L). Filter, wash with diethylether, and dry to obtain the title compound as a white solid (m.p. 89.5°–90.5° C.).

Preparative Example 7

Substitute the compound shown in column one of the Table below for 2-methyl-2-propen-1-ol in the procedure described in Preparative Example 5 above to make the product shown in column two.

TABLE

| Reactant | Product |
|---|---|
| CH$_3$—C(CH$_2$OH)(CH$_2$CH$_3$)—CH$_2$OH | CH$_3$—C(CH$_2$—OC(O)NH—C$_{18}$H$_{37}$n)(CH$_2$CH$_3$)—CH$_2$OH |
| CH$_3$—C(CH$_2$OH)(SCH$_3$)—CH$_2$OH | CH$_3$—C(CH$_2$—OC(O)NH—C$_{18}$H$_{37}$n)(SCH$_3$)—CH$_2$OH |
| CH$_3$CH$_2$—C(=CH$_2$)—CH$_2$OH | CH$_3$CH$_2$—C(=CH$_2$)—CH$_2$OC(O)NH—C$_{18}$H$_{37}$n |
| (CH$_3$)$_2$CH—C(=CH$_2$)—CH$_2$OH | (CH$_3$)$_2$CH—C(=CH$_2$)—CH$_2$OC(O)NH—C$_{18}$H$_{37}$n |

Preparative Example 8

Substitute an appropriate reactant olefin disclosed in the Table below into the process of Preparative Example 6 to make the diol shown in column two.

TABLE

| Reactant | Product |
|---|---|
| $CH_3CH_2-\underset{\|}{\overset{CH_2}{C}}-CH_2OC(O)NH-C_{18}H_{37}\underline{n}$ | $CH_3CH_2-\underset{\underset{CH_2OH}{\|}}{\overset{\overset{CH_2-OC(O)NH-C_{18}H_{37}\underline{n}}{\|}}{C}}-OH$ |
| $(CH_3)_2CH-\underset{\|}{\overset{CH_2}{C}}-CH_2OC(O)NH-C_{18}H_{37}\underline{n}$ | $(CH_3)_2CH-\underset{\underset{CH_2OH}{\|}}{\overset{\overset{CH_2-OC(O)NH-C_{18}H_{37}\underline{n}}{\|}}{C}}-OH$ |

Preparative Example 9
1-O-(p-ANISYLDIPHENYL)METHYL-2-METHYL-3-(N-OCTADECYLCARBAMOYLY)-GLYCEROL $CH_3-\underset{\underset{CH_2OH}{\|}}{\overset{\overset{CH_2OC(O)NH-C_{18}H_{37}\underline{n}}{\|}}{C}}-OH$ +

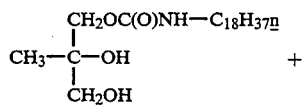

$\xrightarrow{\text{N}}$

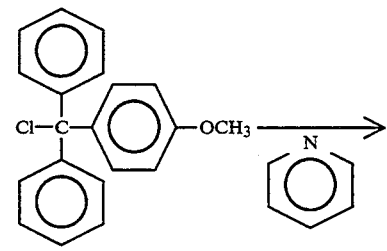

-continued

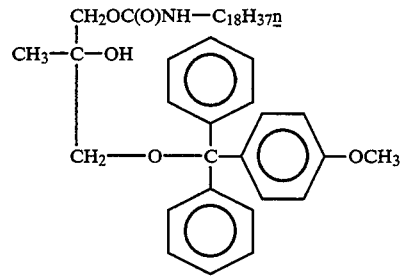

Dissolve the title compound of Preparative Example 6 in pyridine (4.05 L) and add p-anisylchlorodiphenylmethane (277 g, 0.397 m). Stir at room temperature until the reaction is complete, as monitored by TLC.

Remove pyridine under reduced pressure. Dissolve the residue in $CH_2Cl_2$ (3.4 L) and wash with $H_2O$ (twice) and saturated NaCl solution (1.5 L). Dry over $Na_2SO_4$, filter and strip the solvent from the filtrate.

Dissolve the residue in hexane, and chromatograph on silica gel, eluting with hexaneethylacetate (4:1). Combine the appropriate fractions, and concentrate under reduced pressure to obtain the title compound as an off-white solid (68°–70° C.).

Preparative Example 10

Substitute the appropriate 2,3-diol from Preparative Examples 6 and 8 into the reaction described in Preparative Example 9 above to form the 3-protected hydroxy compound shown below in the table.

TABLE

| Reactant | Product |
|---|---|
| $CH_3CH_2-\underset{\underset{CH_2-OH}{\|}}{\overset{\overset{CH_2-OC(O)NH-C_{18}H_{37}\underline{n}}{\|}}{C}}-OH$ | $CH_3CH_2-\underset{\underset{CH_2O-\text{Tr(OMe)}}{\|}}{\overset{\overset{CH_2-OC(O)NH-C_{18}H_{37}\underline{n}}{\|}}{C}}-OH$ |

TABLE-continued

| Reactant | Product |
|---|---|
| (CH₃)₂CH—C(CH₂—OC(O)NH—C₁₈H₃₇ⁿ)(CH₂—OH)—OH | (CH₃)₂CH—C(CH₂—OC(O)NH—C₁₈H₃₇ⁿ)(CH₂—O—C(Ph)₂(C₆H₄—OCH₃))—OH |
| CH₃—C(CH₂—OC(O)NH—C₁₈H₃₇ⁿ)(CH₂CH₃)—CH₂—OH | CH₃—C(CH₂—OC(O)NH—C₁₈H₃₇ⁿ)(CH₂CH₃)—CH₂—O—C(Ph)₂(C₆H₄—OCH₃) |

Preparative Example 11

3-(N-METHYL-N-OCTADECYLCARBAMOYL)-2-METHYL-2-METHOXY-GLYCEROL

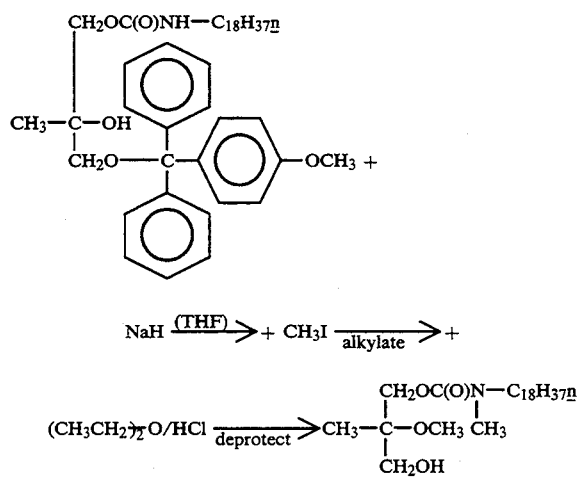

Alkylation Step

Rinse NaH with petroleum ether, and suspend NaH in tetrahydrofuran ("THF") (520 ml). Dissolve the title compound of Preparative Example 9 above in THF (2.07 l), and add this solution by steady stream over 0.5 hours to the NaH solution. Add THF (1.38l) and stir at room temperature for 2.5 hours. Add dropwise a solution of CH₃I (239 ml) in THF (690 ml). Stir at room temperature, and monitor the reaction progress by TLC (hexane-ethyl acetate; 4:1) until starting materials are absent.

Deprotection Step

Cool the reaction mixture to −5° C., and add ethereal hydrochloric acid (648 ml) dropwise over 45 minutes. Stir at −5° C. for 0.5 hrs., and monitor reaction progress as before with TLC until the starting material is absent. Concentrate to a residue at room temperature under vacuum. Dissolve the residue in CH₂Cl₂ (3.5 L) and wash with H₂O (4×, 2.3 L), then with saturated NaCl solution (2.3 L).

Dry over MgSO₄, filter, wash and strip off the solvent to yield a reddish-amber syrup. Chromatograph on silica gel. Elute with CH₂Cl₂ to eliminate less polar impurities at the solvent front, then elute successively with hexane-ethyl acetate (4:1) and hexane-ethyl acetate (2:1). Concentrate the appropriate fractions at room temperature to yield the title compound as a red-orange solid.

Preparative Example 12

Substitute the reactant shown in column 1 of the Table below for 1—O—(p-anisyl diphenyl)methyl-2-methyl-3-(N-octadecylcarbamoyl)glycerol in the reaction described in Preparative Example 11 to prepare the product shown in column 2 below.

TABLE

| Reactant | Product | Notes |
|---|---|---|
| CH₃—C(CH₂—OC(O)NH—C₁₈H₃₇ⁿ)(CH₂CH₃)—CH₂—O—C(Ph)₂(C₆H₄—OCH₃) | CH₃—C(CH₂—OC(O)N(CH₃)—C₁₈H₃₇ⁿ)(CH₂CH₃)—CH₂—O—C(Ph)₂(C₆H₄—OCH₃) | Alkylation Step. Product in the form of an oil. |

| Reactant | Product | Notes |
|---|---|---|
| (structure) | (structure) | Deprotection Step Reactant obtained in previous step. Product in the form of an oil. |
| (structure) | (structure) | Selective Alkylation with stoichiometric addition of CH₃I. Deprotect with HCl and dioxane or with H₂ and Pd on carbon (10%). |

Preparative Example 13

3-[7-[[(1,1-DIMETHYLETHYL)DIMETHYL-SILYL]OXY]HEPTYLOXY]-2-METHOXY-2-METHYLPROPYL-N-METHYLOCTADECYL-CARBAMATE

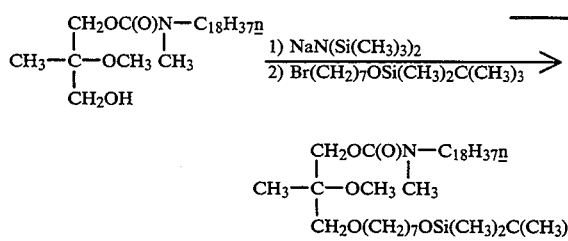

Dissolve the title compound of Preparative Example 11 in DMF (300 ml) and add NaN(Si(CH$_3$)$_3$)$_2$ (110 ml, 1.0M) in THF with stirring over 8 minutes at 18° C. under a N$_2$ atmosphere. Stir at 18° C. for 1.5 hours, then add a solution of Br(CH$_2$)$_7$OSi(CH$_3$)$_2$C(CH$_3$)$_3$ (34.0 g, 0.11 mmoles) in DMF (100 ml) at 18°–22° C. Stir for 1 hr. at room temperature, then heat to 50° C. for 18 hrs. Partition the sample between H$_2$O-diethyl ether.

Concentrate the ether extract on a rotary evaporator. Partition the residue between CH$_2$Cl$_2$ (500 ml) and H$_2$O (250 ml) and separate off the "milky layer". Extract the aqueous layer with CH$_2$Cl$_2$ (2×250 ml) and combine the organic layers. Wash with H$_2$O (2×150 ml), dry the CH$_2$Cl$_2$ solution over Na$_2$SO$_4$, filter and strip the solvent from the filtrate under reduced pressure. Hi-vac dry to give the title compound as a dark amber oil.

Preparative Example 14

Substitute the reactant shown in column 1 of the Table below for 3-(N-methyl-N-octadecylcarbamoyl)-2-methyl-2-methoxy glycerol in Preparative Example 13 to make the product shown in column two.

TABLE

| Reactant | Product |
|---|---|
| (structure) | (structure) |
| (structure) | (structure) |

Preparative Example 15

3-[7-(HYDROXY)HEPTYLOXY]-2-METHOXY-2-METHYLPROPYL-N-METHYLOCTADECYL-CARBAMATE

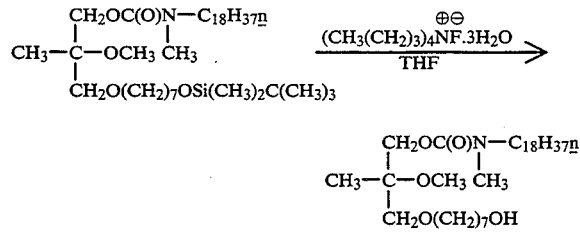

Dissolve the title compound of Preparative Example 13 (59.84 g, 0.091 mole max.) in THF. Add (CH$_3$(CH$_2$)$_3$)$_4$NF.3H$_2$O in 3 portions over 10 minutes at 15°–18° C. Stir at room temperature under a N$_2$ atmosphere for 3 hrs., and partition between H2O and diethyl ether.

Monitor reaction progress in the ether layer by TLC.

Concentrate the reaction mixture under reduced pressure and dissolve the residual dark oil in $CH_2Cl_2$ (300 ml). Wash (3×) with $H_2O$, dry over $MgSO_4$, filter and rotovap filtrate to 150–200 ml. Purify with flash chromatography on silica gel to yield the title compound.

Preparative Example 16

Substitute a reactant shown below in column 1 of the Table below for 3-[7-[[(1,1-dimethylethyl)-dimethylsilyl]oxy]heptyloxy-2-methoxy-2-methyl propyl]-N-methyloctadecyl carbamate in Preparative Example 15 ml) at 5° to 7° C. Stir for 15 min. and warm to room temperature. Dilute with diethyl ether (2×sample volume) after 2 hours, and monitor reaction progress by TLC. If necessary, dilute further with diethyl ether (150 ml), filter off $(CH_3CH_2)_3N.HCl$, and rotavap filtrate. High vac dry and purify the sample by flash chromatography as necessary to give the title compound as a viscous, slight amber oil.

Preparative Example 18

Substitute a reactant from column 1 of the Table below for 3-[7-(hydroxy)heptyloxy]-2-methoxy-2-methylpropyl-N-methyloctadecylcarbamate in Preparative Example 17 to make the product shown in column 2 below.

TABLE

| Reactant | Product |
|---|---|
| $\begin{array}{c}CH_2-OC(O)N-C_{18}H_{37}\underline{n}\\|\quad\quad\quad\quad\quad\quad\quad|\\CH_3-C-CH_2CH_3\ CH_3\\|\\CH_2-O(CH_2)_7-OH\end{array}$ | $\begin{array}{c}CH_2-OC(O)N-C_{18}H_{37}\underline{n}\\|\quad\quad\quad\quad\quad\quad\quad|\\CH_3-C-CH_2CH_3\ CH_3\\|\\CH_2-O(CH_2)_7OSO_2CH_3\end{array}$ |
| $\begin{array}{c}CH_2-OC(O)N-C_{18}H_{37}\underline{n}\\|\quad\quad\quad\quad\quad|\\CH_3-C-SCH_3\quad CH_3\\|\\CH_2-O(CH_2)_7OH\end{array}$ | $\begin{array}{c}CH_2-OC(O)N-C_{18}H_{37}\underline{n}\\|\quad\quad\quad\quad\quad|\\CH_3-C-SCH_3\quad CH_3\\|\\CH-O(CH_2)_7OSO_2CH_3\end{array}$ | to make the compound shown in column 2 below.

TABLE

| Reactant | Product |
|---|---|
| $\begin{array}{c}CH_2-OC(O)-N-C_{18}H_{37}\underline{n}\\|\quad\quad\quad\quad\quad\quad|\\CH_3-C-CH_2CH_3\ CH_3\\|\\CH_2-O(CH_2)_7-OSi(CH_3)_2C(CH_3)_3\end{array}$ | $\begin{array}{c}CH_2-OC(O)N-C_{18}H_{37}\underline{n}\\|\quad\quad\quad\quad\quad\quad|\\CH_3-C-CH_2CH_3\ CH_3\\|\\CH_2-O(CH_2)_7OH\end{array}$ |
| $\begin{array}{c}CH_2-OC(O)N-C_{18}H_{37}\underline{n}\\|\quad\quad\quad\quad\quad|\\CH_3-C-SCH_3\quad CH_3\\|\\CH_2-OSi(CH_3)_2C(CH_3)_3\end{array}$ | $\begin{array}{c}CH_2-OC(O)N-C_{18}H_{37}\underline{n}\\|\quad\quad\quad\quad\quad|\\CH_3-C-SCH_3\quad CH_3\\|\\CH_2OH\end{array}$ |
| $\begin{array}{c}CH_2-OC(O)N-C_{18}H_{37}\underline{n}\\|\quad\quad\quad\quad\quad|\\CH_3-C-SCH_3\quad CH_3\\|\\CH_2-O(CH_2)_7OSi(CH_3)_2C(CH_3)_3\end{array}$ | $\begin{array}{c}CH_2-OC(O)N-C_{18}H_{37}\underline{n}\\|\quad\quad\quad\quad\quad|\\CH_3-C-SCH_3\quad CH_3\\|\\CH_2-O(CH_2)_7OH\end{array}$ |

Preparative Example 17

3-[7-[(METHANESULFONYL)OXY]HEPTYLOXY]-2-METHOXY-2-METHYLPROPYLMETHYLOCTADECYL CARBAMATE

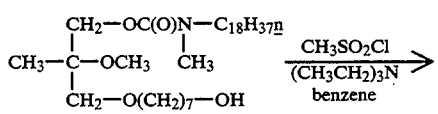
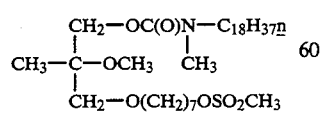

Add a solution of methanesulfonyl chloride (0.94 g, 8.2 mmoles) in dry benzene (18 ml) to a stirred solution of 3-[7-(hydroxy)heptyloxy]-2-methoxy-2-methylpropyl methyl octadecylcarbamate (4.26 g, 17.8 mmoles) and triethylamine (0.83 g, 8.2 mmoles) in benzene (38

Preparative Example 19

3-(N-METHYL)OCTADECYLCARBAMOYLOXY-2-METHOXY-2-METHYLPROPYL-2-BROMOETHYLPHOSPHATE

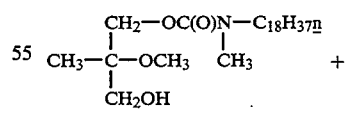
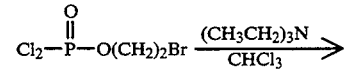
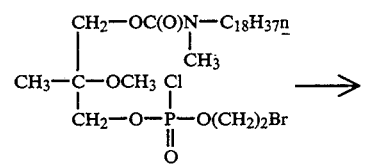

-continued

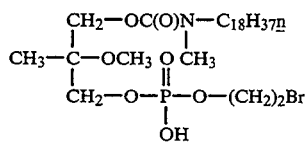

Step 1

Dissolve 2-bromoethyl phosphochloridate (2.60 g) in CHCl$_3$ (10 ml) and add dropwise to a mixture of 3-hydroxy-2-methoxy-2-methyl propyl-N-methyloctadecylcarbamate (2.16 g) and triethylamine (2.79 ml) in CHCl$_3$ (50 ml) at 0° C. After complete addition, allow the reaction to come to room temperature, and stir at room temperature for 24 hours. Rotavap in vacuo to give a brown semi solid. Stir with excess diethyl ether and filter. Concentrate the filtrate to give a dark brown oil.

Step 2

Boil the end product of step 1 above in H$_2$O (100 ml) and THF (150 ml) for 2 hours. Cool the reaction to room temperature and dilute with diethyl ether. Separate off the ether layer, and extract the aqueous layer repeatedly (3×60 ml). Combine the ether extracts and dry over Na$_2$SO$_4$. Filter and rotavap in vacuo to give an oil. Redissolve the oil in CHCl$_3$, dry over Na$_2$SO$_4$, filter and rotavap. Dry in vacuo to yield the title compound as a brown oil.

Preparative Example 20

1-BROMOETHYL-4-[(1,1-DIMETHYLETHYL)-DIMETHYL SILYL]OXYMETHYLBENZENE

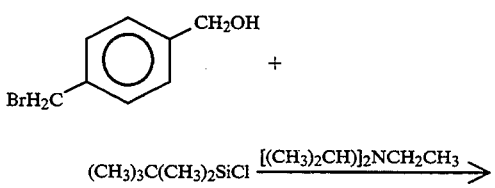

Stir 1-bromomethyl-4-hydroxymethyl benzene (20.75 g) in CH$_2$Cl$_2$ (300 ml) with diisopropylethylamine (14.01 g) at 18° C., and add a solution of t-butyl dimethylsilyl chloride (16.34 g) in CH$_2$Cl$_2$ (100 ml). Stir for one half hour at room temperature, then reflux for 19 hours under a N$_2$ atmosphere. Monitor reaction progress by TLC.

Rotavap the solution at 30° C., and stir the residual soft solids with hexanes (350 ml). Filter off the solids, washing with hexanes as appropriate. Rotavap the filtrate and washings at 35° C. to give the title compound in crude form as a reddish oil.

Preparative Example 21

3-[[4-(1,1-DIMETHYLETHYL)DIMETHYLSILYL-]OXYMETHYL PHENYLMETHOXY]-2-METHOXY-2-METHYL-PROPYL N-METHYLOCTADECYLCARBAMATE

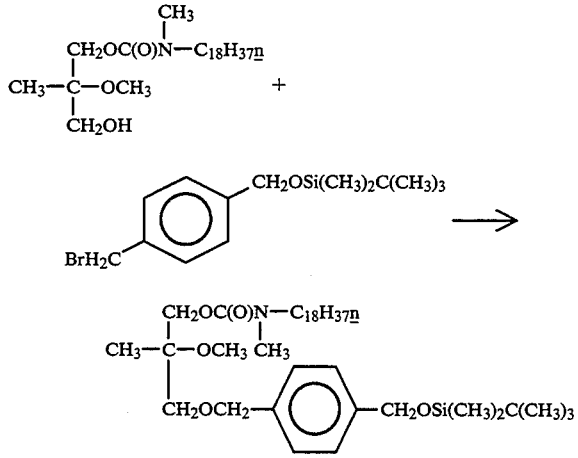

Add a solution of sodium bis(trimethylsilyl)amide (46.5 ml, 1.0M) in THF at 22° to 24° C. to a stirred solution of the title compound of Preparative Example 11 in dry dimethylformamide ("DMF") (240 ml) under a N$_2$ atmosphere. Stir for 1.5 hours at room temperature. Add a solution of the title compound of Preparative Example 20 in DMF (20 ml) at 21° to 23° C., stir for 1 hour at room temperature, then heat to 50° C. and maintain for 3 hours.

Partition the sample between H$_2$O and diethyl ether and monitor reaction progress in the ether layer by TLC.

Concentrate the reaction on a rotavap and stir the residue in diethyl ether (400 ml). Filter through a 3 inch column of Celite. Rotavap the filtrate to give the title compound as an amber oil.

Preparative Example 22

3-[4-(HYDROXYMETHYL)PHENYLMETHOXY]-2-METHOXY-2-METHYLPROPYL-N-METHYLOCTADECYLCARBAMATE

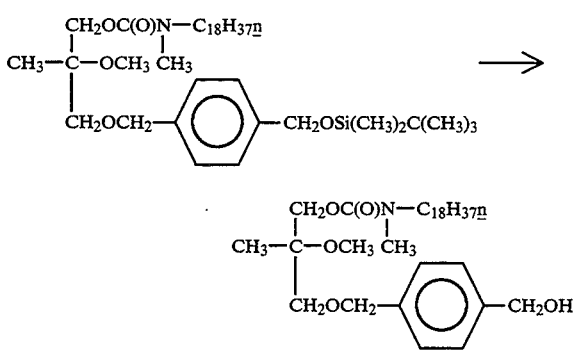

Stir the title compound of Preparative Example 21 (31.89 g) in THF (250 ml), and while cooling in a water bath, add tetrabutylammonium fluoride.3H$_2$O rapidly. Continue stirring under a N$_2$ atmosphere for 2 hours at room temperature.

Concentrate on the rotavap, partition between H$_2$O and diethyl ether (120 ml:150 ml) and separate. Extract the aqueous layer with diethyl ether (2×) and dry the combined ether extracts over Na$_2$SO$_4$. Filter and rotavap the filtrate. Dry the residue under vacuum to obtain a crude form of the title compound as a viscous oil.

The crude product may be purified by flash chromatography on silica gel, eluting with acetonemethylene chloride (1:9).

Preparative Example 22A

1-HYDROXY-2-METHYL-2--METHYLTHIO-3-(N-METHYL-N-OCTADECYL-CARBAMOYLOXY)PROPANE

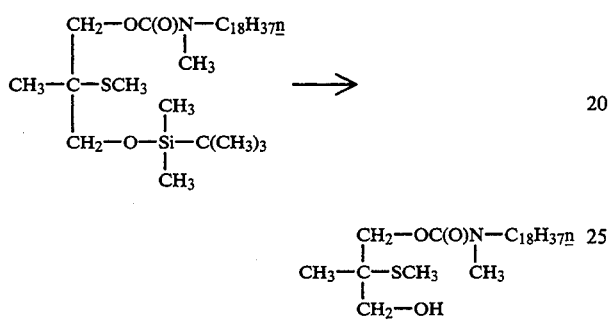

Substitute the 3-protected alcohol in the reaction described in Preparative Example 22 to obtain the title compound.

Preparative Example 23

3-[4-[(METHYLSULFONYL)OXYMETHYL]-PHENYLMETHOXY]-2-METHOXY-2-METHYL-PROPYL-N-METHYLOCTADECYL CARBAMATE

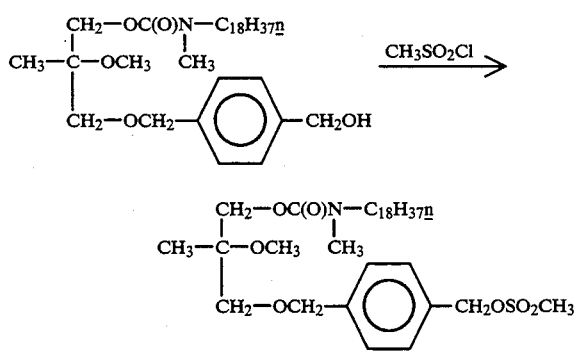

Add a solution of CH$_3$SO$_2$Cl (0.75 ml, 1.11 g) in benzene (20 ml) to a stirred solution of the title compound of Preparative Example 22 and (CH$_3$CH$_2$)$_3$N (1.35 ml, 0.98 g) in benzene (50 ml) at 10°–12° C. Gradually warm to room temperature and stir for 2.5 hours to obtain the title compound.

After 2.5 hours at room temperature, dilute the reaction mixture with diethyl ether (200 ml) and filter off the side product, (CH$_3$CH$_2$)$_3$N.HCl, through Celite. Rotavap the filtrate and high vac dry the residue to obtain the title compound in crude form as a viscous oil.

To purify, flash chromatograph the crude product on silica gel, eluting with acetone-methylene chloride (5:95).

Preparative Example 24

1-(N-METHYLOCTADECYL)CARBAMOYLOXY-2-METHOXY-2-METHYL-3-(N-(2-CHLOROETHYL)AMINOCARBONYLOXY)PROPANE

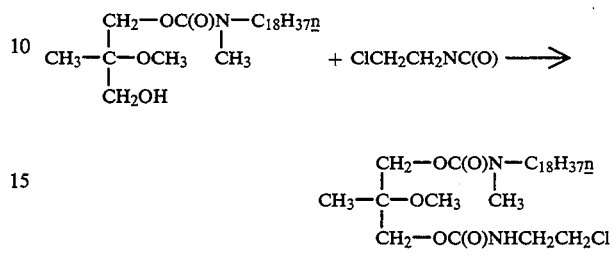

Combine the title compound of Preparative Example 11 with β-chloroethylisocyanate (0.74 g, 7 mmol) and pyridine (30 ml) and stir at room temperature for 17 hours. Add diethyl ether (100 ml) and wash with ice water (2×100 ml) and cold, dilute HCl (3×100 ml). Dry over MgSO$_4$, filter and concentrate to a colorless oil (2.6 g) which is a crude form of the title compound.

Dissolve the crude product in pyridine (40 ml), add β-chloroethylisocyanate (0.5 ml) and stir at room temperature for 66 hours. Add diethyl ether (100 ml) and wash with ice water (3×100 ml) and cold dilute HCl (2×100 ml). Dry over MgSO$_4$, filter and concentrate to obtain the title compound as a colorless oil.

By substituting an alternative starting material for ClCH$_2$CH$_2$NC(O), such as Cl(CH$_2$)$_5$NC(O), longer alkyl chain analogs may be prepared.

Preparative Example 25

1-(N-METHYLOCTADECYL)CARBAMOYLOXY-2.-METHOXY-2-METHYL-3-N-(2-IODOETHYL-)AMINOCARBONYLOXYPROPANE

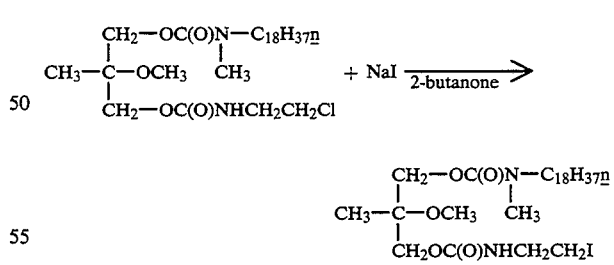

Combine the title compound of Preparative Example 24 (1.0 g), NaI (0.8 g) and 2-butanone (15 ml), and reflux under a N$_2$ atmosphere for 17 hours. Filter off the resulting white solid and rinse with diethyl ether. Concentrate to dryness to obtain a viscous orange oil. Chromatograph the orange oil on silica gel, eluting with ethyl acetate-CH$_2$Cl$_2$ (2:98), to obtain the title compound as a yellow oil, which solidifies to a yellow solid over time.

Preparative Example 26

1-(OCTADECYL-N-METHYL)CARBAMOYLOXY-2-METHOXY-2-METHYL-3-[(N-2-CHLOROETHYL-N-ACETYL)AMINOCARBONYLOXY)]PROPANE

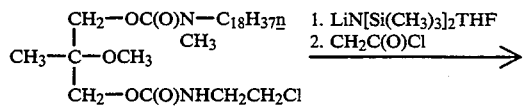

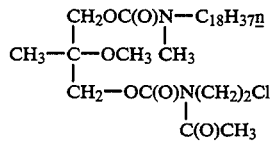

Dissolve the title compound of Preparative Example 24 (0.8 g, 1.5 mmol) in THF (10 ml) under a $N_2$ atmosphere, cool to $-75°$ C. with acetone and dry ice, and add $LiN(Si(CH_3)_3)_2$ (2 ml). Stir at $-78°$ C. for 15 minutes.

Add $CH_3C(O)Cl$ (0.5 ml) via a syringe and stir at $-78°$ C. for about 24 hours. Add a saturated solution of $NaHCO_3$ (20 ml) and stir for 10 minutes. Extract with diethyl ether (50 ml) and wash successively with diethyl ether, saturated $NaHCO_3$ (20 ml) and $H_2O$ (30 ml).

Dry over $MgSO_4$, filter and concentrate to yield the title compound as a yellowish oil (1.0 g). Monitor purity with TLC using ethyl acetate-$CH_2Cl_2$ (1:4).

To further purify, chromatograph the crude product on silica gel, eluting with ethyl acetate-$CH_2Cl_2$(1:9).

Preparative Example 27

1-n-HEXADECYLOXY-2-METHYL-2-PROPENE

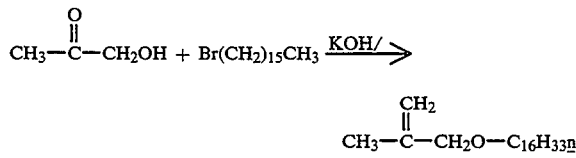

Add hexadecyl bromide (20.99 g), 3-hydroxy-2-methyl propene (20.85 g), KOH (14.4 g) and $(CH_3(CH_2)_3)_4NI$ to dry benzene (200 ml) and heat to reflux, maintaining the reaction under an argon atmosphere with slight positive pressure by balloon. Monitor reaction progress by TLC, using hexane-diethyl ether (9:1).

Cool the reaction and add diethyl ether (75 ml). Wash with 1N HCl (2×100 ml), saturated $NaHCO_3$ (1×150 ml) and brine (2×100 ml). Dry over $Na_2SO_4$.

Filter and distill the filtrate to obtain the title compound as a waxy solid (b.p. 182°–185° C.).

Preparative Example 28

2-(n-HEXADECYLOXYMETHYL)-2-METHYLOXIRANE

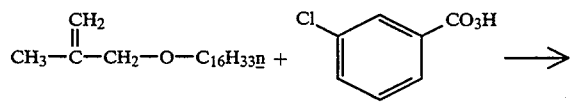

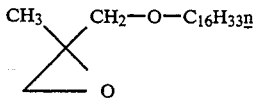

Dissolve the title compound of Preparative Example 27 (9.49 g) in $CH_2Cl_2$ (200 ml) and add m-chloroperbenzoic acid (6.90 g) in portions over 5 min. Monitor reaction progress by TLC using ethyl acetate-hexanes (1:9).

When reaction is complete, wash the reaction solution with saturated $NaHCO_3$ (2×200 ml), then stir the $CH_2Cl_2$ solution in aqueous 10% $NaHSO_3$ for 20 minutes to form a cloudy white precipitate in the organic layer. Wash the organic layer with saturated $NaHCO_3$ (1 ×200 ml), then with NaOH (1N, 2×200 ml) to remove the precipitate. Dry the $CH_2Cl_2$ solution over $MgSO_4$, filter and concentrate the filtrate to obtain the title compound as a clear oil.

Preparative Example 29

2-METHYL-2-PROPENYL-N-METHYL-N-(OCTADECYLCARBAMATE

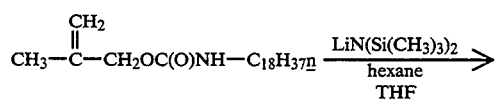

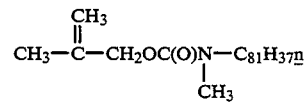

Stir a solution of the title compound of Preparative Example 5 (18.0 g, 49.0 mmol) in THF (90 ml) and add dropwise over 25 min. lithium bis(trimethylsilyl)amide (1M, 54 ml) in hexane. Stir the resultant yellow suspension under an inert atmosphere for 25 min, and add dropwise $CH_3I$ (7.67 g, 54.0 mmol) in THF (15 ml) over 10 min. Stir at room temperature for 25 hours. Add aqueous $NH_4Cl$ (2 ml, 6M), then $CH_2Cl_2$ (50 ml). Filter through a pad of silica gel, and wash the pad with $CH_2Cl_2$ (50 ml).

Combine the filtrate and washings and remove the solvent under reduced pressure to yield a residual yellow oil. Chromatograph the residual yellow oil on silica gel, eluting with ethyl acetate-petroleum ether in a stepped gradient (1:24 followed by 1:9) to yield the title compound as an oil.

$^1$H NMR ($CDCl_3$; δ-values relative to internal TMS): 5.00 (br s, 1H), 4.94(br s, 1H), 4.53(s, 2H), 3.29 (br t, 2H), 2.94(s, 3H), 1.78(s, 3H), 1.15–1.6 (complex m, 32H), 0.92(t, 3H). Mass Spectrum (electron impact): 382[(M+1)+: 100%], 381[M+; 41%]

Preparative Example 30

N-METHYL-N-(OCTADECYL CARBAMIC ACID. [(2-METHYL-2-OXIRANYL)METHYL]ESTER

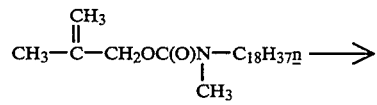

-continued

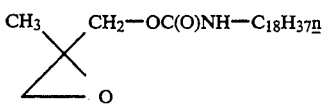

Substitute the title compound of Preparative Example 29 for O-(n-hexadecyloxy)-2-methyl-2-propene in Preparative Example 28 and treat with m-chloroperbenzoic acid as described therein to obtain the title compound as a colorless oil which solidifies upon standing at room temperature.

$^1$H NMR (CDCl$_3$): δ4.25 (d, J=12.5 Hz, 1H), 3.96(d, J=12.5 Hz, 1H), 3.26 (t; J=7.5 Hz, 2H), 2.90 (s, 3H), 2.78 (d, J=5 Hz, 1H), 2.68 (d, J=5 Hz, 1H), 1.52 (m, 2H), 1.38 (s, 3H), 1.26 (m, 30H), 0.88 (t, 3H). MS (FAB): 398 [(M+1)+; 100%], 310 (22%), 284 (43%).

Preparative Example 31

1-HEXADECYLOXY-2-METHYL-8-METHOXY GLYCEROL

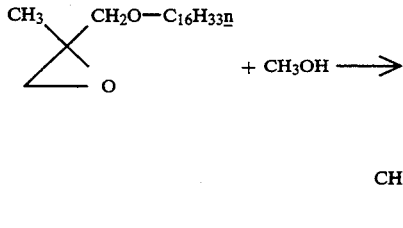

Stir the title compound of Preparative Example 28 in CH$_3$OH (150 ml), cool to 0° C. and add p-toluene-sulfonic acid (200 mg). Monitor reaction progress by TLC using ethyl acetate-hexanes (1:3).

Concentrate in vacuo and add CHCl$_3$ (200 ml). Wash with NaHCO$_3$ (10%, 3×50 ml), brine (2×50 ml) and dry over MgSO$_4$. Filter off the drying agent and concentrate the filtrate to yield the title compound in crude form. Separate and purify by flash chromatography eluting with ethyl acetate-hexanes (1:3).

Preparative Example 32

1-HEXADECYLOXY-2-METHYL-2-METHOXY-3-CHLOROFORMYLOXYGLYCEROL

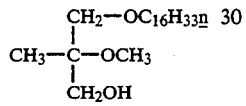

Mix the title compound of Preparative Example 31 (0.463 g) with THF (10 ml) at 0° C. Add trichloromethylchloroformate (0.193 ml) at once. Stir for 18 hours under an argon atmosphere, warming to room temperature.

Concentrate the reaction mixture in vacuo to give the title compound as a pale yellow oil.

Preparative Example 33

3-HEXADECYLOXY-2-METHOXY-2-METHYL-PROPYL-2-CHLOROETHYL CARBAMATE

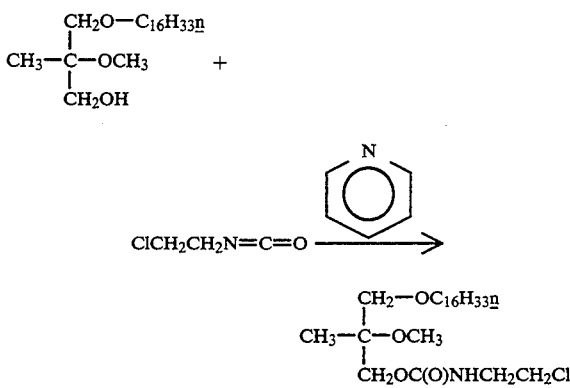

Add the title compound of Preparative Example 31 (0.8345 g) and β-chloroethylisocyanate (0.227 ml) to dry pyridine (25 ml) and stir at room temperature for 17 hours under an argon atmosphere. Concentrate in vacuo to yield the title compound.

Purify the title compound via column chromatography with Merck silica gel (20 g), eluting with ethylacetate-hexanes (1:4). Collect the appropriate fractions to obtain the title compound.

Preparative Example 34

3-[1,1-DIMETHYLETHYL)DIMETHYLSILYLOXY]-2-METHYLTHIO-2-METHYLPROPYL n-OCTADECYL CARBAMATE

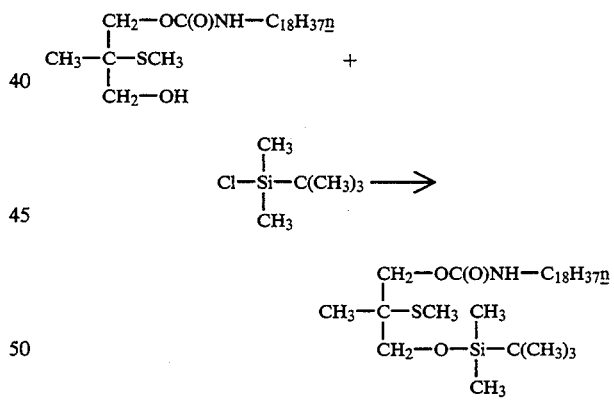

Add t-butyl dimethyl silylchloride (13.03 g, 0.0864 mol) in DMF (75 ml) dropwise over 8 minutes to a stirred solution of 3-octadecylcarbamoyloxy-2-methyl-2-methylthio-1-propanol, (37.28 g, 0.0864 mol) and diisopropylethylamine (15.87 ml, 0.0911 g)in DMF (200 ml) at 18° C. under a dry N$_2$ atmosphere. Stir the solution at room temperature for 3 hours 15 minutes at 32° C. Partition the residue between diethyl ether-H$_2$O, and monitor reaction progress by TLC, using ethyl acetate-hexanes (1:4).

Continue stirring as appropriate. Rotavap the reaction mixture to obtain a soft solid.

Flash chromatograph the soft solid loaded as its CH$_2$Cl$_2$ solution on a column of silica gel, eluting with ethyl acetate-hexanes (1:9).

Dry the eluent containing the title compound over Na$_2$SO$_4$ and rotavap to give the title compound as a viscous oil (41.82 g, 89% yield) which solidifies slowly to a white solid (mp 20°-22° C.).

Preparative Example 35

1-(N-METHYL-N-OCTADECYLCARBAMOYLOX-Y)-2-METHYL-2-METHYLTHIO-3-(t-BUTYL DIMETHYL SILYLOXY)PROPANE

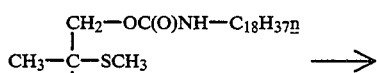

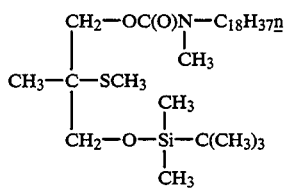

Treat the 2-methylthio compound from Preparative Example 34 with sodium hydride and CH$_3$I as described in Preparative Example 11 to make the title compound in the form of an oil.

Preparative Example 36

1-N-METHYL-N-OCTADECYLCARBAMOYLOX-Y)-2-METHYL SULFINYL-2-METHYL-3-METHYLSUL-FONYLOXYHEPTYLOXY PROPANE

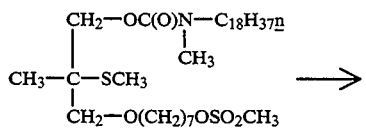

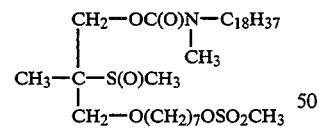

Stir a solution of the 2-methylthio compound from Preparative Example 18 (1.64 g, 2.57 mmol) and m-chloroperbenzoic acid (0.47 g, 2.70 mmol) in CH$_2$Cl$_2$ (40 ml) at room temperature. Wash with NaHCO$_3$ (1×1.1M) and H$_2$O (2×) and dry over MgSO$_4$. Rotavap to give a mixture of the sulfoxide, sulfide and sulfone.

The mixture may be rewashed with NaHCO$_3$ (2×1.1 m) and H$_2$O (1×), then dried over MgSO$_4$, rotavaped and high vac dried for 18 hours to yield an amber oil, (1.42 g) which contains the sulfoxide:sulfide (3:1).

Flash chromatograph on a column of silica gel and elute with ethyl acetate-hexanes (1:2), and collect the appropriate fractions to obtain the title compound as a mixture of 2 diastereoisomers in the form of an oil.

Preparative Example 37

1-(N-METHYL-N-OCTADECYLCARBAMOYLOX-Y)-2-METHYL-2-METHYLSULFONYL-3-METHYLSULFONYLOXYHEPTYLOXY PROPANE

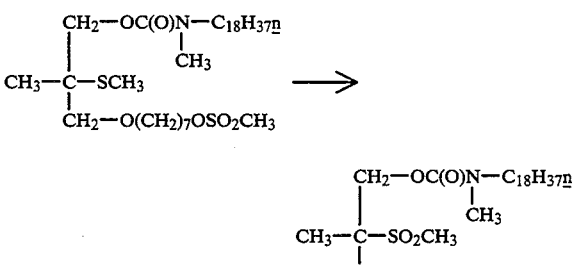

Stir a suspension of the 2-methylthio compound of Preparative Example 18 (2.75 g, 0.0043 mol) and m-chloroperbenzoic acid (2.50 g, 0.0145 mol) in CH$_2$Cl$_2$ (40 ml).

After stirring for 18 hours at room temperature, add a further quantity of m-chloroperbenzoic acid (0.82 g, 0.0040 mol) and continue stirring for 5.5 hours.

Wash the reaction mixture with NaHCO$_3$ (3×40 ml, 1.1M) and H$_2$O (1×50 ml) and dry over Na$_2$SO$_4$. Filter out the drying agent and rotavap the filtrate. Dry the residue in vacuo for 15 hours to obtain the title compound as a viscous oil.

Preparative Example 38

3-DIBENZYLAMINO-2-HYDROXY-2-METHYL-1(N-METHYL-N-OCTADECYLCARBAMOYLOX-Y)PROPANE

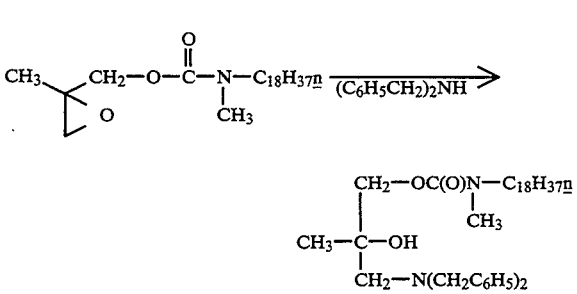

Heat a stirred mixture of the title compound of Preparative Example 30 (8.85 g, 22.3 mmoles) and dibenzylamine (27.9 g, 141 mmoles) to 130° C. under an inert atmosphere for 19 hours. Cool the resultant solution to room temperature, and dilute with CH$_2$Cl$_2$ (235 ml) and diethyl ether (35 ml). Stir the solution and add ethereal hydrochloric acid (50 ml, 170 mmoles, 3.4M). Stir the thick suspension, then filter. Remove solvent from the filtrate under reduced pressure. Redissolve the residual gum in a mixture of diethyl ether (210 ml) and CH$_2$Cl$_2$ (115 ml) and wash the resultant solution with saturated brine (150 ml). Filter through anhydrous MgSO$_4$, remove solvent from the filtrate under reduced pressure, and chromatograph the residual oil on silica gel, eluting with ethyl acetate-hexanes (1:4) to obtain the title compound as an analytically pure oil.

Preparative Example 39

3-DIBENZYLAMINO-2-METHYL-2-METHOXY-1-(N-METHYL-N-OCTADECYLCARBAMOYLOXY)PROPANE

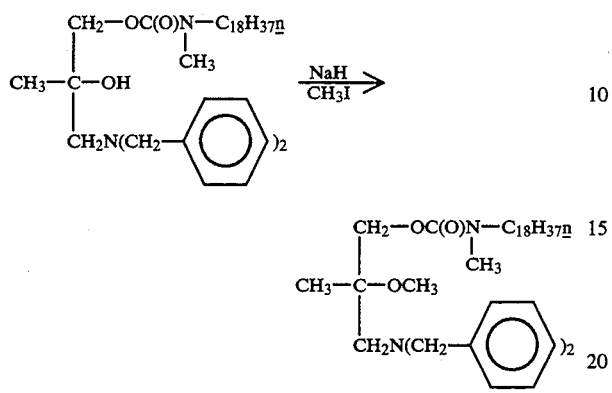

Treat the 2-hydroxy compound from the preceding Preparative Example with NaH and CH$_3$I as described in Preparative Example 11 to make the title compound in the form of an oil.

$^1$H NMR (CDCl$_3$): δ7.33, 7.29 (m, 10H), 4.08 (d, J=10 Hz, 1H), 3.96 (d, J=10 Hz, 1H), 3.71 (d, J=13.4 Hz, 1H),3.59 (d, J=13.4 Hz), 3.21 (s, 3H), approx. 3.2–3.0 (poorly defined multiplets, approx. 2H), 2.85/2.61 (sl broadened singlets, approx. 3H), 1.5–1.4 (br m, 2H), 1.25(m, 30H), 1.21 (s, 3H), 0.88 (t, 3H). MS (FAB): 609 [(M+1)+; 99%], 607 [(M−1)+; 100%], 531 (27%).

Preparative Example 40

3-AMINO-2-METHOXY-2-METHYL-3-(N-METHYL-N-OCTADECYLCARBAMOYLOXY)PROPANE

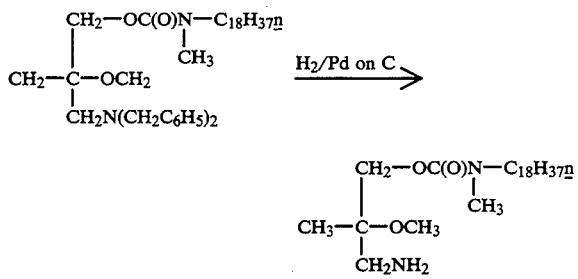

In a Parr shaker hydrogenation apparatus, combine 3-dibenzylamino-2-hydroxy-2-methyl-1-(N-methyl-N-octadecyl carbamoyloxy)propane from Preparative Example 39 (9.34 g, 15.3 mmoles), glacial acetic acid (0.981 g, 16.4 mmoles), 5% palladium-on-carbon catalyst (1.88 g) and anhydrous ethanol (130 ml). Allow the mixture to shake under 15 p.s.i. hydrogen pressure at room temperature for 110 min. Remove the catalyst by filtration through celite, remove the solvent from the filtrate at reduced pressure, and partition the residue between CH$_2$Cl$_2$ (150 ml) and a mixture of water (100 ml), brine (50 ml), and 1.1M aqueous sodium bicarbonate (50 ml, 1.1 M)). Separate the layers and extract the aqueous phase with CH$_2$Cl$_2$ (3×45 ml). Wash the combined extracts successively with water (100 ml) and brine (2×150 ml), filter through anhydrous MgSO$_4$, and strip off solvent under reduced pressure. Chromatograph the residual oil on silica gel, eluting with CH$_2$Cl$_2$—CH$_3$OH (stepped gradient, 95:5 to90:10 to 78:22), to obtain the title compound as an analytically pure gum (containing 0.2 mole of water).

$^1$H NMR (CDCl$_3$): δ4.18 (d; J=10 Hz, 1H), 3.98 (d, J=10 Hz, 1H), 3.3–3.2 (poorly resolved multiplet, 2H), 3.28(s, 3H), 2.90 (s, 3H), 2.72 (s, 2H), 1.70 (s, D$_2$O-exchangeable, >2H), 1.52 (br m, 2H), 1.27 (m, 30H), 1.17 (s, 3H), 0.89 (t, 3H). MS (FAB): 429 [(M+1)+; 100%].

Preparative Example 41

3-(ETHENYLSULFONYLAMINO)-2-METHOXY-2-METHYLPROPYL-N-METHYL-N-OCTADECYLCARBAMATE

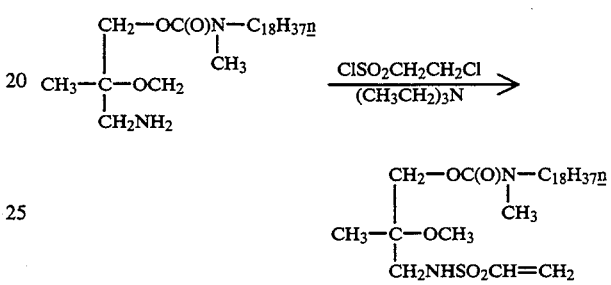

To a stirred mixture of the title compound of Preparative Example 40 (1.0 g, 2.33 mmoles) and (CH$_3$CH$_2$)$_3$N (283 mg, 2.80 mmoles) in dry THF (15 ml), add a solution of 2-chloroethanesulfonyl chloride (456 mg, 2.80 mmoles)in 1 ml of dry THF. Stir the resultant mixture under an inert atmosphere for 4 hours at room temperature. Filter the reaction mixture, concentrate the filtrate under reduced pressure, and partition the residue between ethyl acetate-brine (35 ml:35 ml). Separate the layers and extract the aqueous phase with ethyl acetate (2×15 ml). Wash the combined extracts with brine (35 ml), filter through anhydrous MgSO$_4$, and remove the solvent from the filtrate under reduced pressure. Chromatograph the residual oil on silica gel, eluting with ethyl acetate-hexanes (2:3), to obtain the title compound as an oil which displayed the following spectroscopic properties:

$^1$H NMR (CDCl$_3$): δ6.54 (dd, J=10, 17.5 Hz, 1H), 6.23 (d, J=17.5 Hz, 1H), 5.90 (d, J=10 Hz, 1H), 5.01 (br, m,1H), 4.12 (d, J=11 Hz, 1H), 4.04 (d, J=11 Hz, 1H), 3.27 (s, 3H), 3.20 (br t, 2H), 3.04 (d, J≦10 Hz, 2H), 2.90 (br s, 3H), 1.52 (br m, 2H), 1.28 (m, 30H), 1.23 (s,3H), 0.88 (t, 3H). MASS SPECTRUM (CHEMICAL IONIZATION): 519 [(M+1)+], 429(100%); 536 [(M+1+NH$_3$)+].

Preparative Example 42

2-METHYL-1-N,N-DIOCTYLCARBAMOYLOXY-2-PROPENE

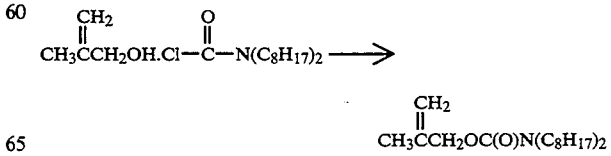

Heat a solution of 2-methyl-2-propen-1-ol (26.0 g; 0.36 mole) and N,N-dioctylchlorocarbonylamine (48.8 g; 0.12 mole; prepared from dioctylamine and trichloromethylchloroformate by standard methods) in dry tetrahydrofuran (126 mL) under nitrogen at 50° C. for 17 h. Add 2-methyl-2-propen-1-ol (34.6 g; 0.48 mole) and continue heating at 50° C. for another 31 hr before introducing a third quantity of the alcohol (8.65 g; 0.36 mole). Heat the reaction mixture under nitrogen at 80° C. for another 38 hr. Concentrate the mixture under reduced pressure, and flash chromatograph the residue on silica gel, eluting with ethyl acetate-hexane (5:95), to obtain the title compound as an oil.

EXAMPLE 1

3-[7-[3-(N-METHYL-N-OCTADECYLCARBAMOYLOXY)-2-METHOXY-2-METHYL-PROPOXY]HEPTYL]THIAZOLIUM METHANESULFONATE, HEMIHYDRATE

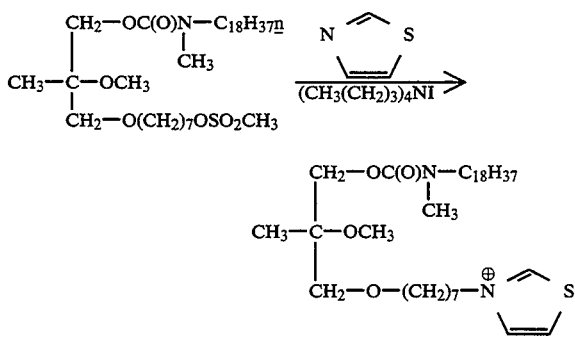

Heat a solution of the title compound of Preparative Example 17 (1.46 g, 2.35 mmol), thiazole (5 g, 587 mmol) and tetrabutylammonium iodide (43.4 mg, 0.18 mmol) under a $N_2$ atmosphere at 80° C. for 5 hours. Monitor the reaction progress by TLC.

Distill off excess thiazole and dry the residue on a rotavap to yield the title compound as an amber gum. High vac dry the sample to yield the title compound as a brown glass. (1.50 g yield). Purify via flash chromatography on silica gel eluting the sample with $CH_2Cl_2$—$CH_3OH$—$H_2O$ (81:18:1). Dry over $Na_2SO_4$, rotavap and high vac dry to obtain a white gum.

Further purify the title compound by dissolving in diethyl ether and dry over $MgSO_4$. Rotavap and high vac dry to obtain a white amorphous solid.

The sample may be dissolved in hexane (7 ml) at −11° C. Filter off a soft, white solid, which melts on warming to room temperature to give a viscous oil. Redissolve the sample in hexane and stir with Darco 660 (0.3 g), filter, rotavap and high vac dry to yield an off-white sticky glass. High vac dry over $P_2O_5$ to obtain the title compound as a waxy gum which darkens slightly over time.

EXAMPLE 2

Substitute the appropriate starting material selected from column 1 of Table 2 below into the procedure described in Example 1 to make the end product shown in column 2.

TABLE 2

$$A + CH_3-\underset{\underset{CH_2-O(CH_2)_7OSO_2CH_3}{|}}{\overset{\overset{CH_2-OC(O)N-C_{18}H_{27}\underline{n}}{|}}{C}}-OCH_3 \quad CH_3 \longrightarrow B$$

| Starting Material A = | End Product B = |
|---|---|
| thiazole ring (N, S) | $CH_3-C(OCH_3)(CH_3)$ with $CH_2-OC(O)N-C_{18}H_{37}\underline{n}$ and $CH_2-O(CH_2)_7-N$(thiazolium) |
| imidazole ring (N, NH) | $CH_3-C(OCH_3)(CH_3)$ with $CH_2-OC(O)N-C_{81}H_{37}\underline{n}$ and $CH_2-O(CH_2)_7-N$(imidazolium-N) |
| imidazole with $CH_2CO_2CH_2$-phenyl | $CH_3-C(OCH_3)(CH_3)$ with $CH_2-OC(O)N-C_{18}H_{37}\underline{n}$ and $CH_2-O(CH_2)_7-N$(imidazolium-N), $CH_2CO_2CH_2$-phenyl |

TABLE 2-continued
$$A + CH_3-\underset{\underset{CH_2-O(CH_2)_7OSO_2CH_3}{|}}{\overset{\overset{CH_2-OC(O)N-C_{18}H_{27}n}{|}}{C}}-OCH_3 \quad \underset{CH_3}{} \longrightarrow B$$
| Starting Material A = | End Product B = |
|---|---|
| 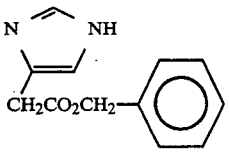 | 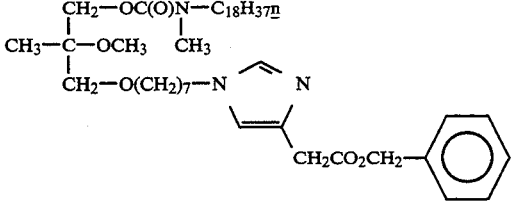 |
| 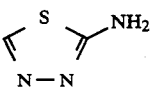 | 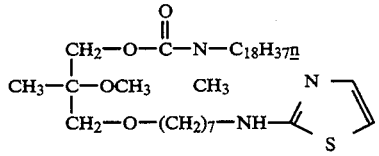 |
| 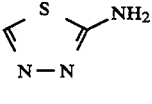 | 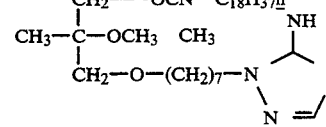 |
| 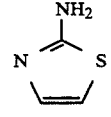 | 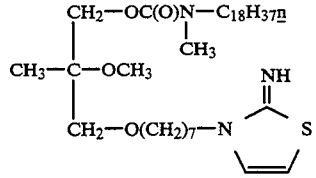 |
|  | 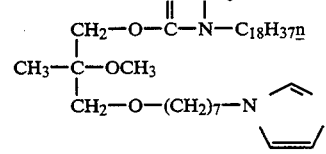 |
| 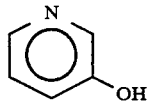 | 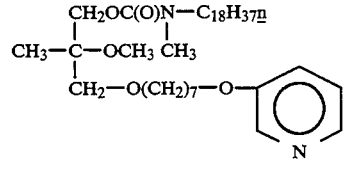 |
| 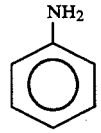 | 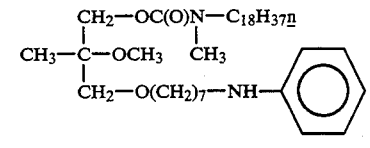 |
| 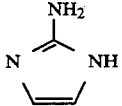 | 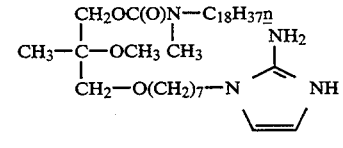 |

TABLE 2-continued $$A + CH_3-\underset{\underset{CH_2-O(CH_2)_7OSO_2CH_3}{|}}{\overset{\overset{CH_2-OC(O)N-C_{18}H_{27}n}{|}}{C}}-OCH_3 \longrightarrow B$$

| Starting Material<br>A = | End Product<br>B = |
|---|---|

TABLE 2-continued

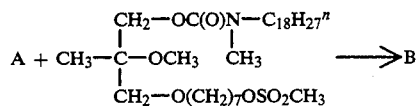

| Starting Material A = | End Product B = |
|---|---|
| 2-aminobenzothiazole | benzothiazole-C18H37n carbamate product |
| guanidine (NH2-C(=NH)-NH2) | guanidine-C18H37n carbamate product |
| 2-aminopyridine | pyridine-C18H37n carbamate product |
| 2-amino-4-methylthiazole | 4-methylthiazole-C18H37n carbamate product |

EXAMPLE 3

3-{4-[3-(N-METHYL-N-OCTADECYLCARBAMOYLOXY)-2-METHOXY-2-METHYL-PROPOXY]BUTYL}THIAZOLIUM, METHANESULFONATE

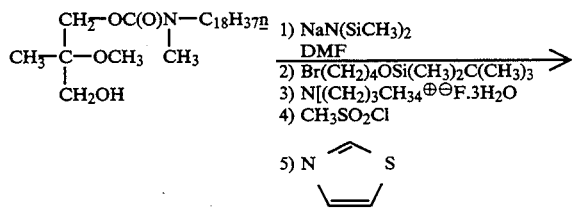

1) NaN(SiCH3)2 DMF
2) Br(CH2)4OSi(CH3)2C(CH3)3
3) N[(CH2)3CH34]⊕⊖F.3H2O
4) CH3SO2Cl
5) thiazole -continued

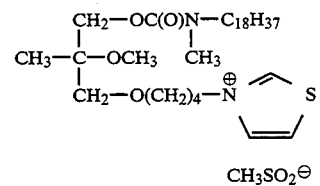

CH3SO2⊖

Substitute silylated bromobutanol for the analogously protected bromoheptanol in the procedure described in Preparative Example 13. Deprotect with N(CH2CH2CH2CH3)4F.3H2O, as described in Preparative Example 15 and mesylate as described in Preparative Example 17. Introduce thiazole as in Example 1 to obtain the title compound.

EXAMPLE 4

The compounds shown in column 1 of Table 4 below may be debenzylated under a H2 atmosphere by treating with Pd on carbon (10%) under standard reaction conditions to synthesize the compounds shown in column two.

TABLE 4

| Reactant | End Product | Notes |
|---|---|---|
| 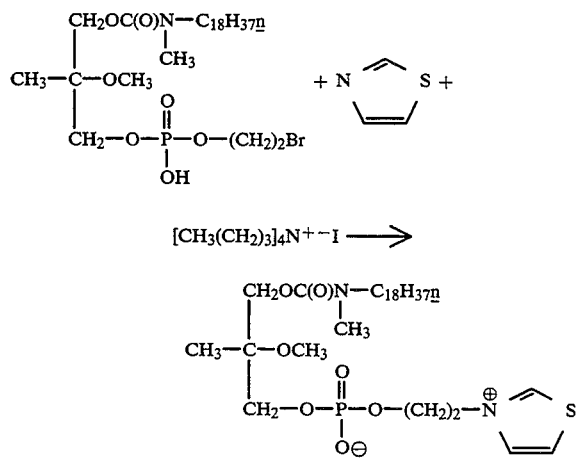 | | |

EXAMPLE 5

3-(N-METHYL)OCTADECYLCARBAMOYLOXY-2-METHOXY-2-METHYLPROPYL-2-THIAZOLIO ETHYLPHOSPHATE

Combine the title compound of Preparative Example 19 (2.96 g), thiazole (8.4 g) and tetrabutylammonium iodide (1.36 g) at room temperature and heat in a preheated oil bath to 120° C. for 2 hours 15 min. Add ether, stir and filter to remove insolubles. Concentrate the filtrate and purify via flash chromatography on silica gel, eluting with $CHCl_3$—$CH_3OH$—$H_2O$ (65:25:3). Combine the appropriate fractions, rotavap in high vacuo at 30° C. to obtain a sticky brown solid.

Dissolve the sticky brown solid in methanol, and precipitate with ethyl acetate. Filter to give an off-white hygroscopic solid. Dry in high vacuo at room temperature over $P_2O_5$ for 2 days to give the title compound as a bromide salt.

Isolation of Zwitterions

Purify the crude product (0.6 g) by flash chromatography with $CHCl_3:CH_3OH:H_2O$ (75:24:1) (2×). Combine the appropriate fractions after the second chromatography, rotavap in high vacuo at 30° to 35° C., then dry in high vacuo over $P_2O_5$ for two days to obtain the zwitterionic form of the title compound as the monohydrate. The zwitterionic form of the product may also be prepared by treatment of the bromide salt with methanolic silver carbonate.

EXAMPLE 6

Following the procedure described above in Example 5, substitute the reactants from column 1 and 2 from Table 6 below to make the products shown in column 3.

TABLE 6

TABLE 6-continued

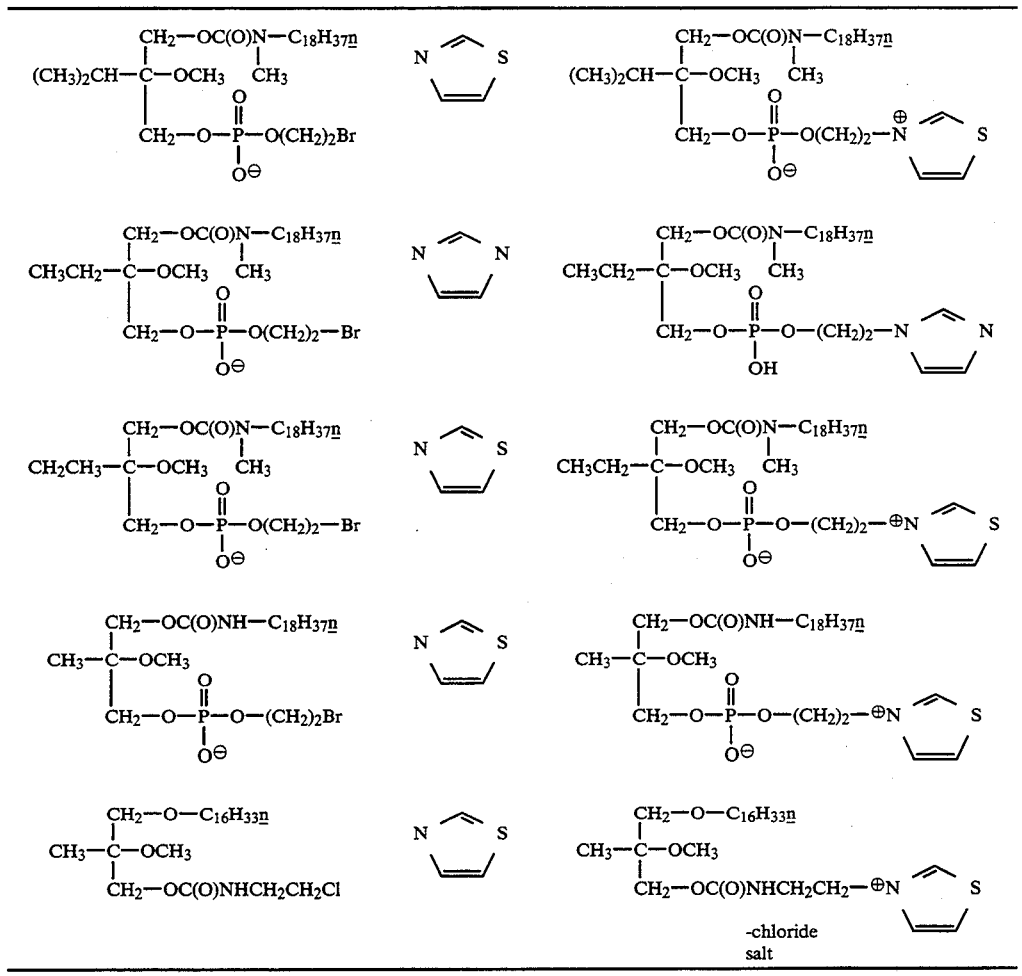

EXAMPLE 7

3-[4-[3-(N-METHYL-N-OCTADECYLCAR-
BAMOYLOXY)-2-METHOXY-2-METHYL-
PROPOXYMETHYL]BENZYL]THIAZOLIUM,
METHANESULFONATE

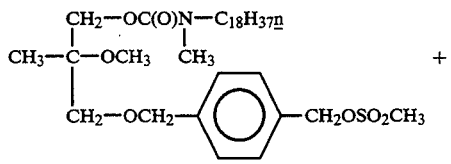

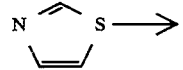

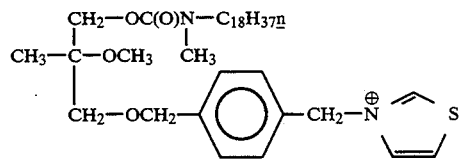

Heat the title compound of Preparative Example 23 (2.24 g) with thiazole (2 ml) at 80° C. under a N₂ atmosphere until reaction is complete as monitored by TLC.

Distill off excess thiazole in a water bath (35° to 40° C.), trapping the thiazole with a dry ice trap to yield the title compound in crude form as a tan glass.

To purify, flash chromatograph the title compound with CH₂Cl₂—CH₃OH—H₂O (80:18:0.25) on a column of silica gel to obtain the title compound as a white waxy solid.

Further purify the white waxy solid by stirring in hexanes (5 ml) and filtering the resulting cloudy solution through medium sintered glass, then washing with additional hexanes (2×3 ml) to obtain a white solid filter cake.

Rotavap the filtrate to obtain the title compound as a viscous oil, which solidifies after high vac drying over P₂O₅ (m.p. 33° to 42° C.).

EXAMPLE 8

3-(7-METHOXY-7,11-DIMETHYL-4,10-DIOXO-5,9-
DIOXA-3,11-DIAZANONACOSYL)-
THIAZOLIUM IODIDE, 1½ HYDRATE

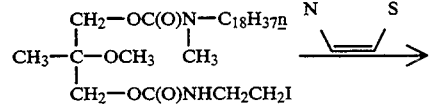

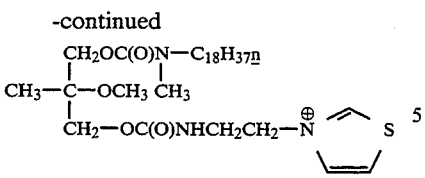

Combine the title compound of Preparative Example 25 (0.4 g) and thiazole (2.0 g) and stir at room temperature for 17 hours, and monitor reaction progress by TLC (CH$_3$OH—CH$_2$Cl$_2$; 1:9).

To further purify the compound, stir at 95° to 100° C. and monitor by TLC, then chromatograph on silica gel (100 g), eluting with CH$_2$Cl$_2$ (300 ml), 10% CH$_3$OH in CH$_2$Cl$_2$ (200 ml) and H$_2$O—CH$_3$OH—CH$_2$Cl$_2$ (5:30:100). Dry the appropriate fractions to obtain the title compound as a hygroscopic yellow solid, which may be suspended in diethyl ether and filtered.

EXAMPLE 9

(3-ACETYL-7,11-DIMETHYL-3,11-DIAZA-5,9-DIOXA-4,10-DIOXO-7-METHOXYNONACOSYL) PYRIDINIUM CHLORIDE, 1½ HYDRATE

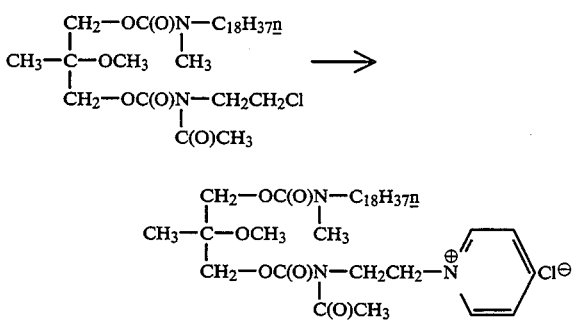

Reflux a mixture of the title compound of Preparative Example 26 (1.0 g) in pyridine (12 ml) for 18 hours under a N$_2$ atmosphere. Monitor reaction progress by TLC in ethyl acetate-CH$_2$Cl$_2$ (1:4).

Remove pyridine in vacuo and chromatograph the crude product on silica gel, eluting with 5-20% CH$_3$OH—CH$_2$Cl$_2$ to obtain the title compound in crude form. Dissolve the crude product in CH$_2$Cl$_2$, filter to obtain a clear yellow solution, and concentrate the filtrate to dryness. Add diethyl ether and concentrate to dryness a second time, to obtain a yellow gummy solid. Dry in a vacuum oven overnight to yield the title compound as the chloride salt.

EXAMPLE 10

1-[2-[[[[2-METHOXY-2-METHYL-3-[[(N-METHYL-N-OCTADECYLAMINO)CARBONYL]OXY]-PROPYL]OXY]CARBONYL]AMINO]ETHYL]-PYRIDINIUM CHLORIDE, 1½ HYDRATE

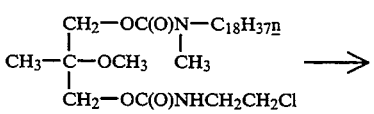

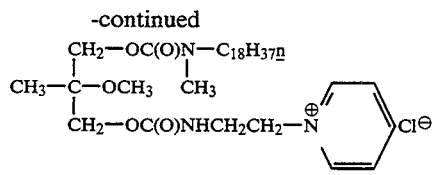

Dissolve the title compound of Preparative Example 24 (800 mg) in pyridine (10 ml) and reflux under a N$_2$ atmosphere for 18 hours. Monitor reaction progress with TLC using CHCl$_3$—CH$_3$OH—H$_2$O (65:25:4). When reaction is complete, remove the solvent under high vacuum. Chromatograph the residue using TLC grade silica gel (25 g) and elute with CH$_3$OH—CHCl$_3$ (15:85). Remove solvents using a rotavap and add CHCl$_3$ dried over MgSO$_4$. Filter and remove the solvent under high vacuum. Chromatograph the residue. Filter and remove solvent to yield an oil. Dry in vacuo until the oil solidifies to a waxy solid.

Redissolve the resultant waxy solid in CH$_2$Cl$_2$ and dry over MgSO$_4$. Filter and remove the solvent under high vacuum to obtain the title compound as a yellow-green gummy solid.

EXAMPLE 11

(7-METHOXY-7,11-DIMETHYL-4,10-DIOXO-5,9-DIOXA-3,11-DIAZANONACOSYL)TRIMETHYL AMMONIUM CHLORIDE

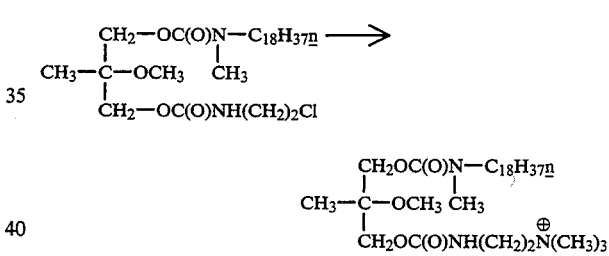

Substitute (CH$_3$)$_3$N (3 ml) into the procedure described in Example 10 for pyridine to make the title compound as the chloride salt in the form of a white solid (m.p. partial 110°-130° C.).

By substituting thiazole for pyridine in the procedure described in Example 10, and substituting an alternative starting material in Preparative Example 24 for β-chloroethylisocyanate, such as Cl(CH$_2$)$_5$NC(O), 6,14-diaza-10,14-dimethyl-8,2-dioxa-7,13-dioxo-10-methoxydotriacontanylthiazolium is obtained as the chloride salt in the form of a gummy yellow solid.

EXAMPLE 12

3-{7-[3-(N-METHYL-N-(OCTADECYLCAR-BAMOYLOXY)-2-ETHYL-2-METHYLPROPOXY]-HEPTYL}THIAZOLIUM, METHANESULFONATE, HEMIHYDRATE

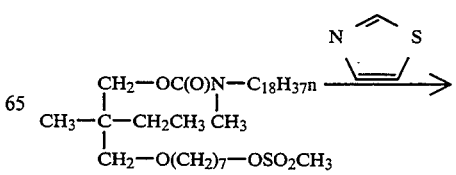

-continued

CH₂—OC(O)N—C₁₈H₃₇ₙ
|       |
CH₃—C—CH₂CH₃  CH₃
|            ⊕  ⌒
CH₂—O(CH₂)₇—N   S
              ⌣
    OSO₂CH₃⊖

Heat the appropriate compound of Preparative Example 18 (694.1 mg, 1.12 mmol) and thiazole (2.4 g, 28.2 mmol) in solution at 80° C. for 22 hours under a N₂ atmosphere. TLC the reaction mixture to monitor reaction progress.

Distill off excess thiazole at reduced pressure in a water bath, maintaining the temperature at 35° C. Flash chromatograph the residue (602.4 mg) using a column of silica gel, eluting with CH₂Cl₂—CH₃OH—H₂O(80:18:0.25).

Dissolve the eluted compound (514.4 mg) in CH₂Cl₂, dry over MgSO₄, rotavap and high vac dry with a rotavap to give the title compound as a mixture of oil and wax.

EXAMPLE 13

3-{7-[3-(N-METHYL-N-OCTADECYLCAR-BAMOYLOXY)-2-METHYLTHIO-2-METHYL-PROPOXY]HEPTYL}THIAZOLIUM, METHANESULFONATE

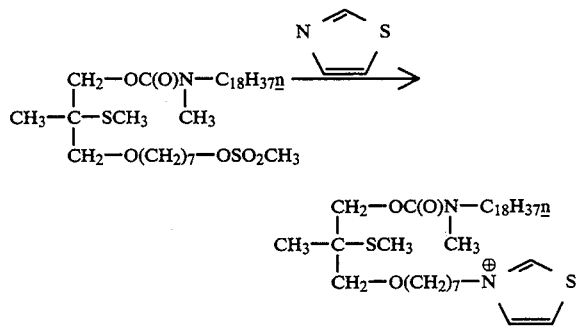

Dissolve the appropriate compound of Preparative Example 18 (1.53 g, 2.40 mmol) in thiazole (5.0 g, 58.7 mmol) and heat to 80° C. for 18 hours under a N₂ atmosphere.

Distill off the thiazole at 25°–30° C. under reduced pressure, and dissolve the resulting residue in CH₂Cl₂. Filter the solution and load the filtrate on a column of silica gel. Flash chromatograph, eluting with CH₂Cl₂—CH₃OH—H₂O (81:18:1). Collect the appropriate fractions and evaporate to yield a soft glassy gum.

Dissolve the gum in diethyl ether, filter and rotavap at 28° C. High vac dry the residue. Dissolve the residue in hexanes and high vac dry over P₂O₅ to form a soft brown wax. Dissolve the sample in CH₂Cl₂, wash with NaHCO₃ solution (2×1.1M) and dry to yield the title compound as the 1.25 hydrate.

EXAMPLE 14

Treat the compound shown in column 1 below with thiazole (2 ml, 28.2 mmol) as described in Example 13 to make a compound shown in column two.

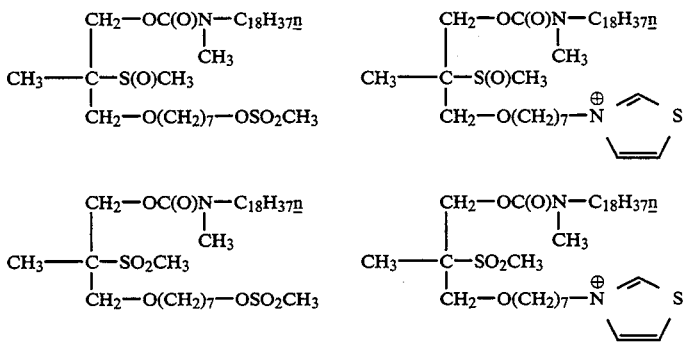

EXAMPLE 15

3-{[{2-(1H-IMIDAZOL-1-YL)ETHYL}SUL-FONYL]AMINO}-2-METHOXY-2-METHYLPRO-PYL METHYL OCTADECYLCARBAMATE

CH₂—OC(O)N—C₁₈H₃₇ₙ       N⌒NH
|          |                ⌣
           CH₃
CH₃—C—OCH₃                       NaH, DMF
|                              ─────────→
CH₂NHSO₂CH=CH₂

CH₂—OC(O)N—C₁₈H₃₇ₙ
|          |
           CH₃
CH₃—C—OCH₃
|                          ⌒
CH₂—NHSO₂CH₂CH₂—N   N
                  ⌣

Add imidazole (526 mg, 7.72 mmoles), followed by NaH (61.6 mg, 1.54 mmoles 60%), to a solution of the title compound of Preparative Example 41 (400 mg, 0.772 mmoles) in DMF (12 ml). Stir the resultant mixture for 24 h at room temperature under an inert atmosphere. Filter the reaction mixture, and remove the solvent from the filtrate under reduced pressure. Dissolve the residue in a mixture of CH₂Cl₂ (10 ml) and diethyl ether(15 ml), and wash the solution with a brine (20 ml)-water (5 ml) mixture. Back-extract the aqueous layer with two 10-ml volumes of CH₂Cl₂. Filter the combined extracts through anhydrous MgSO₄, and remove solvent from the filtrate under reduced pressure. Chromatograph the residual oil on silica gel, eluting with CH₂Cl₂—CH₃OH (90:10), to obtain the title compound as an analytically pure, slightly sticky solid.

¹H NMR (CDCl₃): δ7.63 (s, 1H), 7.10 (apparent singlet, 1H), 7.00 (apparent singlet, 1H), 5.41 (br s, D₂O-exchangeable, 1H), 4.47 (t, J=7.5 Hz, 2H), 4.20 (d, J=12.5 Hz, 1H), 3.95 (d, J=12.5 Hz, 1H), 3.48 (t, J=7.5

Hz, 2H), 3.3–3.0 (complex m, 4H), 3.26 (s, 3H), 2.90 (two closely spaced peaks, 3H), 1.51 (distorted triplet, 2H), 1.28 (m, 30H), 1.20 (s 3H), 0.90 (t, 3H). MS (FAB): 587 [(M+1)+; 100%].

EXAMPLE 16

(4,10-DIAZA-6,10-DIMETHYL-6-METHOXY-8-OXA-9-OXO-3-SULFONYLOCTACOSYL)-3-METHYL IMIDAZOLIUM METHYLSULFATE

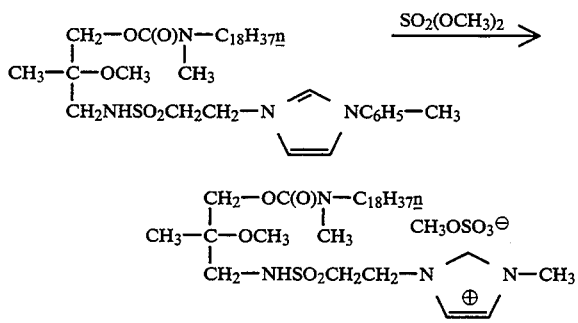

Add dimethyl sulfate (49.4 mg, 0.393 mmoles) to a solution of the title compound of Example 15 (115 mg, 0.196 mmole) in toluene (2 ml). Heat the resultant solution at 50° C. under an inert atmosphere for two hours. Remove solvent at reduced pressure, and chromatograph the residual oil on silica gel, eluting with $CH_2Cl_2:CH_3OH:H_2O$ (65:25:4), to obtain the title compound as an analytically pure gum.

$^1$H NMR (CDCl$_3$): δ9.49 (s, 1H), 7.60 (br s, 1H), 7.26 (br s, 1H), 6.46 (br m, 1H), 4.76 (m, 2H),4.2–3.9 (m, 2H), 3.96 (s, 3H), 3.74 (s, 3H),3.69 (t, J=6 Hz, 2H), 3.3–3.1 (overlapping multiplets, 4H), 3.27 (s, 3H), 2.89 (s, 3H), 1.51 (m, 2H), 1.27 (m, 30H), 1.23 (s, 3H), 0.88 (t, 3H). MS (FAB): 601 (M+ of quaternary cation).

EXAMPLE 17

1-HEXADECYLOXY-2-METHOXY-2-METHYL-3-[[[2-(N,N-DIMETHYL AMINO)ETHOXY]CARBONYL]OXY]PROPANE

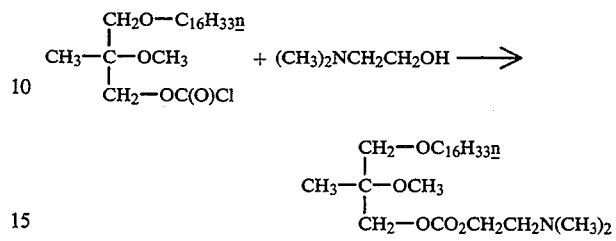

Stir the title compound of Preparative Example 32 (0.3242 g) and benzene (5 ml) at 0° C., and add dimethyl aminoethanol (0.088 ml) and (CH$_3$CH$_2$)$_3$N (20 ml). Stir the solution for 0.5 hours and concentrate in vacuo. Dilute the solution with pet ether (5 ml) and filter. Wash the filtrate with pet ether (2×5 ml) and concentrate to form the title compound as an orange oil.

Separate chromatographically using TLC grade silica (40 g) eluting with ethyl acetate-hexanes-(CH$_3$CH$_2$)$_3$N (25:2:73).

Collect the appropriate fractions and concentrate to obtain the title compound.

By treating the title compound of Example 17 with CH$_3$I under standard reaction conditions, the trimethyl ammonium compound is obtained.

EXAMPLE 18

By substituting the compound shown in column 1 of Table 18 below for dimethylamino ethanol in Example 17 above, the products shown in column 2 are prepared.

TABLE

| Reactant | Product | Notes |
|---|---|---|
| CH$_2$CH$_2$OH—[pyrrolidine N] | CH$_2$—OC$_{16}$H$_{33}$n / CH$_3$—C—OCH$_3$ / CH$_2$—OC(O)$_2$CH$_2$CH$_2$—N[pyrrolidine] | The product may be treated with CH$_3$I under standard reaction conditions to obtain the N-methyl ammonium compound. |
| HCH$_2$CCH$_2$—N[imidazole]N | CH$_2$—OC$_{16}$H$_{33}$n / CH$_3$—C—OCH$_3$ / CH$_2$—OC(O)$_2$CH$_2$CH$_2$—N[pyrrolidine] | |
| HOCH$_2$CH$_2$—N[morpholine]O | CH$_2$—O—C$_{16}$H$_{33}$n / CH$_3$—C—OCH$_3$ / CH$_2$—OCO$_2$—CH$_2$CH$_2$—N[morpholine]O | |
| BrCH$_2$CH$_2$OH | CH$_2$—O—C$_{16}$H$_{33}$n / CH$_3$—C—OCH$_3$ / CH$_2$OCO$_2$CH$_2$CH$_2$Br | |

EXAMPLE 19

1-HEXADECYLOXY-2-METHOXY-2-METHYL-3-[[[2-(2-METHYLIMIDAZOL-1-YL)ETHOXY]CARBONYL]OXY]PROPANE

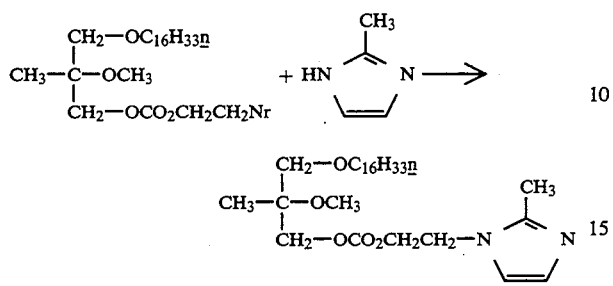

Mix the bromocarbonate compound from Example 18 with 2-methylimidazole (1.25 eq.) in 2-butanone (15 ml) and heat to reflux under an argon atmosphere for 18 hours.

Concentrate the reaction in vacuo and purify chromatographically with silica gel (20 g TLC grade), eluting with $CHCl_3:CH_3OH$ (7:3) then $CHCl_3:CH_3OH:7+20$ (7.0:3.5:0.5) to obtain the title compound as a clear oil.

EXAMPLE 20

1-HEXADECYLOXY-2-METHOXY-2-METHYL-3-[[[2-(2-METHYL-3-N-METHYL-IMIDAZOL-1-YL)ETHOXY]CARBONYL]OXY]PROPANE, IODIDE

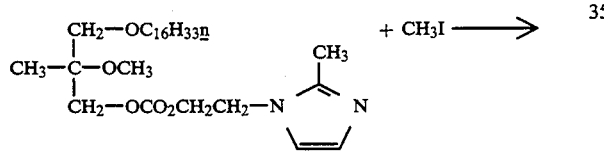

-continued

Stir the title compound from Example 19 (0.2453 g, 0.493 mmol) and $CH_3I$(0,046 ml, 0,741 mmol, 1.5 meq) in dry benzene (15 ml) and heat to reflux for 3 hours. Collect the resultant precipitate in vacuo to obtain the title compound. MS: FAB (M-Iodine) 511.

EXAMPLE 21

1-HEXADECYLOXY-2-METHOXY-2-METHYL-3-[[[2(N,N-DIMETHYLAMINO)ETHOXY]CARBONYL]OXY]-PROPANE

Substitute pyridine for 2-methylimidazole in the procedure described in Example 19 above to make the title compound as the bromide salt.

EXAMPLE 22

Treat the reactant in column 1 of the table below with $CH_3I$ as described in Example 20 to make the product shown in column 2 below.

| Reactant | Product |
|---|---|
| $CH_3-\underset{\underset{CH_2OCO_2CH_2CH_2N(CH_3)_2}{|}}{\overset{\overset{CH_2-OC_{16}H_{33}n}{|}}{C}}-OCH_3$ | $CH_3-\underset{\underset{CH_2-OCO_2CH_2CH_2\overset{\oplus}{N}(CH_3)_3}{|}}{\overset{\overset{CH_2-OC_{16}H_{33}n}{|}}{C}}-OCH_3 \quad I^{\ominus}$ |
| $CH_3-\underset{\underset{CH_2-OCO_2CH_2CH_2-N}{|}}{\overset{\overset{CH_2OC_{16}H_{33}n}{|}}{C}}OCH_3$ pyrrolidine | $CH_3-\underset{\underset{CH_2OCO_2CH_2CH_2-N(+)}{|}}{\overset{\overset{CH_2-OC_{16}H_{33}n}{|}}{C}}-OCH_3$ $I^{\ominus}$ $CH_3$ |

EXAMPLE 23

Substitute the reactant shown in column 1 below into the procedure described in Example 10 to make the product shown in column 2 below.

| Reactant | Product | Notes |
|---|---|---|
| CH₃—C(CH₂OC(O)N(CH₃)—C₁₈H₃₇n)(OCH₃)—CH₂—NHCO₂CH₂CH₂Cl | CH₃—C(CH₂OC(O)N(CH₃)—C₁₈H₃₇n)(OCH₃)—CH₂—NHCO₂CH₂CH₂—N⁺(pyridinium) Cl⁻ | Compound in the form of a waxy solid. |

EXAMPLE 24

Substitute the appropriate starting material shown below for pyridine in Example 23 above to obtain the product shown below.

EXAMPLE 25

7-[2-METHOXY-2-METHYL-3-[(METHYLOCTADECYLCARBAMOYL-OXY)PROPOXY]HEPTYL]-4-THIAZOLIDINECARBOXYLATE

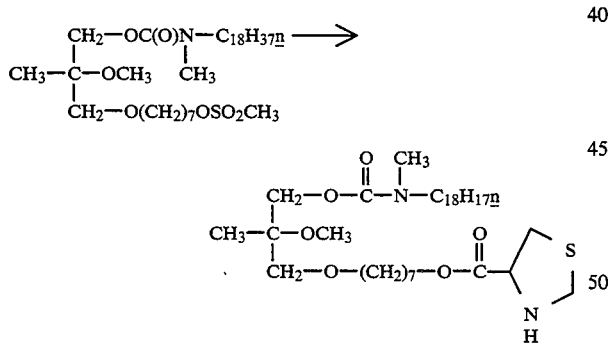

Heat a solution of the title compound of Preparative Example 17 (1.87 g; 3.01 mmole) and R-(—)-thiazolidine-4-carboxylic acid, sodium salt (0.47 g; 3.01 mmole), in 30 mL of dry dimethylsulfoxide under nitrogen at 50° C. for 9 h. Pour the reaction mixture into 95 mL of saturated aqueous NaCl and extract with diethyl ether (4×50 mL). Wash the combined extracts with water and dry over anhydrous Na₂SO₄. Filter out the drying agent, and remove the solvent from the filtrate under vacuum. Chromatograph the residue on silica gee, eluting with acetone-methylene chloride (1:9), to obtain the title compound. If necessary, the product thus isolated may be rechromatographed using the same solvent system to obtain the title compound as an analytically pure oil.

EXAMPLE 26

7-[2-METHOXY-2-METHYL-3-[(METHYLOCTADECYLCARBAMOYLOXY)-PROPOXY]HEPTYL]-2-AMINO-3-METHYLTHIO)PROPIONATE

[Structure showing CH₂—OC(O)N—C₁₈H₃₇n with CH₃, CH₃—C—OCH₃, CH₂—O(CH₂)₇OSO₂CH₃ → product with NH₂, CH₂SCH₃ group]

Substitute the sodium salt of S-methyl-L-cysteine for R-(—)-thiazolidine-4-carboxylic acid, sodium salt, in the procedure described in Example 25 to obtain the title compound.

EXAMPLE 27

3-[7-[(3-(PYRIDINYL)OXY]HEPTYLOXY]-2-METHOXY-2-METHYLPROPYL METHYLOCTADECYLCARBAMATE

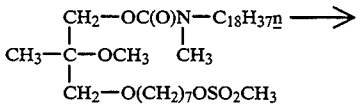

-continued

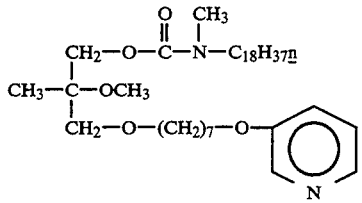

Heat a mixture of the title compound of Preparative Example 17 (500 mg; 0.804 mmole), 3-hydroxypyridine (380 mg; 3.90 mmoles), and tetrabutylammonium iodide (0.060 mmoles) for 1 hour at 130° C. Filter the reaction mixture through a pad of silica gel, eluting with acetone-methylene chloride-water (100:10:1) to obtain the mesylate salt form of the title compound as a yellow semisolid.

Dissolve the mesylate salt in methylene chloride and wash the solution successively with aqueous sodium bicarbonate, water, and brine. Dry the organic layer over anhydrous sodium sulfate, filter, and concentrate the filtrate under vacuum. Dry the resultant residue in vacuo over phosphorus pentoxide to obtain the free base form of the title compound as a dark green oil.

Dissolve the free base (75 mg; 0.112 mmoles) in 0.5 ml of methylene chloride and add 0.04 mL of 3.4M etheral hydrochloric acid. Stir at room temperature for 5 minutes, remove volatiles and dry over phosphorus pentoxide under vacuum to obtain the monohydrated hydrochloride acid salt form of the title compound as an analytically pure brown semisolid.

EXAMPLE 28

CARBAMIC ACID, PHENYL[2-METHOXY-2-METHYL-3-(7-THIAZOLIUMHEPTYLOXY)PROPYL]ESTER, METHANESULFONATE

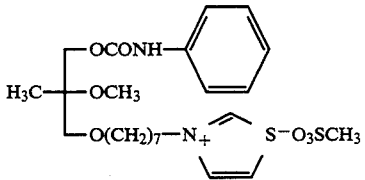

STEP A. 1-BROMO-7-(t-BUTYLDIMETHYL-SILYL)-OXYHEPTANE. To a stirred solution of 7-bromo-heptan-1-ol (15.7 g, 80.6 mmol) and diisopropylethylamine (15.6 g, 121 mmol) in 30 mL of dry methylene chloride, blanketed with nitrogen and maintained at 0°-5° C. by means of an ice-water bath, add rapidly a solution of tert-butyldimethylsilyl chloride (14.6 g, 96.7 mmol) in 20 mL of dry methylene chloride. Stir the resultant reaction mixture for 30 rain at 0°-5° C., then remove the ice-water bath and allow the mixture to stir at room temperature for 2.25 h. Concentrate the mixture under vacuum, and stir the residue with 300 mL of dry hexane. Filter out the precipitate of triethylamine hydrochloride, and wash the filter cake with additional hexane. Remove hexane under vacuum from the combined filtrate and washes, redissolve the residue in petroleum ether, and filter the solution through a pad of silica gel. Remove solvent from the filtrate under vacuum to obtain the title compound as a pale yellow oil, which may be used directly in Step B without further purification.

STEP B. 1-{7-[(t-BUTYLDIMETHYLSILYL)OX-Y]HEPTYLOXY}-2-METHYL-2-PROPENE. To a stirred suspension of sodium hydride (1.57 g of a 60% dispersion in mineral oil, 39.2 mmol; used without washing) in 10 mL of N,N-dimethylformamide (DMF), maintained at <10° C. (ice-water bath) under a nitrogen atmosphere, add a solution of 2-methyl-2-propen-1-ol (2.57 g, 35.6 mmol). Remove the cooling bath, and stir the mixture at room temperature for 1.5 h. Cool the resultant gray suspension to approximately 15° C., and add a solution of 1-bromo-7-(t-butyldimethylsilyl)oxyheptane (12.1 g, 39.2 mmol; from Step A above) in 5 mL of DMF. Dilute with another 5 mL portion of DMF, heat the stirred suspension at 50° C. for 4 h, then stir at room temperature for an additional 17.5 h. Pour the reaction mixture into water (150 mL), and extract with ether (3×25 mL). Wash the combined extracts successively with water (3×) and brine (1×). Dry over anhydrous magnesium sulfate, filter out the drying agent, and remove solvent under reduced pressure. Chromatograph the residual oil on silica gel, eluting with acetone-hexane (2:98), to obtain the title compound as a nearly colorless oil that can be used directly in Step C below.

STEP C. 1-[7-(HYDROXY)HEPTYLOXY-2-METHYL-2-PROPENE. To a stirred solution of the silyl ether product of Step B above (50.9 g, 0.169 mol) in dry tetrahydrofuran (800 mL) add tetrabutylammonium fluoride trihydrate (63.9 g, 0.203 mol), and stir the reaction mixture at room temperature for 2 h. Concentrate the mixture by evaporation under reduced pressure. Dissolve the residual oil in ether (180 mL) and wash successively with water (4×) and brine (1×). Dry the ether solution over anhydrous magnesium sulfate, filter, and remove the ether under reduced pressure. Dissolve the residue in hexane (150 mL) and filter through a bed (50 mm high × 100 mm diameter) of TLC grade silica gel (e.g., Baker 7024). Wash the silica bed with ethyl acetate-hexane (1:4). Combine the original filtrate and the washings, and remove solvent under reduced pressure. Dissolve the residual oil in hexane (100 mL), and repeat the filtration through silica, eluting with ethyl acetate-hexane (3:97). Remove solvent under reduced pressure from the collected eluent to obtain the title compound as an oil that may be used directly in Step D below without further purification.

STEP D. 1-[7-(BENZYLOXY)HEPTYLOXY[-2-METHYL-2-PROPENE. To a stirred suspension of sodium hydride (6.20 g of a 60% dispersion in mineral oil, 155 mmol; washed 3× with hexane) in 200 mL of tetrahydrofuran (THF), maintained at room temperature under a nitrogen atmosphere, add during approximately 15 min a solution of the title alcohol from Step C (26.2. g, 141 mmol) in 50 mL of THF. Stir the reaction mixture for 2 h at room temperature. Add a solution of benzyl bromide (25.3 g, 148 mmol) in 50 mL of THF during about 5 minutes, while maintaining the mixture at around room temperature by use of a water bath. Stir for approximately 16 h at room temperature; then add another 0.56 g (14 mmol) of hexane-washed 60% sodium hydride, followed after 1 h by 2.44 g (14 mmol) of benzyl bromide. Stir for another 5 h at room temperature. Cool to below 20° C. by means of an ice-water bath, very cautiously add dropwise 10 mL of water (gas evolution) and stir the mixture for 15 min at 15°-20° C. Concentrate the reaction mixture under reduced pressure, treat the residue with ether (200 mL), and wash with water (3 ×100 mL), then brine (100 mL). Dry the solution over anhydrous sodium sulfate, filter out drying agent, and strip solvent under vacuum. Chromatograph the residue on silica gel, eluting with first 5% ethyl acetate in hexane, then with 10% ethyl acetate, to obtain the title compound as a slightly cloudy oil, which can be used without further purification in Step E below.

STEP E. 2-[7-(BENZYLOXY)HEPTYLOXY]-2-METHYLOXIRANE. To a stirred suspension of m-chloroperoxybenzoic acid (31.9 g of 85%; 157 mmol) in methylene chloride (180 mL), maintained at approximately 5° C. by means of an ice-water bath, add a solution of the title benzyl ether from Step D (36.5 g, 132 mmol) in methylene chloride (70 mL). Allow the mixture to warm slightly and stir at approximately 15° C. for 0.5 h, then for 2 h at room temperature. Cool the reaction mixture to about 5° C., and rapidly add a chilled solution of 1.1M sodium bicarbonate along with another 100-mL portion of methylene chloride. Stir and separate the layers. Wash the organic layer with cold water (3×100 mL), followed by cold brine (150 mL). Dry the solution over anhydrous magnesium sulfate, filter out the drying agent, and strip solvent under high vacuum to obtain the title epoxide as a clear, pale yellow oil, which may be used directly in Step F below, or, if desired, may be further purified by chromatography on silica gel, eluting with ethyl acetate-hexane (3:7). The clear, viscous oil isolated by chromatography is mainly the title epoxide containing a trace of m-chlorobenzoic acid.

STEP F. 3-[7-(BENZYLOXY)HEPTYLOXY]-2-METHYL-2-METHOXYPROPANOL. Treat prechilled 2-[7-(benzyloxy)heptyloxy]-2-methyloxirane (from Step E) (41.8 g, 132 mmol) with 430 mL of cold (−8° C.) anhydrous methanol. With temperature maintained at approximately −10° C. by means of an acetone-ice bath, stir the mixture to dissolve the epoxide. To the cold, stirred solution add p-toluenesulfonic acid monohydrate (2.5 g, 13 mmol). After 45 min at −10° C., strip the solution under vacuum, and chromatograph the residual oil on silica gel, eluting first with 30% ethyl acetate in hexane, then with 40% ethyl acetate, to obtain the title alcohol as a viscous oil which may be used directly in Step G. Note that the isomeric product, 3-[7-(benzyloxy)heptyloxy]-2-hydroxy-2-methyl-1-methoxypropane, also forms in the reaction and is isolated as a soft, partially solidified wax that elutes before the desired product in the system described above.

STEP G. 3-[7-(BENZYLOXY).HEPTYLOXY]-1-CHLOROFORMYLOXY-2-METHYL-2-METHOXYPROPANOL. To a stirred solution of the title alcohol from Step F (8.0 g, 24.7 mmol) in 25 mL of dry methylene chloride, maintained at 0°-5° C. by means of an ice-water bath, add a solution of trichloromethyl chloroformate (8.29 g, 42.0 mmol) in 25 mL of dry methylene chloride. Allow the mixture to warm to room temperature, stir for 18 h, dilute with 30 mL of dry methylene chloride, and add another 4.26 g (21.6 mmol) of trichloromethyl chloroformate. Stir at room temperature for 60 h, add another portion (2.46 g; 12.5 mmol) of the chloroformate reagent, and stir for 18 h. Remove volatile material at 35° C. and 3 mm pressure to obtain the title compound as a pale yellow oil, containing the corresponding trichloromethyl carbonate as a minor contaminant. This oil may be used without further purification in Step H below.

STEP H. CARBAMIC ACID, PHENYL{2-METHOXY-2-METHYL-3-[7-(BENZYLOXY)HEPTYLOXY]PROPYL}ESTER. Add a solution of aniline (3.58 g, 38.4 mmol) in 5 mL of methylene chloride to a stirred solution of the title chloroformate derivative from Step G (1.49 g, 3.84 mmol) in 5 mL of methylene chloride, maintained at 0°-5° C. by means of an ice-water bath. Stir in the cold bath for 15 rain, then allow the reaction mixture to warm to room temperature and continue stirring for 19.5 h. Filter the reaction mixture, and wash the filtrate successively with 3M HCl (1×) and water (3×). Dry the filtrate over anhydrous sodium sulfate, filter out drying agent, and remove solvent under reduced pressure. Chromatograph the residue on silica gel, eluting with ethyl acetate-hexane (3:7) to obtain the title carbamate as a viscous oil, which may be used directly in Step I below.

STEP I. CARBAMIC ACID, PHENYL{2-METHOXY-2-METHYL-3-[7-(HYDROXY)HEPTYLOXY]PROPYL}ESTER. Treat a mixture of the title benzyl ether from Step H (465 mg, 1.05 mmol) and 40 mg of 10% palladium-on-carbon catalyst in 8 mL of anhydrous methanol on a Parr shaker under an atmosphere of hydrogen at 56 psi for 26 h. Filter out the catalyst, and remove solvent from the filtrate under reduced pressure. Chromatograph the residue on silica gel, eluting with ethyl acetate-hexane (1:1), to obtain the title deprotected alcohol as a colorless, viscous oil, which may be used without further treatment in Step J below.

STEP J. CARBAMIC ACID, PHENYL{2-METHOXY-2-METHYL-3-[7-(METHANESULFONYLOXY)HEPTYLOXY]PROPYL}ESTER. Add a solution of methanesulfonyl chloride (87 mg, 0.756 mmol) in 1 mL of benzene to a stirred solution of the title alcohol from Step I (255 mg, 0.720 retool) and triethylamine (76.5 mg, 0.756 mmol) in 3 mL of benzene, maintained at 5°-10° C. by means of an ice-water bath. Stir in the cold bath for 5 min, then allow the reaction mixture to warm to room temperature and continue stirring for 3 h at room temperature. Add 12 mL of ether and filter the resultant mixture. Remove volatiles from the filtrate under high vacuum to obtain the title mesylate as a viscous oil, which can be used directly in Step K.

STEP K. CARBAMIC ACID, PHENYL[2-METHOXY-2-METHYL-3-(7-THIAZOLIUMHEPTYLOXY)PROPYL]ESTER METHANESULFONATE. Heat a solution of the title mesylate from Step J (242 mg, 0.56 mmol) and thiazole (1 mL, 1.20 g, 14.1 mmol) at 80° C. for 18 h under an atmosphere of nitrogen. Distill off excess thiazole at approximately 2 mm pressure, and remove last traces of the reagent under high vacuum. Chromatograph the residue on silica gel, eluting with methylene chloride-methanol-water (80:18:0.5). Further purify the title compound by rechromatographing the material thus isolated on silica gel, eluting with methylene chloride-methanol-water (using a stepped gradient beginning with 90:9:0.25, followed by 80:18:0.25) to obtain the methanesulfonate salt of the title thiazolium derivative as a viscous oil, which has the following spectroscopic characteristics:

FAB mass spectrum: parent peak at m/z 421, corresponding to the molecular cation of the title compound.

$^1$H NMR spectrum (200 MHz; CDCl$_3$; δ-values in ppm downfield from TMS internal standard): δ11.05 (br s; 1H); 8.18 (m; 1H); 8.07 (m; 1H); 7.44 (d; J≅7.5 Hz; 2H); 7.27 (t; J≅7.5 Hz; 2H); 7.04 (t; J≅7.5 Hz; 1H); 4.65 (t;

J≅7.5 Hz; 2H); 4.24 (d; J≅12 Hz; 1H); 4.14 (d; J≅12 Hz; 1H); 3.54–3.38 (m; 4H); 3.32 (s; 3H); 2.80 (s; 3H); approx. 2.0–1.75 (br m; >2H; overlapped by broad water peak); 1.53 (m; 2H); 1.35 (br s; 6H); 1.21 (s; 3H).

EXAMPLE 29

3-{7-[3-(2-AMINO-2,3,4,5-TETRAHYDRO)-THIAZOLYL]HEPTYLOXY}-2-METHOXY-2-METHYLPROPYL, 2.4-DIFLUOROPHENYLCARBAMATE

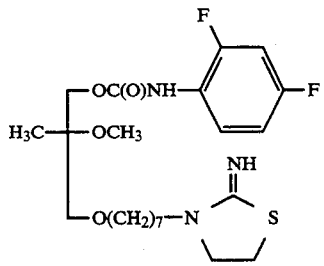

STEP A. 3-[7-(BENZYLOXY)HEPTYLOXY]-2-METHOXY-2-METHYLPROPYL, 2,4-DIFLUOROPHENYLCARBAMATE. The preparation of the title compound follows the method described in Step H of Example 28 (CARBAMIC ACID, PHENYL[2-METHOXY-2-METHYL-3-(7-THIAZOLIUMHEPTYLOXY)PROPYL]ESTER, METHANESULFONATE) except that the mode of mixing the reagents is reversed: In the present example, add a solution of 2,4-difluoroaniline (3.64 g, 28.2 mmol) in 5 mL of methylene chloride to a mixture of 2.93 mmol of 3-[7-(benzyloxy)heptyloxy]-1-chloroformyloxy-2-methyl-2 methoxypropanol and the corresponding trichloromethoxycarbonyl derivative (prepared as described in Step G of Example 28) dissolved in 15 mL of methylene chloride. Following workup, chromatograph the crude material on silica gel, eluting with ethyl acetate-hexane in a stepped gradient starting with 10% ethyl acetate, followed by 17% ethyl acetate, to obtain the title compound of this example as a viscous oil, which may be used directly in Step B below.

STEP B. 3-[7-(HYDROXY)HEPTYLOXY]-2-METHOXY-2METHYLPROPYL, 2.4-DIFLUOROPHENYLCARBAMATE. The preparation of the title compound follows the method described in Step I of Example 28 (CARBAMIC ACID, PHENYL[2-METHOXY-2-METHYL-3-(7-THIAZOLIUMHEPTYLOXY)PROPYL]ESTER, METHANESULFONATE). As described therein, hydrogenate a mixture of the title benzyl ether from Step A above (880 mg, 1.83 mmol) and 180 mg of 10% palladium-on-carbon catalyst in 50 mL of methanol for 5 h at 58 psi. Filter off catalyst, and remove solvent from the filtrate under reduced pressure to obtain the title alcohol as a viscous oil, which may be used without further purification in Step C below.

STEP C. 3-[7-(METHANESULFONYLOXY)-HEPTYLOXY]-2-METHOXY-2-METHYLPROPYL, 2,4-DIFLUOROPHENYLCARBAMATE. The preparation of the title compound follows the method described in Step J of Example 28 (CARBAMIC ACID, PHENYL[2-METHOXY-2-METHYL-3-(7-THIAZOLIUMHEPTYLOXY)PROPYL]ESTER, METHANESULFONATE). Add a solution of methanesulfonyl chloride (253 mg, 1.75 mmol) in 2 mL of benzene to a stirred solution of the title alcohol from Step B (650 mg, 1.67 mmol) and triethylamine (177 mg, 1.75 mmol) in 6 mL of benzene, maintained at 5°–10° C. by means of an ice-water bath. Stir in the cold bath for 5 min, then allow the reaction mixture to warm to room temperature, and continue stirring for 3 h at room temperature. Add 15 mL of ether, and filter the resultant mixture. Remove volatiles from the filtrate under high vacuum to obtain the title mesylate as a viscous oil, which can be used directly in Step D.

STEP D. 3-{7-[3-(2-IMINO-2,3,4,5-TETRAHYDRO)THIAZOLYL]HEPTYLOXY}-2-METHOXY-2-METHYLPROPYL, 2.4-DIFLUOROPHENYLCARBAMATE. Heat a solution of the title mesylate from Step C (660 mg, 1.41 mmol) and 2-amino-2-thiazoline (432 mg, 4.23 mmol) in 14 mL of dry DMF at 50° C. for 26.5 h under an atmosphere of nitrogen. Allow the reaction mixture to cool to room temperature, add 25 mL of ethyl acetate and 10 mL of 1.1M aqueous sodium bicarbonate, filter the resultant mixture, and separate the layers. Wash the organic layer with water (3×5 mL), and dry over anhydrous sodium sulfate. Filter out the drying agent, and remove solvent from the filtrate under reduced pressure. Chromatograph the residue on silica gel, eluting with methylene chloride-methanol-ammonium hydroxide (90:9:0.25). Further purify the title compound by rechromatographing the material thus isolated on silica gel, eluting with methylene chloride-methanol-ammonium hydroxide (using a stepped gradient beginning with 96:4:0.15, followed by 90:9:0.15) to obtain the title compound as a viscous oil, which has the following spectroscopic characteristics:

Chemical ionization mass spectrum: parent peak at m/z 474, corresponding to the [M+1]+-peak of the title compound. ¹H NMR spectrum (200 MHz; CDCl₃; δ-values in ppm downfield from TMS internal standard): δ8.04 (br m; NH); 6.95–6.78 (m; 3H); 4.28 (d; J≅11 Hz; 1H); 4.18 (d; J≅11 Hz; 1H); 3.61 (t; J≅6 Hz; 2H); 3.52–3.30 (overlapping multiplets; 6H); 3.32 (s; 3H); 3.13 (t; J≅6 Hz; 2H); 1.56 (m; 4H); 1.32 (m; 6H); 1.21 (s; 3H).

EXAMPLE 30

CARBAMIC ACID, PHENYL[2-METHYL-2-METHANESULFONYL-3-{4-[3-(2,3,4,5-TETRAHYDRO-2-IMINO)-THIAZOLYLMETHYL]PHENYLMETHOXY} PROPYL]ESTER, HYDROCHLORIDE MONOHYDRATE

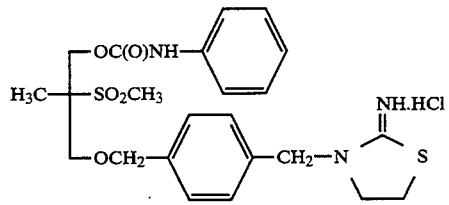

STEP A. 1-IODOMETHYL-4-[(1,1-DIMETHYLETHYL)DIMETHYLSILYL]-OXYMETHYLBENZENE. Reflux for 4.5 h a mixture of 1-bromomethyl-4-[(1,1-dimethylethyl)dimethylsilyl]oxymethylbenzene (8.50 g, 26.9 mmol; from Preparative Example 20) and sodium iodide (14.1 g, 94.0 mmol) in 460 mL of dry acetone. Remove solvent under reduced pressure, treat the residue with 300 mL of ether, stir for 15 min, and filter. Wash the filter cake with methylene chloride, and strip solvent under reduced pressure from the combined filtrate and washes to obtain the title iodide as a brown oil that may be used directly in Step B below.

STEP B. 3-{[4-[(1,1-DIMETHYLETHYL)DIMETHYLSILYL]-OXYMETHYL]-PHENYLMETHOXY}-2-METHYL-2-METHYLTHIOPROPANOL. Add dropwise at room temperature a solution of 2-methylthio-2-methylpropane-1,3-diol from Preparative Example 4 (2.4 g, 17.6 mmol) in 18 mL of DMF to a suspension of sodium hydride (772 mg of a 60% dispersion, 19.4 mmol; prewashed with petroleum ether) in 25 mL of DMF. Stir the resultant suspension at room temperature for 1.5 h. Add another 75 mL of DMF, cool the mixture to approximately 0° C., and add a solution of the title iodide from Step A (8.0 g, 22.1 mmol). Stir the mixture at 0° C. for 20 h. Add a few drops of water to quench excess sodium hydride, and remove solvent under high vacuum. Chromatograph the residual oil on silica gel, eluting with ethyl acetate-hexane (1:7), to obtain the title alcohol as a yellow oil that can be used directly in Step C below.

STEP C. 3-{[4-[(1,1-DIMETHYLETHYL)DIMETHYLSILYL]-OXYMETHYL]-PHENYLMETHOXY}-2-METHYL-2METHYLTHIOPROPYL, PHENYLCARBAMATE. Reflux a solution of the alcohol from Step B (6.26 g, 16.9 mmol) and phenyl isocyanate (3.04 g, 25.5 mmol) in 150 mL of 1,2-dichloroethane for 24 h. Remove solvent under reduced pressure, and chromatograph the residue on silica gel, eluting with ethyl acetate-hexane (1:8) to obtain the title carbamate as an oil, which may be used directly in Step D below.

STEP D. 3-[4-(HYDROXYMETHYL)PHENYLMETHOXY]2-METHYL-2-METHYLTHIOPROPYL, PHENYLCARBAMATE. Stir at room temperature for 2 h a solution of the title silyl ether from Step C above (7.62 g, 15.6 mmol) and tetrabutylammonium fluoride trihydrate (5.89 g, 18.7 mmol) in 100 mL of THF. Remove solvent under reduced pressure, dissolve the residue in ether (450 mL), wash successively with water (2×200 mL) and brine (100 mL), and remove ether under reduced pressure. Dissolve the residue in methylene chloride, dry over anhydrous sodium sulfate, filter out the drying agent, and remove solvent under reduced pressure. Chromatograph the residue on silica gel, eluting with a gradient system of 20–50% ethyl acetate in hexane, to obtain the title alcohol as a pale yellow oil, which can be used directly in Step E below.

STEP E. 3-[4-(BROMOMETHYL)PHENYLMETHOXY]-2-METHYL-2-METHYLTHIOPROPYL, PHENYLCARBAMATE. To a stirred solution of the title alcohol from Step D above (400 mg, 1.07 retool) in 7 mL of acetonitrile, add successively at room temperature triphenylphosphine (370 mg, 1.41 mmol), acetonitrile (13 mL), and carbon tetrabromide (464 mg, 1.40 mmol). Continue stirring at room temperature for 2h. Remove solvent under reduced pressure, and chromatograph the residue on silica gel, eluting with ethyl acetate-hexane in a stepped gradient of first 17%, then 25%, ethyl acetate to obtain the title bromide as gummy yellow solid that can be used directly in Step F below.

STEP F. 3-[4-(BROMOMETHYL)PHENYLMETHOXY]-2-METHANESULFONYL-2-METHYLPROPYL, PHENYLCARBAMATE. To a stirred solution of the title bromide from Step E above (310 mg, 0.707 mmol) in 20 mL of methylene chloride, add portionwise at room temperature m-chloroperoxybenzoic acid (490 mg, 2.24 mmol) (temperature rises). Continue stirring at room temperature for 2 h, dilute with 15 mL of methylene chloride, and wash the reaction solution successively with water (20 mL) and brine (20 mL). Dry the solution over anhydrous sodium sulfate, filter out the drying agent, and remove solvent under vacuum. Chromatograph the residue on silica gel, eluting with ethyl acetate-hexane in a stepped gradient of first 25%, then 33%, ethyl acetate, to obtain the title sulfone as a viscous oil that can be used directly in Step G below.

STEP G. CARBAMIC ACID, PHENYL[2-METHYL-2-METHANESULFONYL-3-{4-[3-(2,3,4,5-TETRAHYDRO-2-IMINO)THIAZOLYLMETHYL]-PHENYLMETHOXY}-PROPYL]ESTER, HYDROCHLORIDE MONOHYDRATE. Stir at room temperature for 5 h a solution of the title compound from Step F above (530 mg, 1.13 mmol) and 2-aminothiazoline (350 mg, 3.42 mmol) in 5.5 mL of DMF. Remove solvent under high vacuum, dissolve the residue in methylene chloride (50 mL), and wash the solution with saturated aqueous sodium bicarbonate (25 mL). Dry the solution over anhydrous sodium sulfate, filter out the drying agent, and remove solvent under vacuum. Chromatograph the residue on silica gel, eluting with methylene chloride-ethanol-ammonium hydroxide (concentrated) in a stepped gradient beginning with 50:5:0.25, followed by 50:8:0.25, to obtain the title compound in its free base form as a white solid. Stir at room temperature for 0.5 h a solution of this free base (168 mg, 0.341 mmol) and 0.15 mL of 3.4M ethereal hydrochloric acid (0.512 mmol) in 15 mL of methanol. Remove volatiles under high vacuum to obtain the title hydrochloride as a monohydrate which shrinks at approximately 61° C. and decomposes at around 112° C. (variable, depending upon rate of heating) and exhibits the following selected spectral characteristics:

$^1$H NMR (200 MHz; CDCl$_3$ containing a few drops of DMSO-d$_6$; δ-values in ppm downfield from TMS internal standard): δ10.55 (xch s; >1H); 9.20 (xch s; 1H); 4.94 (s; 2H); 4.56 (s; 2H); 4.55 (d; 1H); 4.38 (d; 1H); 3.80–3.70 (m; 4H); 3.55 (s; 3H); 3.39 (m; 2H); 1.42 (s; 3H).

The FAB mass spectrum exhibits an (M+1)$^+$-peak at m/z 492.

EXAMPLE 31

CARBAMIC ACID, PHENYL[2-METHYL-2-METHANESULFONYL-3-{4-[3-(2,3,4,5-TETRAHYDRO-2-IMINO-4-CARBOXY)-THIAZOLYLMETHYL]PHENYLMETHOXY} PROPYL]ESTER, HEMIHYDRATE

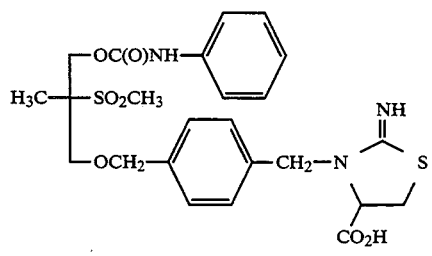

STEP A. CARBAMIC ACID, PHENYL[2-METHYL-2-METHANESULFONYL-3-{4-[3-(2,3,4,5-TETRAHYDRO-2-IMINO-4-METHOXYCARBONYL)-THIAZOLYL-METHYL]PHENYLMETHOXY}-PROPYL]ESTER. Stir at room temperature for 4 h a solution of 3-[4-(bromomethyl)phenylmethoxy-2-methanesulfonyl-2-methylpropyl, phenylcarbamate (290 mg, 0.616 mmol; from Step F of preparation of CARBAMIC ACID, PHENYL[2-METHYL-2-METHANESULFONYL-3-{4-[3-(2,3,4,5,-TETRAHYDRO-2-IMINO)THIAZOLYLMETHYL]-PHENYLMETHOXY}-PROPYL]ESTER. HYDROCHLORIDE MONOHYDRATE above) and methyl 2-amino-2-thiazoline-4-carboxylate (197 mg, 1.23 mmol; prepared by acid-catalyzed esterification of the corresponding carboxylic acid) in 2 mL of DMF. Remove solvent under high vacuum, dissolve the residue in 15 mL of methylene chloride, and wash successively with saturated aqueous sodium bicarbonate (2×10 mL), brine, and water. Dry the solution over anhydrous sodium sulfate, filter out the drying agent, and remove solvent under reduced pressure. Chromatograph the residue on silica gel, eluting with acetone-methylene chloride (2:1) to obtain the partially purified title compound. Rechromatograph this material on silica gel, eluting with methylene chloride-ethanol-water (90:2:0.1), to obtain the title ester, which may be used directly in Step B below.

STEP B. CARBAMIC ACID, PHENYL[2-METHYL-2-METHANESULFONYL-3-{4-[3-( 2,3,4,5-TETRAHYDRO-2-IMINO-4-CARBOXY)THIAZOLYLMETHYL]-PHENYLMETHOXY}PROPYL]-ESTER, HEMIHYDRATE. Stir at 0°–5° C. for 4 h a solution of the title ester from Step A above (230 mg, 0.423 mmol) and sodium hydroxide (0.288 mL of a 2.5M aqueous solution, 0.719 mmol) in 1.2 mL of methanol. Allow the reaction mixture to warm to approximately 8° C., and stir for another 40 min. Adjust the pH to approximately 5 by the addition of 6N HCl, and remove volatiles under vacuum. Redissolve the residue in methanol, and filter the solution through a pad of silica gel, eluting with methylene chloride-methanol (1:1). Strip solvent from the filtrate under vacuum, and chromatograph the residue on silica gel, eluting with methylene chloride-methanol-water (75:15:1) to obtain the title amino acid as an off-white solid that decomposes over a broad range (145°–164° C.) and exhibits the following selected spectral characteristics:

$^1$H NMR (200 MHz; DMSO-d$_6$; δ-values in ppm downfield from TMS internal standard): δ9.80 (xch d; 1H); 9.42 (xch br s; 1H); 7.49 (d; 2H); 7.49–7.20 (m; 6H); 7.02 (t; 1H); 5.00 (d; J≅15 Hz; 1H); 4.70–4.30 (m; 3H); 4.55 (s; 2H); 4.14–4.01 (m; 1H); 3.80 (d; J≅13 Hz; 1H); 3.72 (d; J≅13 Hz; 1H); 3.68–3.50 (m; 2H); 3.08 (s; 3H); 1.32 (s; 3H).

The FAB mass spectrum exhibits an (M+1)$^+$-peak at m/z 536.

EXAMPLE 32

3-{4-[3-(2-IMINO-2,3,4,5-TETRAHYDRO)-THIAZOLYL]BUTYLOXY}-2-ETHYL-2-METHYLPROPYL, 2,4-DIFLUOROPHENYLCARBAMATE

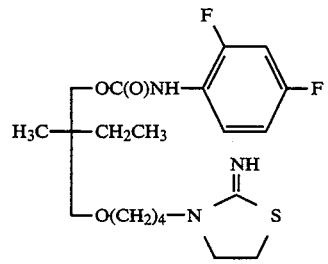

STEP A. 3-[4-(t-BUTYLDIMETHYLSILYLOXY)-BUTYLOXY]-2-ETHYL-2-METHYLPROPANOL. To a stirred solution of diethyl 2-ethyl-2-methyl malonate (1.75 g, 14.8 mmol; prepared as described in Preparative Example 1) in 10 mL of DMF, maintained under a nitrogen atmosphere and at room temperature by means of a water bath, add portionwise over approximately 0.5 h a sodium hydride dispersion (0.62 g of 60% in mineral oil, 15.5 mmol). Continue stirring for 1 h at room temperature before cooling the reaction mixture to approximately 5° C. and adding dropwise over approximately 0.5 h a solution of I(CH$_2$)$_4$OSi(CH$_3$)$_2$C(CH$_3$)$_3$ (4.42 g, 15.5 mmol) in 2 mL of DMF. Remove the cooling bath, and allow the reaction mixture to stir at room temperature for 19 h. Dilute the mixture with 25 mL of ethyl acetate, and wash the resultant solution with 15 mL of water. Saturate the aqueous wash with sodium chloride, and extract with ethyl acetate (3×15 mL). Combine the organic extracts, wash successively with water (3×10 mL) and brine (15 mL), and dry over anhydrous magnesium sulfate. Filter out the drying agent, remove solvent from the filtrate under reduced pressure, and chromatograph the residue on silica gel, eluting with ethyl acetate-hexane (1:9), to obtain the title compound as a clear, viscous oil, which may be used directly in Step B below.

STEP B. 3-[4-(t-BUTYLDIMETHYLSILYLOXY)-BUTYLOXY]-2-ETHYL-2-METHYLPROPYL, 2,4-DIFLUOROPHENYLCARBAMATE. Heat a solution of the title alcohol from Step A above (954 mg, 3.13 mmol) and 2,4-difluorophenylisocyanate (1.07 g, 6.88 mmol) in 7 mL of 1,2-dichloroethane at 80° C. under a nitrogen atmosphere for 8 h. Remove volatile material at 40° C. and 2 mm pressure. Treat the residue with methylene chloride, and evaporate under reduced pressure. Repeat this procedure twice, and then dry under high vacuum to remove last traces of volatile impurities and thus obtain the title carbamate as a soft solid which can be used directly in Step C below.

STEP C. 3-[4-(HYDROXY)BUTYLOXY]2-ETHYL-2-METHYLPROPYL, 2,4-DIFLUOROPHENYLCARBAMATE. Stir for approximately 10 min a solution of the title silyl ether from Step B (1.52 g, 3.13 mmol) and tetrabutylammonium fluoride trihydrate (0.99 g, 3.13 mmol) in 10 mL of dry tetrahydrofuran, maintained under a nitrogen atmosphere at −10° C. Remove the cooling bath, and allow the reaction mixture to stand at room temperature for 2 h. Remove volatiles at reduced pressure, dissolve the residual oil in 25 mL of methylene chloride, and wash the solution successively with water (3×5 mL) and brine (15 mL). Dry over anhydrous magnesium sulfate, filter out the drying agent, and remove solvent under reduced pressure to obtain the title alcohol as an oil, which can be used without further purification in Step D below.

STEP D. 3-[4-(METHANESULFONYLOXY)-BUTYLOXY]2-ETHYL-2-METHYLPROPYL, 2,4-DIFLUOROPHENYLCARBAMATE. To a solution of the title alcohol from Step C (920 mg, 2.67 mmol) and triethylamine (270 mg, 2.65 mmol) in 10 mL of dry benzene, maintained at approximately 10° C., add a solution of methanesulfonyl chloride (310 mg, 2.71 mmol) in 2 mL of dry benzene. Remove the cooling bath, and allow the resultant solution to stand at room temperature for 3 h. Treat the reaction mixture with 25 mL of ether, filter the resultant mixture, and remove volatiles under reduced pressure to obtain the title mesylate as a viscous amber oil, which may be used without further purification in Step E below.

STEP E. 3-{4-[3-(2-IMINO-2,3,4,5-TETRAHYDRO)THIAZOLYL]BUTYLOXY}2-ETHYL-2-METHYLPROPYL, 2,4-DIFLUOROPHENYL-CARBAMATE. Heat at 50°-60° C. for 48 h under a nitrogen atmosphere a solution of the title mesylate from Step D (768 mg, 1.81 mmol) and 2-amino-2-thiazoline (541 mg, 5.29 mmol) in 15 mL of dry DMF. Concentrate the solution under reduced pressure, and chromatograph the residue on silica gel, eluting with methylene chloride-methanol-ammonium hydroxide (95:5:0.25) to obtain a partially purified sample of the title compound. Rechromatograph this material on silica gel, eluting with methylene chloride-methanol-ammonium hydroxide (95:5:0.15) to obtain the title compound as a viscous amber oil, which has the following spectroscopic characteristics:

FAB mass spectrum: parent peak at m/z 430, corresponding to the [M+1]$^+$-peak of the title compound. $^1$H NMR spectrum (200 MHz; CDCl$_3$; δ-values in ppm downfield from TMS internal standard): δ8.00 (br m; NH); 7.00-6.82 (m; 3H); 4.04 (s; 2H); 3.61 (t; J≅8 Hz; 2H); 3.43 (t; J≅6 Hz; 2H); 3.40 (t; J≅8 Hz; 2H); 3.23 (d; J≅9 Hz; 1H); 3.18 (d; J≅9 Hz; 1H); 3.13 (t; J≅8 Hz; 2H); 1.62 (m; 4H); 1.37 (m; 2H); 0.90 (s; 3H); 0.86 (t; J≅8 Hz; 3H).

The following formulations exemplify some of the dosage forms of the compositions of this invention. In each, the term "active compound" designates 3-[7-[3-(2,3-dihydro-2-imino)thiazolyl]heptyloxy]-2-methoxy-2-methylpropyl-N-methyloctadecyl carbamate. It is contemplated, however, that this compound may be replaced by an effective amount of another compound of formula I.

Pharmaceutical Dosage Form Example

Example A

Tablets

| No. | Ingredient | mg/tablet | mg/tablet |
|---|---|---|---|
| 1. | Active compound | 10 | 50 |
| 2. | Lactose USP | 212 | 563 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10-15 minutes. Granulate the mixture with Item No. 3. Mill the damp granules through a coarse screen (e.g., ¼") if needed. Dry the damp granules. Screen the dried granules if needed and mix with Item No. 4 and mix for 10-15 minutes. Add Item No. 5 and mix for 1-3 minutes. Compress the mixture to appropriate size and weight on a suitable tablet machine.

Example B

Capsules

| No. | Ingredient | mg/capsule | mg/capsule |
|---|---|---|---|
| 1. | Active compound | 10 | 50 |
| 2. | Lactose USP | 196 | 573 |
| 3. | Corn Starch, Food Grade | 40 | 70 |
| 4. | Magnesium Stearate NF | 4 | 7 |
| | Total | 250 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

Example C

Parenteral

| Ingredient | mg/vial | mg/vial |
|---|---|---|
| Active Compound | 10 | 50 |

Add sterile water for injection or bacteriostatic water for injection, for reconstitution.

Example D

Injectable

| Ingredient | mg/vial |
|---|---|
| Active Compound | 100 |
| Methyl p-hydroxybenzoate | 1.8 |
| Propyl p-hydroxybenzoate | 0.2 |
| Sodium Bisulfite | 3.2 |
| Disodium Edetate | 0.1 |
| Sodium Sulfate | 2.6 |
| Water for Injection q.s. ad | 1.0 ml |

Method of Manufacture (for 1000 vials)
1. Dissolve p-hydroxybenzoate compounds in a portion (85% of the final volume) of the water for injection at 65°-70° C.
2. Cool to 25°-35° C. Charge and dissolve the sodium bisulfite, disodium edetate and sodium sulfate.
3. Charge and dissolve active compound.
4. Bring the solution to final volume by added water for injection.
5. Filter the solution through 0.22 membrane and fill into appropriate containers.
6. Finally sterilize the units by autoclaving.

Example E

Nasal Spray

| Ingredient | mg/ml |
| --- | --- |
| Active Compound | 10.0 |
| Phenyl Mercuric Acetate | 0.02 |
| Aminoacetic Acid USP | 3.7 |
| Sorbitol Solution, USP | 57.0 |
| Benzalkonium Chloride Solution | 0.2 |
| Sodium Hydroxide 1N Solution to adjust pH | |
| Water Purified USP to make | 1.0 ml |

Example F

Ointment

| Formula | mg/g |
| --- | --- |
| Active Compound | 1.0–20.0 |
| Benzyl Alcohol, NF | 20.0 |
| Mineral Oil, USP | 50.0 |
| White Petrolatum, USP to make | 1.0 g |

Method of Manufacture

Disperse active compound in a portion of the mineral oil. Mix and heat to 65° C., a weighed quantity of white petrolatum, the remaining mineral oil and benzyl alcohol, and cool to 50°–55° C. with stirring. Add the dispersed active compound to the above mixture with stirring. Cool to room temperature.

Example G

Cream

| Formula | mg/g |
| --- | --- |
| Active Compound | 1.0–20.0 |
| Stearic Acid, USP | 60.0 |
| Glyceryl Monostearate | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Method of Manufacture

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed stirring. Dissolve the active compound in remaining quantity of propylene glycol and add to the above emulsion when the temperature of emulsion is 37°–40° C. Mix uniformly with stirring and cool to room temperature.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound represented by structural formula I

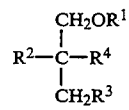

or a pharmaceutically acceptable salt or solvate thereof wherein:

$R^1$ is 6 to 22 carbon alkyl, —C(O)—D or —C(S)—D wherein

D is $NR^5R^6$;

$R^5$ is hydrogen, x carbon alkyl, aryl, heteroaryl, heteroalkyl, arylalkyl, or cycloalkyl, wherein said alkyl, aryl, heteroaryl, heteroalkyl, arylalkyl or cycloalkyl groups may be substituted;

$R^6$ is y carbon alkyl, aryl, heteroaryl, heteroalkyl, arylalkyl or cycloalkyl, wherein said alkyl, aryl, heteroaryl, heteroalkyl, arylalkyl and cycloalkyl groups may be substituted, such that the sum of x and y, when at least one of $R^5$ or $R^6$ is alkyl is an integer of from 1 to 22; or $R^5$ or $R^6$ together with the nitrogen to which they are attached may form a heterocycloalkyl group which may be substituted with alkyl or arylalkyl;

$R^2$ is lower alkyl, trifluoromethyl, arylalkyl or aryl, wherein said aryl and said arylalkyl groups may be substituted;

$R^3$ is T—U—V, wherein

T represents —OPO$_3$—, O—C(O)—O—, —O—, —S—, —NR$^a$—, —NR$^a$SO$_2$—, —O—C(O)—N-R$^a$— or —NR$^a$—C(O)—O— wherein R$^a$ is H, lower alkyl or acyl;

U is —(CH$_2$)$_e$— wherein e is an integer of from 2 to 10 or

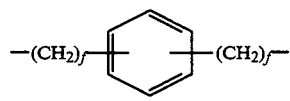

where each f is independently 1, 2 or 3;

V is A—B, wherein A is a direct bond between U and B, —O—, —S—, —O—(CH$_2$)$_n$— where n is 1,2 or 3, —O—C(O)— or —N(R$^a$)— where R$^a$ is as previously defined;

B is heterocycloalkyl or substituted heterocycloalkyl wherein said heterocycloalkyl is selected from the group consisting of: thiazolidinyl and thiazolidinium; or B is heteroaryl or substituted heteroaryl wherein said heteroaryl is selected from the group consisting of: thiazolyl and thiazolium; or B is selected from the group consisting of:

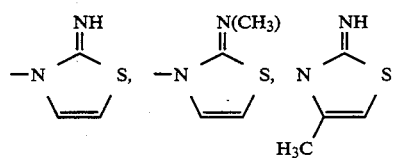

and

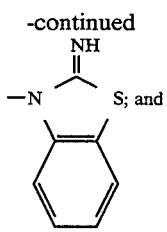

R[4] represents —X—C$_b$H$_{2b+1}$ where b is an integer of from 1 to 6 and X is methylene, O, S(O)$_c$ where c is 0, 1 or 2 or —N(R$^a$)— where R$^a$ is as previously defined;

wherein:

for said alkyl, cycloalkyl and heteroalkyl the substituents for each substitutable carbon atom, when substituted, are selected from the group consisting of: alkyl, =NR$^a$, —N(R$^a$)$_2$, —SR$^a$, —OR$^a$ and —CO$_2$R$^a$, wherein R$^a$ is as defined above, and the substituents for each substitutable heteroatom, when substituted, are selected from the group consisting of: —N(R$^a$)$_2$, —OR$^a$, —SR$^a$ and —CO$_2$R$^a$;

for said aryl and heteroaryl the substituents for each substitutable carbon atom, when substituted, are selected from the group consisting of: halo, alkyl, =NR$^a$, —N(R$^a$)$_2$, —SR$^a$, —OR$^a$ and —CO$_2$R$^a$, wherein R$^a$ is as previously defined, and the substituents for each substitutable heteroatom, when substituted, are selected from the group consisting of: alkyl, —N(R$^a$)$_2$, —SR$^a$, —OR$^a$ and —CO$_2$R$^a$, wherein R$^a$ is as previously defined;

for said heterocycloalkyl the substituents for each substitutable carbon atom, when substituted, are selected from the group consisting of: alkyl, =NR$^a$, —N(R$^a$)$_2$, —SR$^a$, —OR$^a$ and —CO$_2$R$^a$, wherein R$^a$ is as previously defined, and the substituents for each substitutable heteroatom, when substituted, are selected from the group consisting of: —N(R$^a$)$_2$, —OR$^a$, —SR$^a$, and —CO$_2$R$^a$, wherein R$^a$ is as previously defined; and with the proviso that when R$^1$ is alkyl, T cannot be —OPO$_3$.

2. A compound as defined by claim 1, wherein R$^1$ is —C(O)—D, and D is as defined in claim 1.

3. A compound as defined by claim 2, wherein R$^2$ is lower alkyl.

4. A compound as defined by claim 3, wherein T is —O—C(O)—O—, —O—, —O—(C(O)—NR$^a$ or —N-R$^a$—CO$_2$, wherein R$^a$ is as defined in claim 1.

5. A compound as defined by claim 3, wherein T is —O—.

6. A compound as defined by claim 5, wherein U is

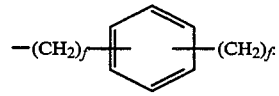

7. A compound as defined by claim 6, wherein A is a direct bond between U and B and B is heteroaryl or substituted heteroaryl.

8. A compound as defined by claim 5, wherein A is a direct bond between U and B and B is heterocycloalkyl or substituted heterocycloalkyl.

9. A compound as defined by claim 5, wherein A is —O— and B is heteroaryl or substituted heteroaryl.

10. A compound as defined by claim 9, wherein in R$^4$, b is 1 and X is O or SO$_2$.

11. A compound having a formula selected from:

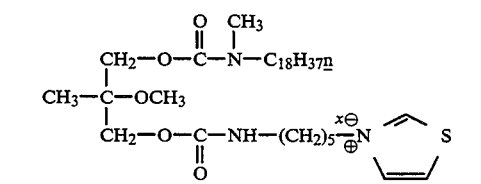
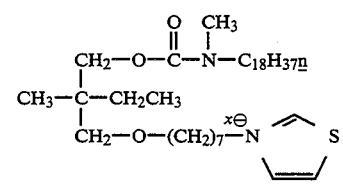
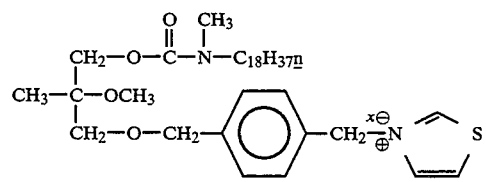
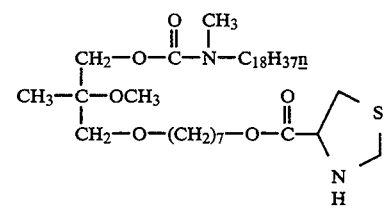
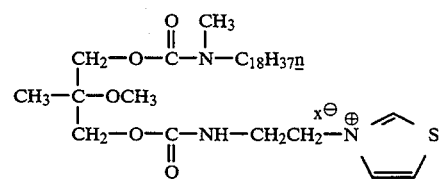
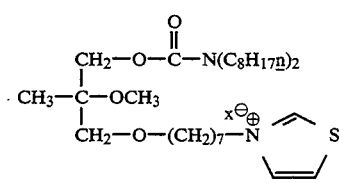
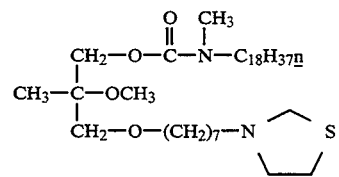
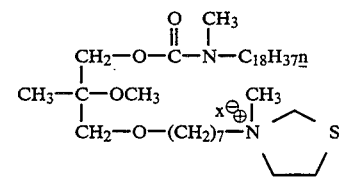

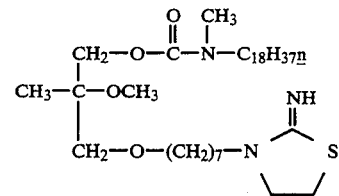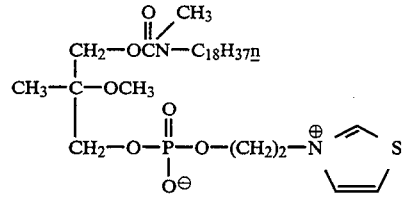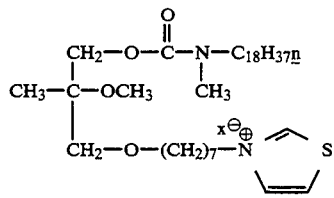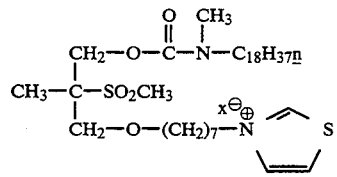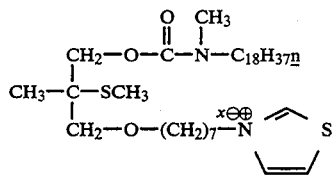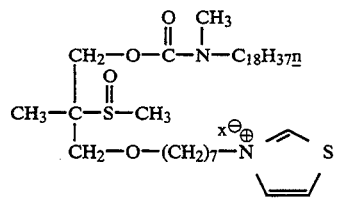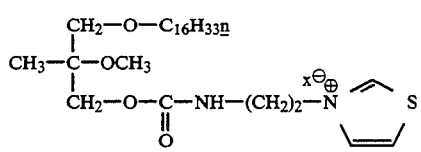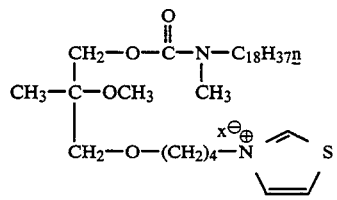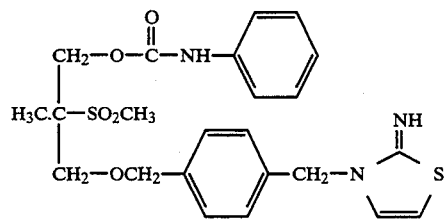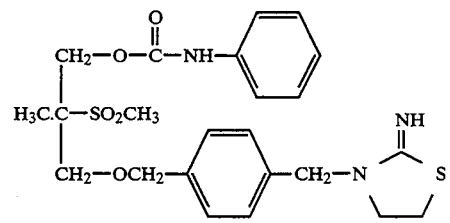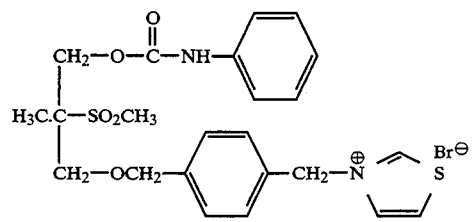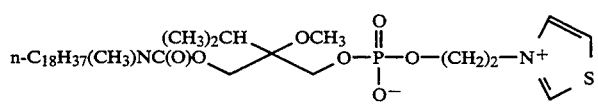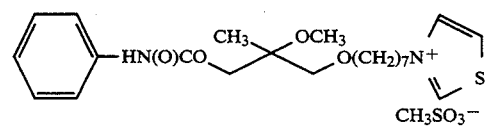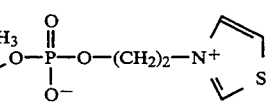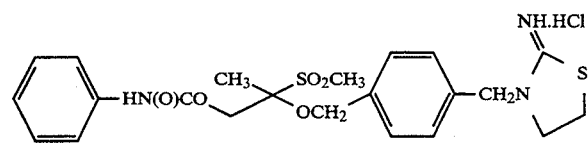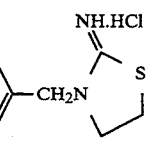

-continued

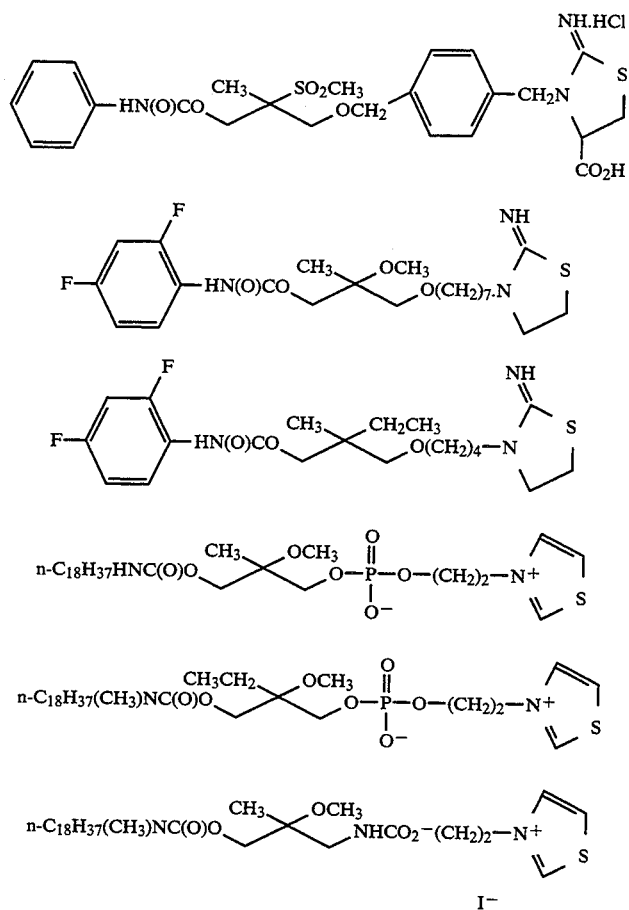

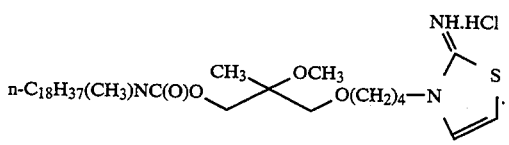

12. A pharmaceutical composition which comprises a compound having a structural formula I as defined in claim 1 in combination with a pharmaceutically acceptable carrier.

13. A pharmaceutical composition which comprises a compound having a structural formula as defined in claim 11 in combination with a pharmaceutically acceptable carrier.

14. A method for treating allergic reactions in a mammal comprising administering an antiallergic effective amount of a compound of formula I as defined by claim 1 to said mammal.

15. A method for treating allergic reactions in a mammal comprising administering an antiallergic effective amount of a compound of formula I as defined by claim 11 to said mammal.

16. A method for treating inflammation in a mammal comprising administering an antiinflammatory effective amount of a compound of formula I as defined by claim 1 to said mammal.

17. A method for treating inflammation in a mammal comprising administering an antiinflammatory effective amount of a compound of formula I as defined by claim 11 to said mammal.

* * * * *